(12) United States Patent
Noda et al.

(10) Patent No.: US 11,540,940 B2
(45) Date of Patent: Jan. 3, 2023

(54) SYSTEMS AND METHODS FOR VISCOELASTIC DELIVERY

(71) Applicant: Alcon Inc., Fribourg (CH)

(72) Inventors: Wayne A. Noda, Mission Viejo, CA (US); Omar Harouny, Rancho Cucamonga, CA (US); Daniel Hyman, Foothill Ranch, CA (US)

(73) Assignee: Alcon Inc., Fribourg (CH)

( * ) Notice: Subject to any disclaimer, the term of this patent is extended or adjusted under 35 U.S.C. 154(b) by 0 days.

(21) Appl. No.: 17/572,064

(22) Filed: Jan. 10, 2022

(65) Prior Publication Data

US 2022/0218521 A1 Jul. 14, 2022

Related U.S. Application Data

(60) Provisional application No. 63/236,598, filed on Aug. 24, 2021, provisional application No. 63/136,148, filed on Jan. 11, 2021.

(51) Int. Cl.
*A61F 9/00* (2006.01)
*A61F 9/007* (2006.01)

(52) U.S. Cl.
CPC ........ *A61F 9/0017* (2013.01); *A61F 9/00781* (2013.01)

(58) Field of Classification Search
CPC .. A61F 9/007; A61F 9/00736; A61F 9/00781; A61F 9/0017
See application file for complete search history.

(56) References Cited

U.S. PATENT DOCUMENTS

| 703,296 | A | 6/1902 | Arnold |
| 1,601,709 | A | 10/1926 | Windom |
| 2,716,983 | A | 9/1955 | George et al. |
| 3,071,135 | A | 1/1963 | Baldwin et al. |
| 3,788,327 | A | 1/1974 | Donowitz et al. |
| 3,811,442 | A | 5/1974 | Maroth |
| 3,858,577 | A | 1/1975 | Bass et al. |
| 3,884,236 | A | 5/1975 | Krasnov |
| 3,948,271 | A | 4/1976 | Akiyama |
| 3,982,541 | A | 9/1976 | L'Esperance |

(Continued)

FOREIGN PATENT DOCUMENTS

| AU | 1998/76197 B2 | 2/1999 |
| DE | 4226476 C1 | 8/1993 |

(Continued)

OTHER PUBLICATIONS

Bahler, et al.; Trabecular bypass stents decrease intraocular pressure in cultured human anterior segments; Amer. Journal of Ophthalmology; vol. 138, No. 6; pp. 988-994.e2; Dec. 2004.

(Continued)

*Primary Examiner* — Nathan R Price
*Assistant Examiner* — Anh Bui
(74) *Attorney, Agent, or Firm* — Levine Bagade Han LLP

(57) ABSTRACT

A method and device for reducing intraocular pressure in a patient. The method may comprise deploying administering a viscoelastic material into Schlemm's canal to open aqueous humor outflow pathways. The device is adapted to perform the method. The viscoelastic material may be configured to lower the intraocular pressure within the eye.

20 Claims, 28 Drawing Sheets

(56) References Cited

U.S. PATENT DOCUMENTS

| | | |
|---|---|---|
| 4,037,604 A | 7/1977 | Newkirk |
| 4,134,405 A | 1/1979 | Smit |
| 4,273,109 A | 6/1981 | Enderby |
| 4,391,275 A | 7/1983 | Fankhauser et al. |
| 4,428,746 A | 1/1984 | Mendez |
| 4,457,757 A | 7/1984 | Molteno |
| 4,461,294 A | 7/1984 | Baron |
| 4,470,407 A | 9/1984 | Hussein |
| 4,497,319 A | 2/1985 | Sekine et al. |
| 4,501,274 A | 2/1985 | Skjaerpe |
| 4,517,973 A | 5/1985 | Sunago et al. |
| 4,538,608 A | 9/1985 | L'Esperance |
| 4,548,205 A | 10/1985 | Armeniades et al. |
| 4,551,129 A | 11/1985 | Coleman |
| 4,558,698 A | 12/1985 | O'Dell |
| 4,559,942 A | 12/1985 | Eisenberg |
| 4,566,438 A | 1/1986 | Liese et al. |
| 4,580,559 A | 4/1986 | L'Esperance |
| 4,583,539 A | 4/1986 | Karlin et al. |
| 4,601,713 A | 7/1986 | Fuquo |
| 4,604,087 A | 8/1986 | Joseph |
| 4,633,866 A | 1/1987 | Peyman et al. |
| 4,658,816 A | 4/1987 | Ector |
| 4,660,546 A | 4/1987 | Herrick et al. |
| 4,671,273 A | 6/1987 | Lindsey |
| 4,689,040 A | 8/1987 | Thompson |
| 4,699,140 A | 10/1987 | Holmes et al. |
| 4,706,669 A | 11/1987 | Schlegel |
| 4,722,350 A | 2/1988 | Armeniades et al. |
| 4,722,724 A | 2/1988 | Schocket |
| 4,729,373 A | 3/1988 | Peyman |
| 4,733,665 A | 3/1988 | Palmaz |
| 4,750,901 A | 6/1988 | Molteno |
| 4,770,654 A | 9/1988 | Rogers et al. |
| 4,791,927 A | 12/1988 | Menger |
| 4,826,478 A | 5/1989 | Schocket |
| 4,846,172 A | 7/1989 | Berlin |
| 4,861,341 A | 8/1989 | Woodburn |
| 4,876,250 A | 10/1989 | Clark |
| 4,880,000 A | 11/1989 | Holmes et al. |
| 4,886,488 A | 12/1989 | White |
| 4,919,130 A | 4/1990 | Stoy et al. |
| 4,925,299 A | 5/1990 | Meisberger et al. |
| 4,934,363 A | 6/1990 | Smith |
| 4,934,809 A | 6/1990 | Volk |
| 4,936,825 A | 6/1990 | Ungerleider |
| 4,946,436 A | 8/1990 | Smith |
| 4,968,296 A | 11/1990 | Ritch et al. |
| 4,994,060 A | 2/1991 | Rink et al. |
| 5,034,010 A | 7/1991 | Kittrell et al. |
| 5,092,837 A | 3/1992 | Ritch et al. |
| 5,123,902 A | 6/1992 | Mullet et al. |
| 5,127,901 A | 7/1992 | Odrich |
| 5,129,895 A | 7/1992 | Vassiliadis et al. |
| 5,178,604 A | 1/1993 | Baerveldt et al. |
| 5,180,362 A | 1/1993 | Worst |
| 5,190,552 A | 3/1993 | Kelman |
| 5,213,569 A | 5/1993 | Davis |
| 5,246,452 A | 9/1993 | Sinnott |
| 5,254,112 A | 10/1993 | Sinofsky et al. |
| 5,273,056 A | 12/1993 | McLaughlin |
| 5,290,267 A | 3/1994 | Zimmermann |
| 5,300,020 A | 4/1994 | L'Esperance |
| 5,359,685 A | 10/1994 | Waynant et al. |
| 5,360,399 A | 11/1994 | Stegmann |
| 5,371,078 A | 12/1994 | Clark et al. |
| 5,372,577 A | 12/1994 | Ungerleider |
| 5,445,637 A | 8/1995 | Bretton |
| 5,454,796 A | 10/1995 | Krupin |
| 5,458,615 A | 10/1995 | Klemm et al. |
| 5,501,274 A | 3/1996 | Nguyen et al. |
| 5,536,259 A | 7/1996 | Utterberg |
| 5,575,780 A | 11/1996 | Saito |
| 5,591,223 A | 1/1997 | Lock et al. |
| 5,607,966 A | 3/1997 | Hellberg et al. |
| 5,613,972 A | 3/1997 | Lee et al. |
| 5,626,558 A | 5/1997 | Suson |
| 5,643,250 A | 7/1997 | O'Donnell |
| 5,653,753 A | 8/1997 | Brady et al. |
| 5,657,760 A | 8/1997 | Ying et al. |
| 5,676,669 A | 10/1997 | Colvard |
| 5,704,907 A | 1/1998 | Nordquist et al. |
| 5,713,844 A | 2/1998 | Peyman |
| 5,722,970 A | 3/1998 | Colvard et al. |
| 5,738,676 A | 4/1998 | Hammer |
| 5,738,677 A | 4/1998 | Colvard et al. |
| 5,785,658 A | 7/1998 | Benaron et al. |
| 5,792,099 A | 8/1998 | DeCamp et al. |
| 5,792,103 A | 8/1998 | Schwartz et al. |
| 5,807,302 A | 9/1998 | Wandel |
| 5,811,453 A | 9/1998 | Yanni et al. |
| 5,865,831 A | 2/1999 | Cozean et al. |
| 5,868,697 A | 2/1999 | Richter et al. |
| 5,879,319 A | 3/1999 | Pynson et al. |
| 5,885,279 A | 3/1999 | Bretton |
| 5,893,837 A | 4/1999 | Eagles et al. |
| 5,895,831 A | 4/1999 | Brasier et al. |
| 5,919,171 A | 7/1999 | Kira et al. |
| 5,948,427 A | 9/1999 | Yamamoto et al. |
| 5,968,058 A | 10/1999 | Richter et al. |
| 5,990,099 A | 11/1999 | Clark |
| 5,993,438 A | 11/1999 | Juhasz et al. |
| 5,997,531 A | 12/1999 | Loeb et al. |
| 6,002,480 A | 12/1999 | Izatt et al. |
| 6,007,511 A | 12/1999 | Prywes |
| 6,050,970 A | 4/2000 | Baerveldt |
| 6,083,193 A | 7/2000 | Kadziauskas et al. |
| 6,099,521 A | 8/2000 | Shaddock |
| 6,102,045 A | 8/2000 | Nordquist et al. |
| 6,142,990 A | 11/2000 | Burk |
| 6,146,375 A | 11/2000 | Juhasz et al. |
| 6,177,544 B1 | 1/2001 | Kanai et al. |
| 6,186,974 B1 | 2/2001 | Allan et al. |
| 6,217,584 B1 | 4/2001 | Nun |
| 6,221,078 B1 | 4/2001 | Bylsma |
| 6,238,409 B1 | 5/2001 | Hojeibane |
| 6,241,721 B1 | 6/2001 | Cozean et al. |
| D444,874 S | 7/2001 | Haffner et al. |
| 6,297,228 B1 | 10/2001 | Clark |
| 6,319,274 B1 | 11/2001 | Shadduck |
| 6,328,747 B1 | 12/2001 | Nun |
| 6,375,642 B1 | 4/2002 | Grieshaber et al. |
| 6,398,809 B1 | 6/2002 | Hoffmann et al. |
| 6,409,752 B1 | 6/2002 | Boatman et al. |
| 6,450,984 B1 | 9/2002 | Lynch et al. |
| 6,464,724 B1 | 10/2002 | Lynch et al. |
| 6,471,666 B1 | 10/2002 | Odrich |
| 6,494,857 B1 | 12/2002 | Neuhann |
| 6,508,779 B1 | 1/2003 | Suson |
| 6,517,523 B1 | 2/2003 | Kaneko et al. |
| 6,524,275 B1 | 2/2003 | Lynch et al. |
| 6,533,764 B1 | 3/2003 | Haffner et al. |
| 6,533,768 B1 | 3/2003 | Hill |
| 6,544,208 B2 | 4/2003 | Ethier et al. |
| 6,544,249 B1 | 4/2003 | Yu et al. |
| 6,551,289 B1 | 4/2003 | Higuchi et al. |
| 6,626,858 B2 | 9/2003 | Lynch et al. |
| 6,638,239 B1 | 10/2003 | Bergheim et al. |
| 6,666,841 B2 | 12/2003 | Gharib et al. |
| 6,699,210 B2 | 3/2004 | Williams et al. |
| 6,699,211 B2 | 3/2004 | Savage |
| 6,702,790 B1 | 3/2004 | Ross |
| 6,726,676 B2 | 4/2004 | Stegmann et al. |
| D490,152 S | 5/2004 | Myall et al. |
| 6,730,056 B1 | 5/2004 | Ghaem et al. |
| 6,736,791 B1 | 5/2004 | Tu et al. |
| 6,780,164 B2 | 8/2004 | Bergheim et al. |
| 6,783,544 B2 | 8/2004 | Lynch et al. |
| 6,827,699 B2 | 12/2004 | Lynch et al. |
| 6,827,700 B2 | 12/2004 | Lynch et al. |
| 6,881,198 B2 | 4/2005 | Brown |
| 6,899,717 B2 | 5/2005 | Weber et al. |
| 6,939,298 B2 | 9/2005 | Brown et al. |
| 6,955,656 B2 | 10/2005 | Bergheim et al. |

(56) References Cited

U.S. PATENT DOCUMENTS

| | | |
|---|---|---|
| 6,962,573 B1 | 11/2005 | Wilcox |
| 6,981,958 B1 | 1/2006 | Gharib et al. |
| 6,989,007 B2 | 1/2006 | Shadduck |
| 7,018,376 B2 | 3/2006 | Webb et al. |
| 7,094,225 B2 | 8/2006 | Tu et al. |
| 7,125,119 B2 | 10/2006 | Farberov |
| 7,133,137 B2 | 11/2006 | Shimmick |
| 7,135,009 B2 | 11/2006 | Tu et al. |
| 7,147,650 B2 | 12/2006 | Lee |
| 7,163,543 B2 | 1/2007 | Smedley et al. |
| 7,186,232 B1 | 3/2007 | Smedley et al. |
| 7,192,412 B1 | 3/2007 | Zhou et al. |
| 7,207,965 B2 | 4/2007 | Simon |
| 7,207,980 B2 | 4/2007 | Christian et al. |
| 7,220,238 B2 | 5/2007 | Lynch et al. |
| 7,273,475 B2 | 9/2007 | Tu et al. |
| 7,297,130 B2 | 11/2007 | Bergheim et al. |
| 7,331,984 B2 | 2/2008 | Tu et al. |
| 7,488,303 B1 | 2/2009 | Haffner et al. |
| 7,699,882 B2 | 4/2010 | Stamper et al. |
| 7,740,604 B2 | 6/2010 | Schieber et al. |
| 7,931,596 B2 | 4/2011 | Rachlin et al. |
| 7,967,772 B2 | 6/2011 | McKenzie et al. |
| 8,012,115 B2 | 9/2011 | Karageozian |
| 8,123,729 B2 | 2/2012 | Yamamoto et al. |
| 8,172,899 B2 | 5/2012 | Silvestrini et al. |
| 8,267,882 B2 | 9/2012 | Euteneuer et al. |
| 8,282,592 B2 | 10/2012 | Schieber et al. |
| 8,308,701 B2 | 11/2012 | Horvath et al. |
| 8,337,509 B2 | 12/2012 | Schieber et al. |
| 8,372,026 B2 | 2/2013 | Schieber et al. |
| 8,414,518 B2 | 4/2013 | Schieber et al. |
| 8,425,449 B2 | 4/2013 | Wardle et al. |
| 8,475,374 B2 | 7/2013 | Irazoqui et al. |
| 8,512,404 B2 | 8/2013 | Frion et al. |
| 8,529,494 B2 | 9/2013 | Euteneuer et al. |
| 8,540,659 B2 | 9/2013 | Berlin |
| 8,551,166 B2 | 10/2013 | Schieber et al. |
| 8,629,161 B2 | 1/2014 | Mizuno et al. |
| 8,636,647 B2 | 1/2014 | Silvestrini et al. |
| 8,647,659 B2 | 2/2014 | Robinson et al. |
| 8,657,776 B2 | 2/2014 | Wardle et al. |
| 8,663,150 B2 | 3/2014 | Wardle et al. |
| 8,663,303 B2 | 3/2014 | Horvath et al. |
| 8,734,377 B2 | 5/2014 | Schieber et al. |
| 8,808,222 B2 | 8/2014 | Schieber et al. |
| 8,939,906 B2 | 1/2015 | Huang et al. |
| 8,939,948 B2 | 1/2015 | De Juan, Jr. et al. |
| 8,945,038 B2 | 2/2015 | Yablonski |
| 8,951,221 B2 | 2/2015 | Stegmann et al. |
| 8,961,447 B2 | 2/2015 | Schieber et al. |
| 8,974,511 B2 | 3/2015 | Horvath et al. |
| 9,039,650 B2 | 5/2015 | Schieber et al. |
| 9,050,169 B2 | 6/2015 | Schieber et al. |
| 9,066,750 B2 | 6/2015 | Wardle et al. |
| 9,066,783 B2 | 6/2015 | Euteneuer et al. |
| 9,155,655 B2 | 10/2015 | Wardle et al. |
| 9,211,213 B2 | 12/2015 | Wardle et al. |
| 9,226,852 B2 | 1/2016 | Schieber et al. |
| 9,301,875 B2 | 4/2016 | Tu et al. |
| 9,351,874 B2 | 5/2016 | Schieber et al. |
| 9,358,156 B2 | 6/2016 | Wardle et al. |
| 9,402,767 B2 | 8/2016 | Schieber et al. |
| 9,510,973 B2 | 12/2016 | Wardle |
| 9,579,234 B2 | 2/2017 | Wardle et al. |
| 9,603,741 B2 | 3/2017 | Berlin |
| 9,610,196 B2 | 4/2017 | Schieber et al. |
| 9,636,254 B2 | 5/2017 | Yu et al. |
| 9,642,746 B2 | 5/2017 | Berlin |
| 9,693,899 B2 | 7/2017 | Wardle et al. |
| 9,693,901 B2 | 7/2017 | Horvath et al. |
| 9,693,902 B2 | 7/2017 | Euteneuer et al. |
| 9,730,638 B2 | 8/2017 | Haffner et al. |
| 9,757,276 B2 | 9/2017 | Penhasi |
| 9,775,729 B2 | 10/2017 | McClain et al. |
| 9,782,293 B2 | 10/2017 | Doci |
| 9,788,999 B2 | 10/2017 | Schaller |
| 9,795,503 B2 | 10/2017 | Perez Grossmann |
| 9,808,373 B2 | 11/2017 | Horvath et al. |
| 9,820,883 B2 | 11/2017 | Berlin |
| 9,833,357 B2 | 12/2017 | Berlin |
| 9,931,243 B2 | 4/2018 | Wardle et al. |
| 10,159,601 B2 | 12/2018 | Berlin |
| 10,335,314 B2 | 7/2019 | Berlin |
| 10,363,168 B2 | 7/2019 | Schieber et al. |
| 10,390,993 B1 | 8/2019 | Berlin |
| 10,406,025 B2 | 9/2019 | Wardle et al. |
| 10,492,949 B2 | 12/2019 | Wardle et al. |
| 10,537,474 B2 | 1/2020 | Euteneuer et al. |
| 10,617,558 B2 | 4/2020 | Schieber et al. |
| 10,687,978 B2 | 6/2020 | Berlin |
| 10,709,547 B2 | 7/2020 | Schieber |
| 11,026,836 B2 | 6/2021 | Wardle et al. |
| 11,135,088 B2 | 10/2021 | Wardle et al. |
| 11,197,779 B2 | 12/2021 | Van Meter et al. |
| 2001/0002438 A1 | 5/2001 | Sepetka et al. |
| 2002/0003546 A1 | 1/2002 | Mochimaru et al. |
| 2002/0013546 A1 | 1/2002 | Grieshaber et al. |
| 2002/0013572 A1 | 1/2002 | Berlin |
| 2002/0052653 A1 | 5/2002 | Durgin |
| 2002/0072673 A1 | 6/2002 | Yamamoto et al. |
| 2002/0082591 A1 | 6/2002 | Haefliger |
| 2002/0133168 A1 | 9/2002 | Smedley et al. |
| 2002/0143284 A1 | 10/2002 | Tu et al. |
| 2002/0165504 A1 | 11/2002 | Sharp et al. |
| 2002/0165522 A1 | 11/2002 | Holmen |
| 2002/0193805 A1 | 12/2002 | Ott et al. |
| 2003/0004457 A1 | 1/2003 | Andersson |
| 2003/0014092 A1 | 1/2003 | Neuhann |
| 2003/0040754 A1 | 2/2003 | Mitchell et al. |
| 2003/0055372 A1 | 3/2003 | Lynch et al. |
| 2003/0060748 A1 | 3/2003 | Baikoff |
| 2003/0060752 A1 | 3/2003 | Bergheim et al. |
| 2003/0060784 A1 | 3/2003 | Hilgers et al. |
| 2003/0093084 A1 | 5/2003 | Nissan et al. |
| 2003/0097151 A1 | 5/2003 | Smedley et al. |
| 2003/0105456 A1 | 6/2003 | Lin |
| 2003/0125351 A1 | 7/2003 | Azuma et al. |
| 2003/0175324 A1 | 9/2003 | Robinson et al. |
| 2003/0181848 A1 | 9/2003 | Bergheim et al. |
| 2003/0187384 A1 | 10/2003 | Bergheim et al. |
| 2003/0212387 A1 | 11/2003 | Kurtz et al. |
| 2003/0229303 A1 | 12/2003 | Haffner et al. |
| 2003/0236483 A1 | 12/2003 | Ren |
| 2003/0236484 A1 | 12/2003 | Lynch et al. |
| 2004/0024345 A1 | 2/2004 | Gharib et al. |
| 2004/0024453 A1 | 2/2004 | Castillejos |
| 2004/0030302 A1 | 2/2004 | Kamata et al. |
| 2004/0070761 A1 | 4/2004 | Horvath et al. |
| 2004/0082939 A1 | 4/2004 | Berlin |
| 2004/0088048 A1 | 5/2004 | Richter et al. |
| 2004/0092856 A1 | 5/2004 | Dahan |
| 2004/0098124 A1 | 5/2004 | Freeman et al. |
| 2004/0102729 A1 | 5/2004 | Haffner et al. |
| 2004/0106975 A1 | 6/2004 | Solovay et al. |
| 2004/0111050 A1 | 6/2004 | Smedley et al. |
| 2004/0116909 A1 | 6/2004 | Neuberger et al. |
| 2004/0122380 A1 | 6/2004 | Utterberg |
| 2004/0127843 A1 | 7/2004 | Tu et al. |
| 2004/0147870 A1 | 7/2004 | Burns et al. |
| 2004/0193095 A1 | 9/2004 | Shaddock |
| 2004/0193262 A1 | 9/2004 | Shadduck |
| 2004/0199149 A1 | 10/2004 | Myers et al. |
| 2004/0199171 A1 | 10/2004 | Akahoshi |
| 2004/0210181 A1 | 10/2004 | Vass et al. |
| 2004/0210185 A1 | 10/2004 | Tu et al. |
| 2004/0216749 A1 | 11/2004 | Tu |
| 2004/0225357 A1 | 11/2004 | Worst et al. |
| 2004/0228013 A1 | 11/2004 | Goldstein et al. |
| 2004/0249333 A1 | 12/2004 | Bergheim et al. |
| 2004/0254517 A1 | 12/2004 | Quiroz-Mercado et al. |
| 2004/0254519 A1 | 12/2004 | Tu et al. |
| 2004/0254520 A1 | 12/2004 | Porteous et al. |
| 2004/0260228 A1 | 12/2004 | Lynch et al. |

(56) References Cited

U.S. PATENT DOCUMENTS

| | | |
|---|---|---|
| 2005/0041200 A1 | 2/2005 | Rich |
| 2005/0043722 A1 | 2/2005 | Lin |
| 2005/0049578 A1 | 3/2005 | Tu et al. |
| 2005/0090806 A1 | 4/2005 | Lynch et al. |
| 2005/0090807 A1 | 4/2005 | Lynch et al. |
| 2005/0101967 A1 | 5/2005 | Weber et al. |
| 2005/0107734 A1 | 5/2005 | Coroneo |
| 2005/0119636 A1 | 6/2005 | Haffner et al. |
| 2005/0119661 A1 | 6/2005 | Lynch et al. |
| 2005/0125003 A1 | 6/2005 | Pinchuk et al. |
| 2005/0131514 A1 | 6/2005 | Hijlkema et al. |
| 2005/0149114 A1 | 7/2005 | Cartledge et al. |
| 2005/0154443 A1 | 7/2005 | Linder et al. |
| 2005/0165385 A1 | 7/2005 | Simon |
| 2005/0192527 A1 | 9/2005 | Gharib et al. |
| 2005/0197667 A1 | 9/2005 | Chan et al. |
| 2005/0203542 A1 | 9/2005 | Weber et al. |
| 2005/0209549 A1 | 9/2005 | Bergheim et al. |
| 2005/0209550 A1 | 9/2005 | Bergheim et al. |
| 2005/0240168 A1 | 10/2005 | Neuberger et al. |
| 2005/0244464 A1 | 11/2005 | Hughes |
| 2005/0245916 A1 | 11/2005 | Connor |
| 2005/0250788 A1 | 11/2005 | Tu et al. |
| 2005/0260186 A1 | 11/2005 | Bookbinder et al. |
| 2005/0266047 A1 | 12/2005 | Tu et al. |
| 2005/0271704 A1 | 12/2005 | Tu et al. |
| 2005/0273033 A1 | 12/2005 | Grahn et al. |
| 2005/0277864 A1 | 12/2005 | Haffner et al. |
| 2005/0279369 A1 | 12/2005 | Lin |
| 2005/0288619 A1 | 12/2005 | Gharib et al. |
| 2005/0288745 A1 | 12/2005 | Andersen et al. |
| 2006/0020247 A1 | 1/2006 | Kagan et al. |
| 2006/0021623 A1 | 2/2006 | Miller et al. |
| 2006/0032507 A1 | 2/2006 | Tu |
| 2006/0052879 A1 | 3/2006 | Kolb |
| 2006/0069340 A1 | 3/2006 | Simon |
| 2006/0074375 A1 | 4/2006 | Bergheim et al. |
| 2006/0079828 A1 | 4/2006 | Brown |
| 2006/0084907 A1 | 4/2006 | Bergheim et al. |
| 2006/0084954 A1 | 4/2006 | Zadoyan et al. |
| 2006/0106370 A1 | 5/2006 | Baerveldt et al. |
| 2006/0110428 A1 | 5/2006 | deJuan et al. |
| 2006/0116626 A1 | 6/2006 | Smedley et al. |
| 2006/0129141 A1 | 6/2006 | Lin |
| 2006/0149194 A1 | 7/2006 | Conston et al. |
| 2006/0154981 A1 | 7/2006 | Klimko et al. |
| 2006/0155238 A1 | 7/2006 | Shields |
| 2006/0155265 A1 | 7/2006 | Juhasz et al. |
| 2006/0155300 A1 | 7/2006 | Stamper et al. |
| 2006/0167421 A1 | 7/2006 | Quinn |
| 2006/0167466 A1 | 7/2006 | Dusek |
| 2006/0173397 A1 | 8/2006 | Tu et al. |
| 2006/0173399 A1 | 8/2006 | Rodgers et al. |
| 2006/0178674 A1 | 8/2006 | McIntyre |
| 2006/0189915 A1 | 8/2006 | Camras et al. |
| 2006/0189916 A1 | 8/2006 | Bas et al. |
| 2006/0189917 A1 | 8/2006 | Mayr et al. |
| 2006/0195055 A1 | 8/2006 | Bergheim et al. |
| 2006/0195056 A1 | 8/2006 | Bergheim et al. |
| 2006/0195187 A1 | 8/2006 | Stegmann et al. |
| 2006/0200113 A1 | 9/2006 | Haffner et al. |
| 2006/0224146 A1 | 10/2006 | Lin |
| 2006/0241749 A1 | 10/2006 | Tu et al. |
| 2006/0259021 A1 | 11/2006 | Lin |
| 2006/0264971 A1 | 11/2006 | Akahoshi |
| 2006/0276759 A1 | 12/2006 | Kinast et al. |
| 2007/0010827 A1 | 1/2007 | Tu et al. |
| 2007/0021725 A1 | 1/2007 | Villette |
| 2007/0027452 A1 | 2/2007 | Varner et al. |
| 2007/0073275 A1 | 3/2007 | Conston et al. |
| 2007/0088432 A1 | 4/2007 | Solovay et al. |
| 2007/0093794 A1 | 4/2007 | Wang et al. |
| 2007/0093796 A1 | 4/2007 | Raksi et al. |
| 2007/0106200 A1 | 5/2007 | Levy |
| 2007/0106236 A1 | 5/2007 | Coroneo |
| 2007/0112292 A1 | 5/2007 | Tu et al. |
| 2007/0118147 A1 | 5/2007 | Smedley et al. |
| 2007/0121120 A1 | 5/2007 | Schachar |
| 2007/0135681 A1 | 6/2007 | Chin et al. |
| 2007/0173791 A1 | 7/2007 | Raksi |
| 2007/0179520 A1 | 8/2007 | West |
| 2007/0191863 A1 | 8/2007 | De Juan, Jr. et al. |
| 2007/0202186 A1 | 8/2007 | Yamamoto |
| 2007/0208325 A1 | 9/2007 | Kurtz |
| 2007/0219509 A1 | 9/2007 | Tashiro et al. |
| 2007/0219541 A1 | 9/2007 | Kurtz |
| 2007/0235543 A1 | 10/2007 | Zadoyan et al. |
| 2007/0236771 A1 | 10/2007 | Zadoyan et al. |
| 2007/0265582 A1 | 11/2007 | Kaplan et al. |
| 2007/0270945 A1 | 11/2007 | Kobayashi et al. |
| 2007/0276315 A1 | 11/2007 | Haffner et al. |
| 2007/0276316 A1 | 11/2007 | Haffner et al. |
| 2007/0282244 A1 | 12/2007 | Tu et al. |
| 2007/0282245 A1 | 12/2007 | Tu et al. |
| 2007/0293807 A1 | 12/2007 | Lynch et al. |
| 2007/0293872 A1 | 12/2007 | Peyman |
| 2007/0298068 A1 | 12/2007 | Badawi et al. |
| 2008/0015488 A1 | 1/2008 | Tu et al. |
| 2008/0027519 A1 | 1/2008 | Guerrero |
| 2008/0045878 A1 | 2/2008 | Bergheim et al. |
| 2008/0058704 A1 | 3/2008 | Hee et al. |
| 2008/0058777 A1 | 3/2008 | Kurtz et al. |
| 2008/0082088 A1 | 4/2008 | Kurtz et al. |
| 2008/0091224 A1 | 4/2008 | Griffis et al. |
| 2008/0119827 A1 | 5/2008 | Kurtz et al. |
| 2008/0228127 A1 | 9/2008 | Burns et al. |
| 2008/0278687 A1 | 11/2008 | Somani |
| 2008/0288082 A1 | 11/2008 | Deal |
| 2008/0312661 A1 | 12/2008 | Downer et al. |
| 2009/0005852 A1 | 1/2009 | Gittings et al. |
| 2009/0028953 A1 | 1/2009 | Yamamoto et al. |
| 2009/0030363 A1 | 1/2009 | Gellman |
| 2009/0030381 A1 | 1/2009 | Lind et al. |
| 2009/0036843 A1 | 2/2009 | Erskine |
| 2009/0043321 A1 | 2/2009 | Conston et al. |
| 2009/0054723 A1 | 2/2009 | Khairkhahan et al. |
| 2009/0069786 A1 | 3/2009 | Vesely et al. |
| 2009/0082862 A1 | 3/2009 | Schieber et al. |
| 2009/0104248 A1 | 4/2009 | Rapacki et al. |
| 2009/0118716 A1 | 5/2009 | Brownell |
| 2009/0118717 A1 | 5/2009 | Brownell et al. |
| 2009/0118718 A1 | 5/2009 | Raksi et al. |
| 2009/0131921 A1 | 5/2009 | Kurtz et al. |
| 2009/0137988 A1 | 5/2009 | Kurtz |
| 2009/0138081 A1 | 5/2009 | Bergheim et al. |
| 2009/0157062 A1 | 6/2009 | Hauger et al. |
| 2009/0171327 A1 | 7/2009 | Kurtz et al. |
| 2009/0182421 A1 | 7/2009 | Silvestrini et al. |
| 2009/0198248 A1 | 8/2009 | Yeung et al. |
| 2009/0204053 A1 | 8/2009 | Nissan et al. |
| 2009/0247955 A1 | 10/2009 | Yamamoto et al. |
| 2009/0259126 A1 | 10/2009 | Saal et al. |
| 2009/0281520 A1 | 11/2009 | Highley et al. |
| 2009/0281530 A1 | 11/2009 | Korn |
| 2009/0291423 A1 | 11/2009 | Hara |
| 2010/0004580 A1 | 1/2010 | Lynch et al. |
| 2010/0036488 A1 | 2/2010 | de Juan et al. |
| 2010/0057072 A1 | 3/2010 | Roman et al. |
| 2010/0114309 A1 | 5/2010 | de Juan et al. |
| 2010/0137981 A1 | 6/2010 | Silvestrini et al. |
| 2010/0173866 A1 | 7/2010 | Hee et al. |
| 2010/0191176 A1 | 7/2010 | Ho et al. |
| 2010/0191177 A1 | 7/2010 | Chang et al. |
| 2010/0234726 A1 | 9/2010 | Sirimanne et al. |
| 2010/0234790 A1 | 9/2010 | Tu et al. |
| 2010/0262174 A1 | 10/2010 | Sretavan et al. |
| 2010/0324543 A1 | 12/2010 | Kurtz et al. |
| 2010/0331858 A1 | 12/2010 | Simaan et al. |
| 2011/0028948 A1 | 2/2011 | Raksi et al. |
| 2011/0028949 A1 | 2/2011 | Raksi et al. |
| 2011/0028950 A1 | 2/2011 | Raksi et al. |
| 2011/0028951 A1 | 2/2011 | Raksi et al. |
| 2011/0028952 A1 | 2/2011 | Raksi et al. |
| 2011/0028953 A1 | 2/2011 | Raksi et al. |

(56) References Cited

U.S. PATENT DOCUMENTS

| | | |
|---|---|---|
| 2011/0028954 A1 | 2/2011 | Raksi et al. |
| 2011/0028955 A1 | 2/2011 | Raksi |
| 2011/0028957 A1 | 2/2011 | Raksi et al. |
| 2011/0028958 A1 | 2/2011 | Raksi et al. |
| 2011/0098809 A1* | 4/2011 | Wardle ............... A61F 9/00781 623/6.12 |
| 2011/0196487 A1 | 8/2011 | Badawi et al. |
| 2011/0218523 A1 | 9/2011 | Robl |
| 2011/0224597 A1 | 9/2011 | Stegmann et al. |
| 2012/0010702 A1 | 1/2012 | Stegmann et al. |
| 2012/0021397 A1 | 1/2012 | Van Dalen et al. |
| 2012/0022424 A1 | 1/2012 | Yamamoto et al. |
| 2012/0035524 A1 | 2/2012 | Silvestrini |
| 2012/0191064 A1 | 7/2012 | Conston et al. |
| 2012/0271272 A1 | 10/2012 | Hammack et al. |
| 2012/0283557 A1 | 11/2012 | Berlin |
| 2012/0302861 A1 | 11/2012 | Marshall et al. |
| 2013/0023837 A1 | 1/2013 | Becker |
| 2013/0182223 A1 | 7/2013 | Wardle et al. |
| 2013/0184631 A1 | 7/2013 | Pinchuk |
| 2013/0253402 A1 | 9/2013 | Badawi et al. |
| 2013/0253403 A1 | 9/2013 | Badawi et al. |
| 2013/0253437 A1 | 9/2013 | Badawi et al. |
| 2013/0253438 A1 | 9/2013 | Badawi et al. |
| 2013/0253528 A1 | 9/2013 | Haffner et al. |
| 2013/0267887 A1 | 10/2013 | Kahook et al. |
| 2013/0281908 A1 | 10/2013 | Schaller et al. |
| 2014/0018720 A1 | 1/2014 | Horvath et al. |
| 2014/0066821 A1 | 3/2014 | Freidland et al. |
| 2014/0066831 A1 | 3/2014 | Silvestrini et al. |
| 2014/0081195 A1 | 3/2014 | Clauson et al. |
| 2014/0309599 A1* | 10/2014 | Schaller ............. A61M 5/31526 604/294 |
| 2015/0018746 A1 | 1/2015 | Hattenbach |
| 2015/0022780 A1 | 1/2015 | John et al. |
| 2015/0038893 A1 | 2/2015 | Haffner et al. |
| 2015/0045714 A1 | 2/2015 | Horvath et al. |
| 2015/0057583 A1 | 2/2015 | Gunn et al. |
| 2015/0057591 A1 | 2/2015 | Horvath et al. |
| 2015/0065940 A1 | 3/2015 | Rangel-Friedman et al. |
| 2015/0148836 A1 | 5/2015 | Heeren |
| 2015/0305939 A1 | 10/2015 | Vera et al. |
| 2015/0305940 A1 | 10/2015 | Vera et al. |
| 2015/0313759 A1 | 11/2015 | Vera et al. |
| 2016/0063898 A1 | 3/2016 | Bernal |
| 2017/0127941 A1 | 5/2017 | Ostermeier et al. |
| 2017/0143541 A1 | 5/2017 | Badawi et al. |
| 2017/0164831 A1 | 6/2017 | Choo et al. |
| 2017/0172794 A1 | 6/2017 | Varner et al. |
| 2017/0172795 A1 | 6/2017 | Lerner |
| 2017/0172797 A1 | 6/2017 | Horvath et al. |
| 2017/0172798 A1 | 6/2017 | Horvath et al. |
| 2017/0172799 A1 | 6/2017 | Horvath |
| 2017/0172800 A1 | 6/2017 | Romoda et al. |
| 2017/0202708 A1 | 7/2017 | Berlin |
| 2017/0239272 A1 | 8/2017 | Ambati et al. |
| 2017/0251921 A1 | 9/2017 | Phan et al. |
| 2017/0252209 A1 | 9/2017 | Gooi |
| 2017/0280997 A1 | 10/2017 | Lai et al. |
| 2017/0281409 A1 | 10/2017 | Haffner et al. |
| 2017/0348150 A1 | 12/2017 | Horvath et al. |
| 2017/0360609 A9 | 12/2017 | Schieber et al. |
| 2018/0256395 A1* | 9/2018 | Escaf ................... A61M 3/0258 |
| 2018/0360655 A1 | 12/2018 | Berlin |
| 2018/0369017 A1 | 12/2018 | Schieber et al. |
| 2019/0142632 A1 | 5/2019 | Badawi et al. |
| 2019/0343679 A1 | 11/2019 | Wardle et al. |
| 2019/0380874 A1 | 12/2019 | Schieber et al. |
| 2020/0060876 A1 | 2/2020 | Wardle et al. |
| 2020/0085620 A1 | 3/2020 | Euteneuer et al. |
| 2020/0197221 A1 | 6/2020 | Schieber et al. |
| 2020/0222238 A1 | 7/2020 | Schieber et al. |
| 2020/0261266 A1* | 8/2020 | Bley .................... A61K 9/1611 |
| 2020/0261270 A1 | 8/2020 | Berlin |
| 2020/0305878 A1* | 10/2020 | Herrin ................. A61B 17/3478 |
| 2021/0030590 A1 | 2/2021 | Blanda et al. |
| 2021/0330499 A1 | 10/2021 | Wardle et al. |
| 2021/0361477 A1 | 11/2021 | Johnson et al. |
| 2021/0361479 A1 | 11/2021 | Wardle et al. |
| 2022/0054314 A1 | 2/2022 | Van Meter et al. |

FOREIGN PATENT DOCUMENTS

| | | |
|---|---|---|
| DE | 102012221350 A1 | 5/2014 |
| EP | 0168201 B1 | 6/1988 |
| EP | 0957949 A1 | 11/1996 |
| EP | 0766544 B1 | 5/1998 |
| EP | 1615604 B1 | 8/2009 |
| EP | 2193821 A1 | 6/2010 |
| EP | 1715827 B1 | 12/2010 |
| EP | 2380622 A1 | 10/2011 |
| EP | 2468327 A1 | 6/2012 |
| EP | 2471563 A1 | 7/2012 |
| EP | 1833440 B1 | 8/2012 |
| EP | 3164061 A1 | 5/2017 |
| EP | 2996648 B1 | 6/2017 |
| EP | 1732484 B1 | 8/2017 |
| EP | 1740153 B2 | 8/2017 |
| EP | 3076948 A4 | 8/2017 |
| EP | 3205333 A1 | 8/2017 |
| EP | 3060180 A4 | 9/2017 |
| EP | 3082570 A4 | 9/2017 |
| JP | 10504978 A | 5/1998 |
| JP | 11123205 A | 5/1999 |
| JP | 2002542872 A | 12/2002 |
| JP | 2006517848 A | 8/2006 |
| JP | 2006289075 A | 10/2006 |
| JP | 2009523545 A | 6/2009 |
| JP | 2010509003 A | 3/2010 |
| JP | 2011502649 A | 1/2011 |
| JP | 2012527318 A | 11/2012 |
| JP | 2015517836 A | 6/2015 |
| JP | 2017517363 A | 6/2017 |
| WO | WO96/20742 A1 | 7/1996 |
| WO | WO99/01063 A1 | 1/1999 |
| WO | WO99/45868 A1 | 9/1999 |
| WO | WO00/07525 A1 | 2/2000 |
| WO | WO00/64389 A1 | 11/2000 |
| WO | WO00/64393 A1 | 11/2000 |
| WO | WO00/67687 A1 | 11/2000 |
| WO | WO01/89437 A2 | 11/2001 |
| WO | WO01/97727 A1 | 12/2001 |
| WO | WO02/36052 A1 | 5/2002 |
| WO | WO02/074052 A2 | 9/2002 |
| WO | WO02/080811 A2 | 10/2002 |
| WO | WO03/01 5659 A2 | 2/2003 |
| WO | WO03/045290 A1 | 6/2003 |
| WO | WO2004/054643 A1 | 7/2004 |
| WO | WO2004/093761 A1 | 11/2004 |
| WO | WO2005/105197 A2 | 11/2005 |
| WO | WO2006/066103 A2 | 6/2006 |
| WO | WO2007/035356 A2 | 3/2007 |
| WO | WO2007/047744 A2 | 4/2007 |
| WO | WO2007/087061 A2 | 8/2007 |
| WO | WO2008/002377 A1 | 1/2008 |
| WO | WO2008/005873 A2 | 1/2008 |
| WO | WO2009/120960 A2 | 10/2009 |
| WO | WO2011/053512 A1 | 5/2011 |
| WO | WO2011/057283 A1 | 5/2011 |
| WO | WO2011/106781 A1 | 9/2011 |
| WO | WO2011/150045 A1 | 12/2011 |
| WO | WO2012/051575 A2 | 4/2012 |
| WO | WO2012/083143 A1 | 6/2012 |
| WO | WO2013/147978 A2 | 10/2013 |
| WO | WO2016/154066 A2 | 9/2016 |
| WO | WO2017/030902 A2 | 2/2017 |
| WO | WO2017/030917 A1 | 2/2017 |
| WO | WO2017/062347 A1 | 4/2017 |
| WO | WO2017/087713 A1 | 5/2017 |
| WO | WO2017/095825 A1 | 6/2017 |
| WO | WO2017/132418 A1 | 8/2017 |
| WO | WO2017/132647 A1 | 8/2017 |

(56) References Cited

FOREIGN PATENT DOCUMENTS

| WO | WO2017/156530 A1 | 9/2017 |
|----|------------------|--------|
| WO | WO2019/106803 A1 | 6/2019 |
| WO | WO2021/055751 A1 | 3/2021 |

OTHER PUBLICATIONS

Cambridge Dictionary: Sensor (definition); 2 pages; retrived from the internet (http://dictionary.cambridge.org/define.asp?dict=CALD&key=71811 >) on Aug. 14, 2018.

Camras et al.; A novel schlemm's canal scaffold increases outflow facility in a human anterior segment perfusion model; Invest. Opthalmol. Vis. Sci., 53(10); pp. 6115-6121; Sep. 1, 2012.

D'Ermo, et al.; Our results with the operation of ab externo trabeculotomy; Ophthalmologica; vol. 163; pp. 347-355; Feb. 1971.

Dietlein et al.; Morphological variability of the trabecular meshwork in glaucoma patients: implications for non-perforating glaucoma surgery; British Journal of Ophthalmology: 84(12); pp. 1354-1359; Dec. 2000.

Ellingsen et al.; Trabeculotomy and sinusotomy in enucleated human eyes; Investigative Ophthalmology; vol. 11; pp. 21-28; Jan. 1972.

Gallab et al.; Development of a spherical model with a 3D microchannel: An application to glaucoma surgery; Micromachines; 10(5):297; pp. 1-12; May 1, 2019.

Grant; Experimental aqueous perfusion in enucleated human eyes; Archives of Ophthalmology; vol. 69; pp. 783-801; Jun. 1963.

Gulati et al; A novel 8-mm schlemm's canal scaffold reduces outflow resistance in a human anterior segment perfusion model; Invest. Ophthalmol. Vis. Sci.; 54(3); pp. 1698-1704; Mar. 5, 2013.

Hays et al.; Improvement in outflow facility by two novel microinvasive glaucoma surgery implants; Invest. Ophthalmol. Vis. Sci.; 55(3); pp. 1893-1900; Mar. 1, 2014.

Huang et al.; Optical coherence tomography; Science; 254(5035); pp. 1178-1181; 12 pages (Author Manuscript); Nov. 1991.

Johnstone et al.; "Microsurgery of Schlemm's Canal and the Human Aqueous Outflow System;" American Journal of Ophthalmology, vol. 76 (6): 906-917; Dec. 1973.

Johnstone et al.; Effects of a schiemm canal scaffold on collector channel ostia in human anterior segments; Exp. Eye. Res.; 119; pp. 70-76; Feb. 2014.

Johnstone; Aqueous humor outflow system overview; Becker-Shaffer's Diagnosis and Therapy of the Glaucomas; Part 2 Aqueous Humor Dynamics; Chapter 3; pp. 25-46; Mosby Elseveir; 2009 (the year of publication is sufficiently earlier than the effective U.S. filing date and any foreign priority date so that the particular month of publication is not in issue).

Kirkness et al.; The Use of Silicone Drainage Tubing to Control Post-Keratoplasty Glaucoma; Eye; 2 (pt 5); pp. 583-590; Apr. 1988.

Lee et al.; Aqueous-venous shunt and intraocular pressure. Preliminary report of animal studies; Investigative Ophthalmology; vol. 5; No. 1; pp. 59-64; Feb. 1966.

Lee et al.; Short-pulsed neodymium-YAG laser trabeculotomy. An in vivo morphological study in the human eye; Investigative Ophthalmology and Visual Science; 29(11); pp. 1698-1707; Nov. 1988.

Lynch, Mary G.: U.S. Appl. No. 60/131,030 entitled "Devices and methods for treating glaucoma by enhancing aqueous outflow through schlemm's canal and anterior chamber angle," filed Apr. 26, 1999.

Macmilla Online Dictionary; Detector (definition); Macmilla on Line Dictionary; 2 pages; retrived from the internet (https://www.macmillandictionary.com/dictionary/british/detector) on Aug. 14, 2018.

Mäepea et al.; The pressures in the episcleral veins, schlemm's canal and the trabecular meshwork in monkeys: effects of changes in intraocular pressure; Exp. Eye Res.; vol. 49; pp. 645-663: Oct. 1989.

Molteno et al.; Long Tube Implants in the Management of Glaucoma; SA Medical Journal; 26: pp. 1062-1066; Jun. 1976.

Molteno; New implant for drainage in glaucoma; Brit. J. Ophthal; 53; pp. 606-615; Sep. 1969.

Moses, Robert; The effect of intraocular pressure on resistance to outflow; Survey of Ophthalmology; vol. 22; No. 2; pp. 88-100; Sep.-Oct. 1977.

Nakamura et al.; Femtosecond laser pholodisruption of primate trabecular meshwork: an ex vivo study; Investigative Ophthalmology and Visual Science; 50(3); pp. 1198-1204; Mar. 2009.

Owen; A moving-mirror gonioscope for retinal surgery; British Journal of Ophthalmology; 61(3); pp. 246-247; Mar. 1977.

Oxford Dictionaries; Detector (definition); 1 page; retrieved from the internet (https://en.oxforddictionaries.com/definition/detector) on Aug. 14, 2018.

Oxford Dictionaries; Sensor (definition); 1 page; retrieved from te internet (http://www.askoxford.com/concise_oed/sensor?>) on Aug. 14, 2018.

Radhakrishnan et al.; Real-time optical coherence tomography of the anterior segment at 1310 nm; Archives of Opthhalmology; 119(8); pp. 1179-1185; Aug. 2001.

Rosenquist et al.; Outflow resistance of enucleated human eyes at two different perfusion pressures and different extents of trabeculotomy; Current Eye Res.; vol. 8: No. 12; pp. 1233-1240; Dec. 1989.

Savage, James; Gonioscopy in the management of glaucoma; Am. Academy of Ophthalmology; Focal Points; vol. XXIV; No. 3; pp. 1-14; Mar. 2006.

Schocket et al.; Anterior Chamber tube Shunt to an Encircling Band in the Treatment of Neovascular Glaucoma and other Refractory Glaucomas; Ophthalmology; 92; pp. 553-562; Apr. 1985.

Schultz, Jared; Canaloplasty procedure shows promise for open-angle glaucoma in European study; Ocular Surgery News; vol. 34; Mar. 1, 2007.

Smit et al.; Effects of viscoelastic injection into schlemm's canal in primate and human eyes; J. Am. Academy of Ophthalmology; vol. 109; No. 4; pp. 786-792; Apr. 2002.

Spiegel et al.; Schlemm's canal implant: a new method to lower intraocular pressure in patients with POAG?; Ophthalmic Surgery and Lasers; vol. 30; No. 6; pp. 492-494; Jun. 1999.

Sugiyama et al.; Micro-Diaphragm Pressure Sensor; 1986 International Electron Devices Meeting; pp. 184-187; Dec. 7, 1986.

Toyran et al.; Femtosecond laser photodisruption of human trabecular meshwork: an in vitro study; Experimental Eye Research; 81(3); pp. 298-305; Sep. 2005.

Wilcox et al.; Hypothesis for Improving Accessory Filtration by Using Geometry; Journal of Glaucoma; 3; pp. 244-247; Fall 1994.

Yuan et al.; Mathematical modeling of outflow facility increase with trabecular meshwork bypass and schlemm canal dilation; J. Glaucoma; 10 pgs.; Mar. 24, 2015 (Epub ahead of print).

Wardle et al.; U.S. Appl. No. 17/548,212 entitled "Single operator device for delivering an ocular implant," filed Dec. 10, 2021.

\* cited by examiner

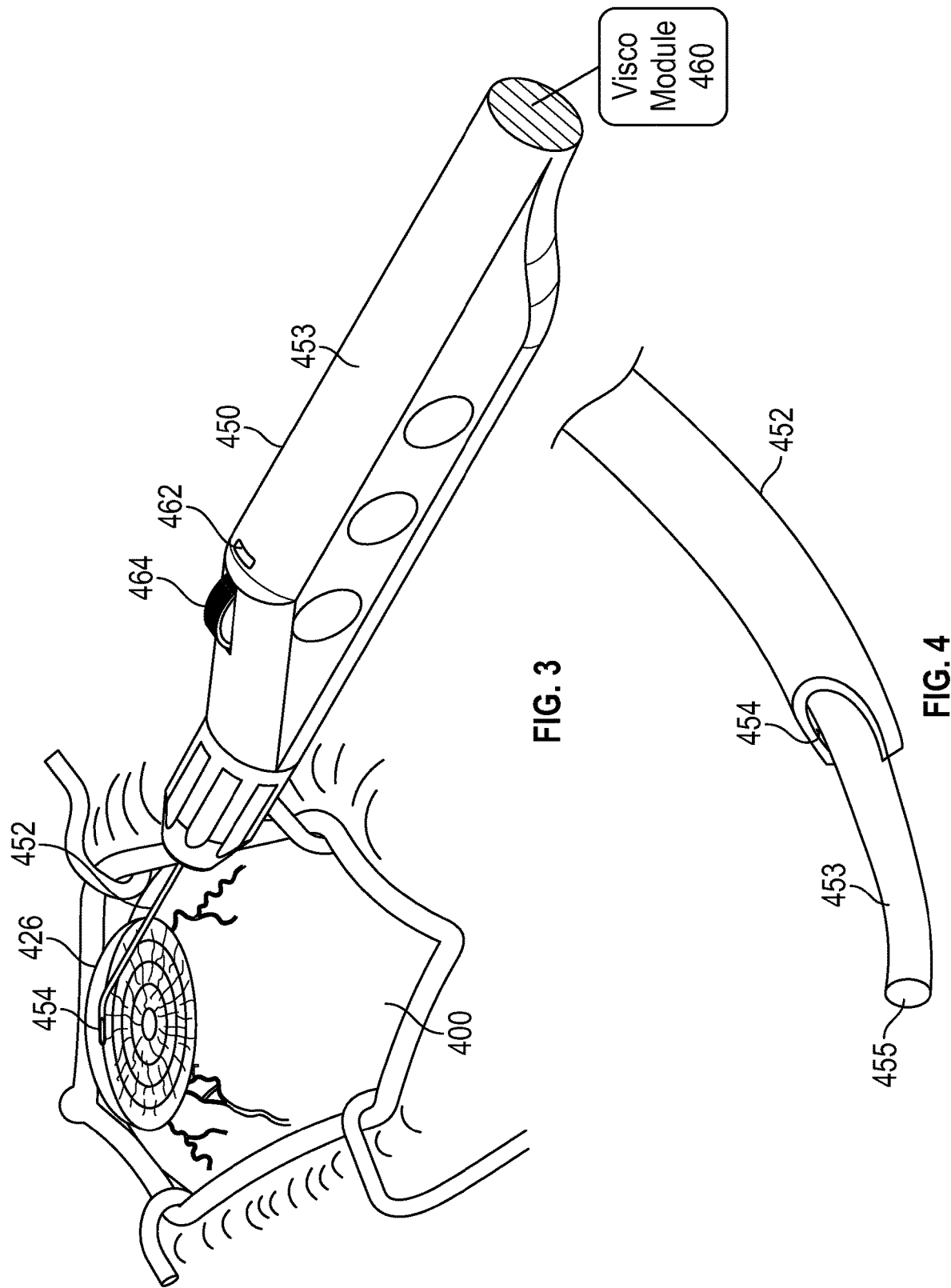

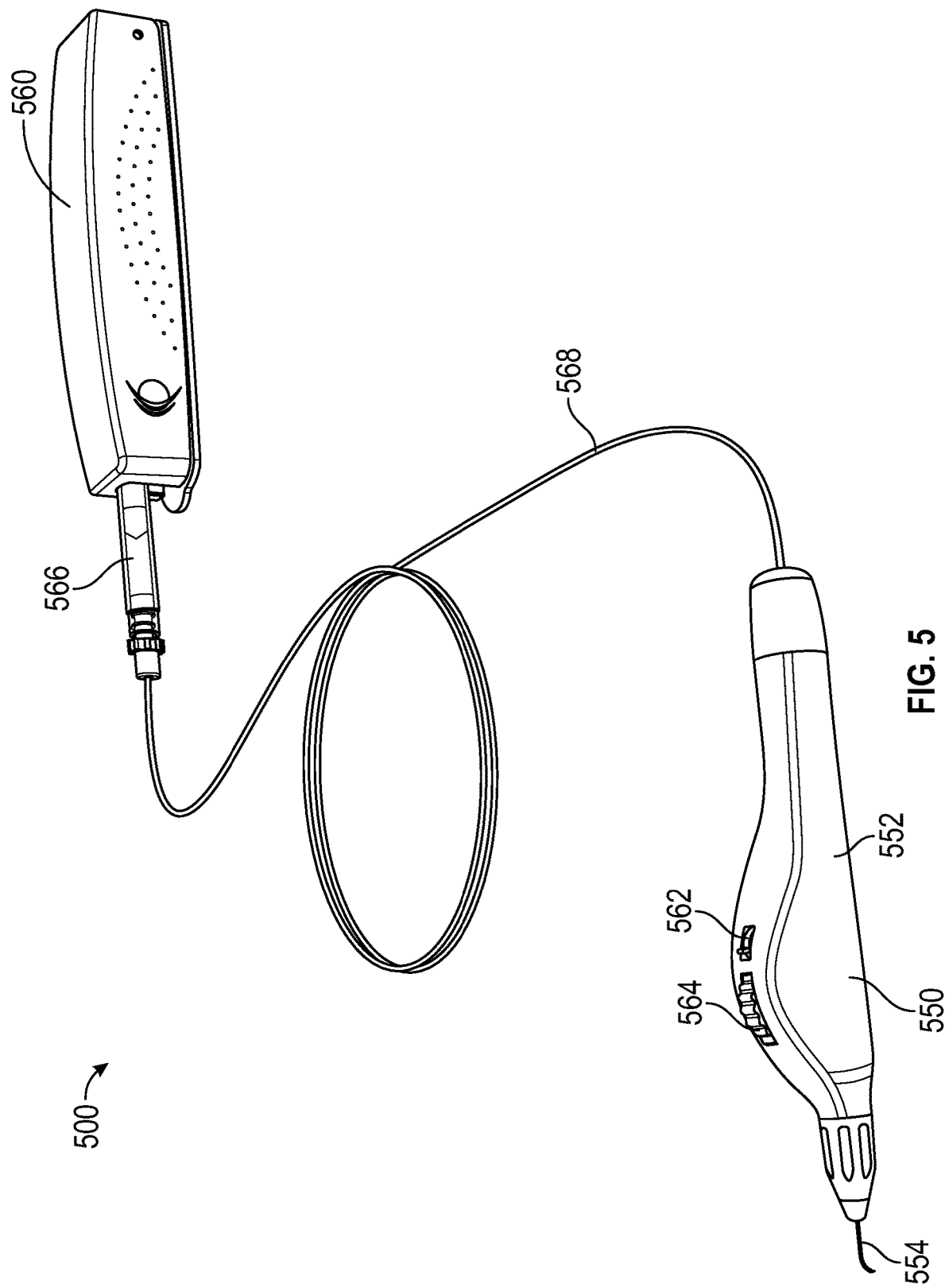

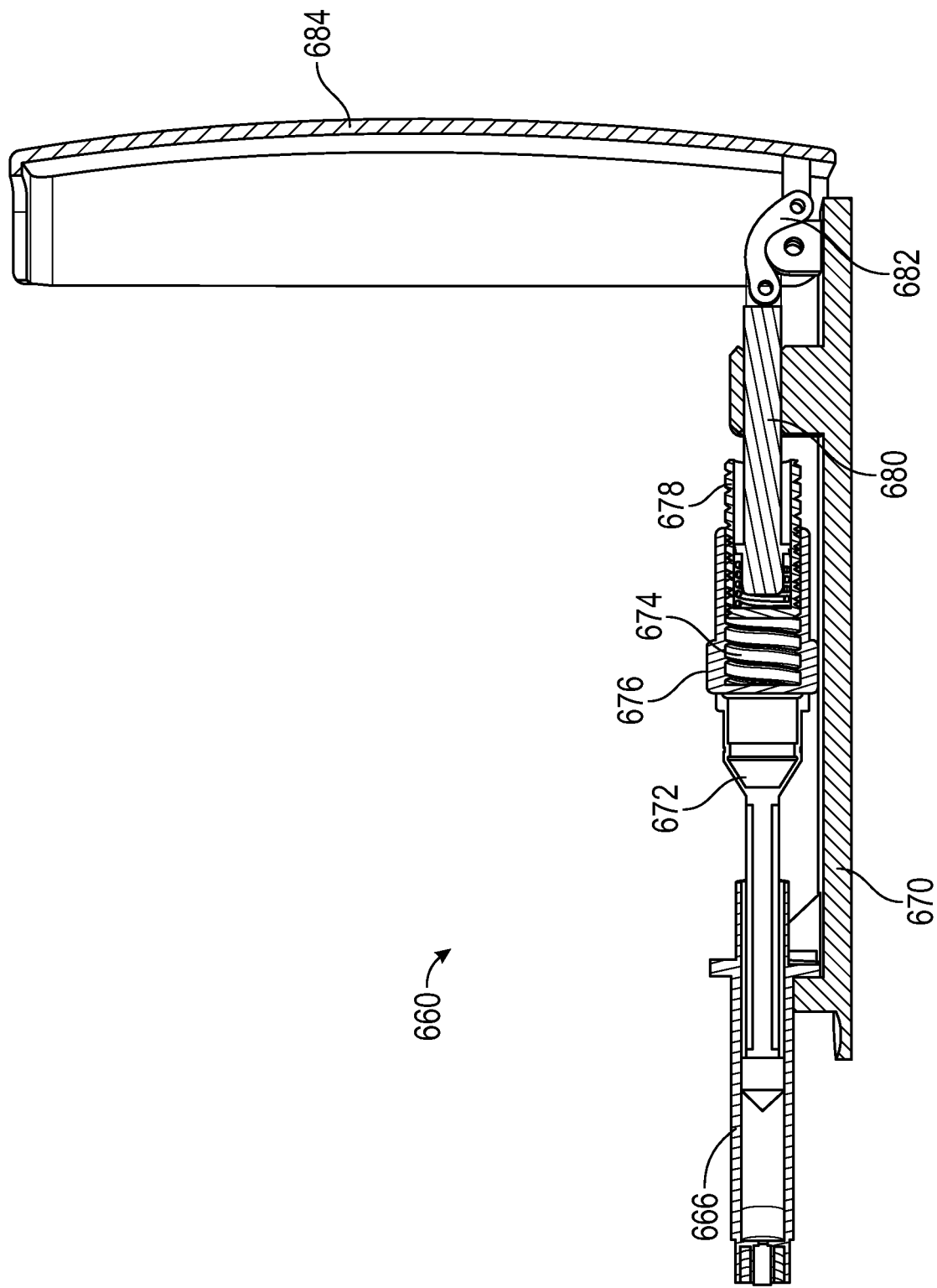

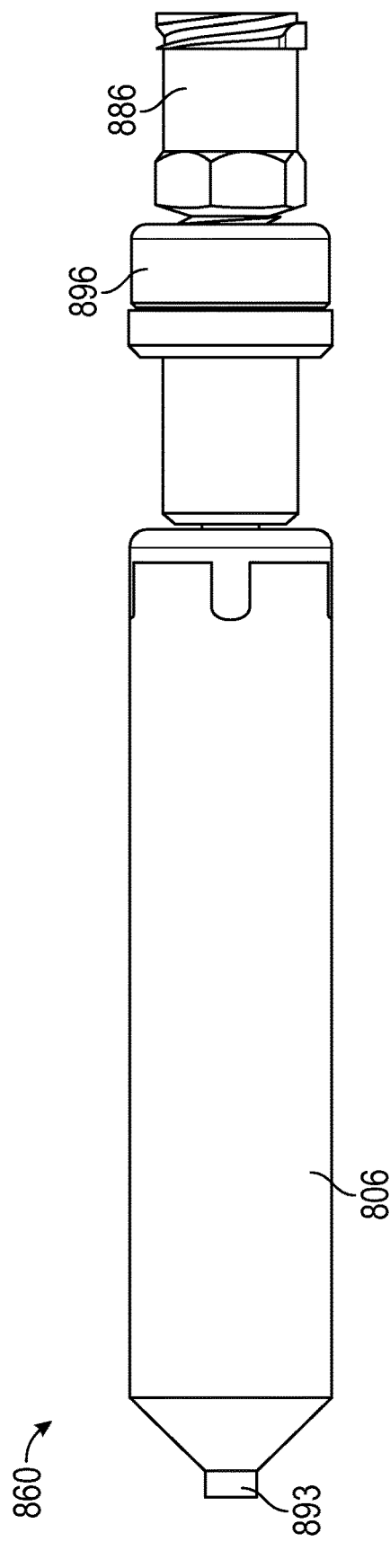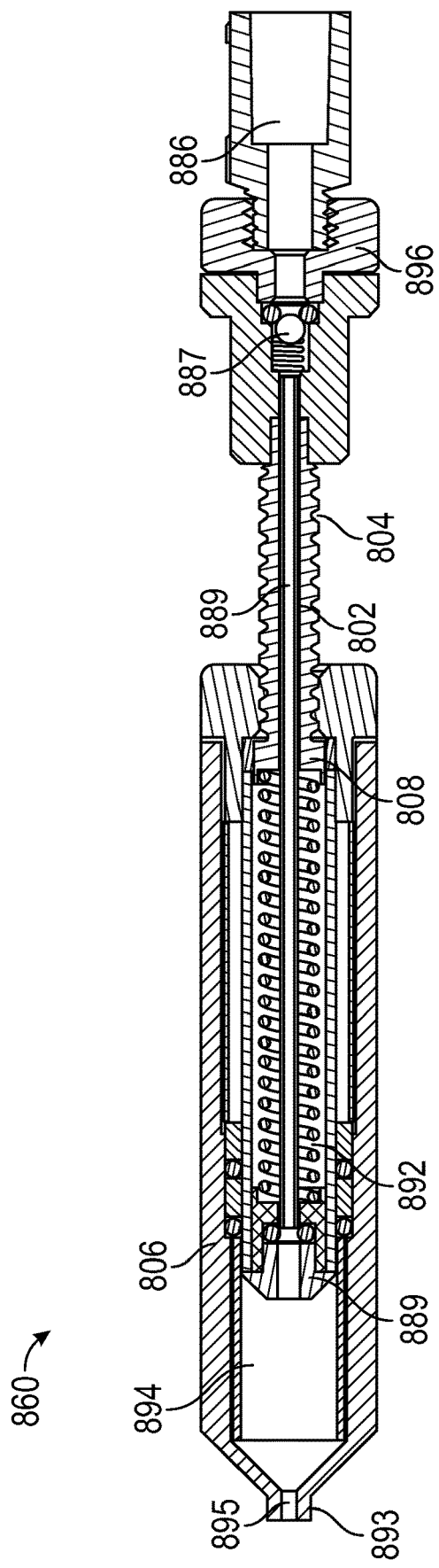

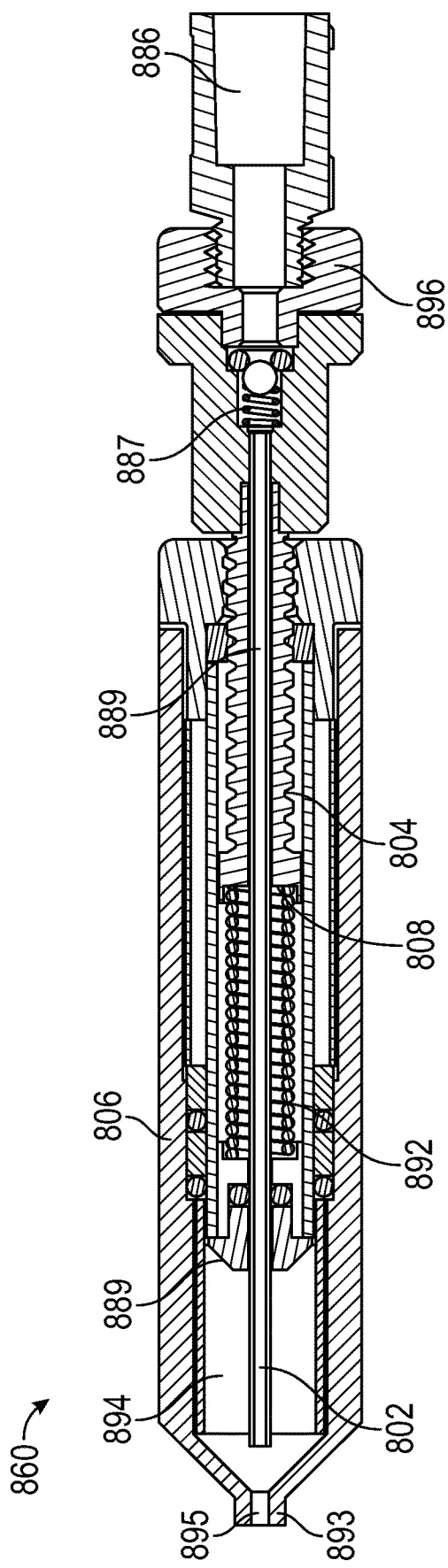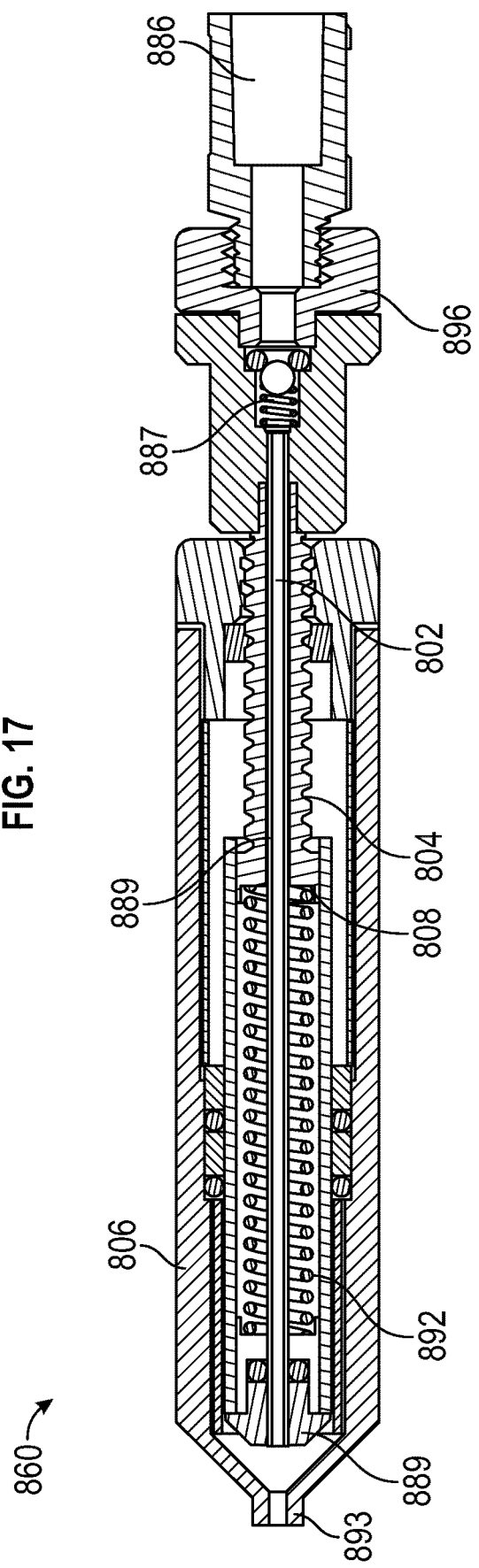
FIG. 17
FIG. 18

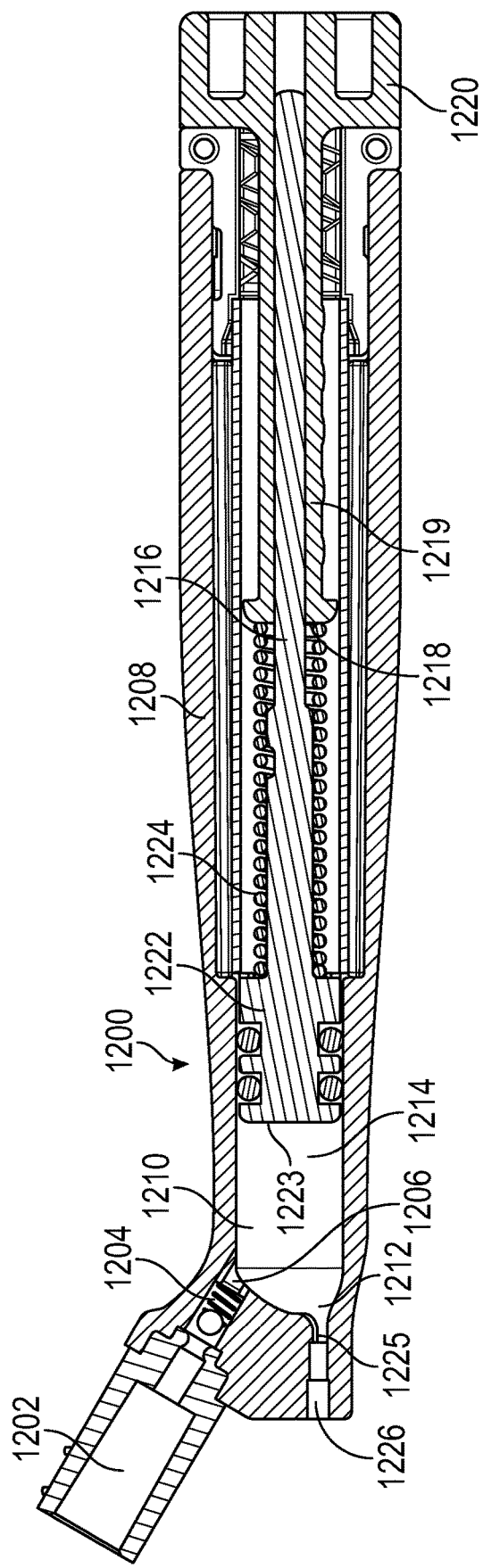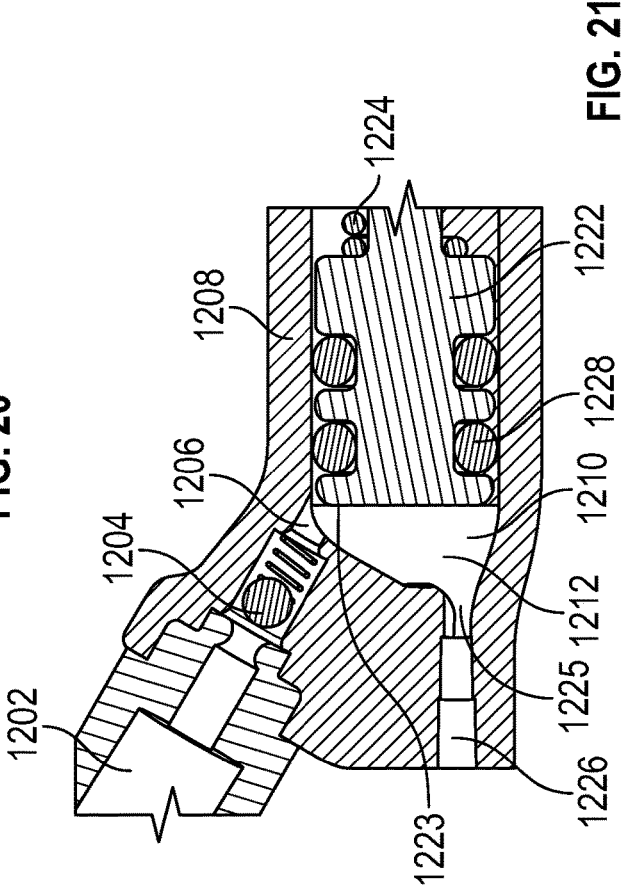

SYSTEMS AND METHODS FOR VISCOELASTIC DELIVERY

CROSS REFERENCE TO RELATED APPLICATIONS

This application claims the benefit of priority of U.S. Provisional Application No. 63/136,148, filed Jan. 11, 2021, and U.S. Provisional Application No. 63/236,598, filed Aug. 24, 2021, each of which is herein incorporated by reference in its entirety.

INCORPORATION BY REFERENCE

All publications and patent applications mentioned in this specification are herein incorporated by reference to the same extent as if each individual publication or patent application was specifically and individually indicated to be incorporated by reference.

TECHNICAL FIELD

The present disclosure pertains generally, but not by way of limitation, to medical devices, and methods for manufacturing medical devices. The present invention relates generally to devices and systems that are inserted into the eye. More particularly, the present invention relates to devices that facilitate the transfer of fluid from within one area of the eye to another area of the eye. Additionally, the present disclosure relates to systems, devices and methods for injecting a viscoelastic material into Schlemm's canal open aqueous humor outflow pathways.

BACKGROUND

According to a draft report by The National Eye Institute (NEI) at The United States National Institutes of Health (NIH), glaucoma is now the leading cause of irreversible blindness worldwide and the second leading cause of blindness, behind cataract, in the world. Thus, the NEI draft report concludes, "it is critical that significant emphasis and resources continue to be devoted to determining the pathophysiology and management of this disease." Glaucoma researchers have found a strong correlation between high intraocular pressure and glaucoma. For this reason, eye care professionals routinely screen patients for glaucoma by measuring intraocular pressure using a device known as a tonometer. Many modern tonometers make this measurement by blowing a sudden puff of air against the outer surface of the eye.

The eye can be conceptualized as a ball filled with fluid. There are two types of fluid inside the eye. The cavity behind the lens is filled with a viscous fluid known as vitreous humor. The cavities in front of the lens are filled with a fluid know as aqueous humor. Whenever a person views an object, he or she is viewing that object through both the vitreous humor and the aqueous humor.

Whenever a person views an object, he or she is also viewing that object through the cornea and the lens of the eye. In order to be transparent, the cornea and the lens can include no blood vessels. Accordingly, no blood flows through the cornea and the lens to provide nutrition to these tissues and to remove wastes from these tissues. Instead, these functions are performed by the aqueous humor. A continuous flow of aqueous humor through the eye provides nutrition to portions of the eye (e.g., the cornea and the lens) that have no blood vessels. This flow of aqueous humor also removes waste from these tissues.

Aqueous humor is produced by an organ known as the ciliary body. The ciliary body includes epithelial cells that continuously secrete aqueous humor. In a healthy eye, a stream of aqueous humor flows out of the anterior chamber of the eye through the trabecular meshwork and into Schlemm's canal as new aqueous humor is secreted by the epithelial cells of the ciliary body. This excess aqueous humor enters the venous blood stream from Schlemm's canal and is carried along with the venous blood leaving the eye.

When the natural drainage mechanisms of the eye stop functioning properly, the pressure inside the eye begins to rise. Researchers have theorized prolonged exposure to high intraocular pressure causes damage to the optic nerve that transmits sensory information from the eye to the brain. This damage to the optic nerve results in loss of peripheral vision. As glaucoma progresses, more and more of the visual field is lost until the patient is completely blind.

SUMMARY

The invention provides design, material, and methods of use for medical devices.

An illustrative method for reducing intraocular pressure in a patient may comprise administering a viscoelastic material into Schlemm's canal of an eye to open aqueous humor outflow pathways. In some embodiments, the viscoelastic can be administered prior to or after deploying an ocular implant into Schlemm's canal.

One aspect of the invention provides a method of treating an eye of a patient with an ocular system. In some embodiments, the method includes the steps of: inserting a distal end of a cannula of the ocular system into an anterior chamber of the eye; placing the cannula into fluid communication with Schlemm's canal, a conduit being disposed within the cannula; actuating a first control of the ocular system to advance the conduit from the cannula into Schlemm's canal; and actuating a second control of the ocular system to administer viscoelastic material from a viscoelastic delivery port of the conduit into Schlemm's canal without moving the conduit. In some embodiments, the method also includes the step of actuating the first control to retract the conduit within Schlemm's canal and into the cannula.

The method may include, in some embodiments, the step of pressurizing a volume of viscoelastic material within a viscoelastic module, wherein the step of actuating the second control comprises actuating the second control of the ocular system to administer viscoelastic material from the viscoelastic module into the conduit. In some such embodiments, the ocular system may have a handle, the cannula, the first control, and the second control each extending from, and supported by, the handle, with the viscoelastic module being disposed outside of the handle. In some embodiments, the step of pressurizing the volume of viscoelastic material may include the additional step of applying a spring to a plunger of a viscoelastic syringe disposed within the viscoelastic module.

In some embodiments, the step of pressurizing the volume of viscoelastic material includes the step of pressurizing a reservoir within the viscoelastic module. In some such embodiments, the step of pressurizing the reservoir includes the step of compressing a spring engaged with a wall of the reservoir, such as, e.g., by operating an actuator extending from the viscoelastic module.

Some embodiments include the additional step of filling the reservoir with viscoelastic material from a viscoelastic syringe. Some such embodiments include the additional step of advancing viscoelastic material from the viscoelastic syringe into the conduit, optionally before the step of filling the reservoir with viscoelastic material from the viscoelastic syringe.

Some embodiments have the additional step of providing tactile feedback while actuating the first control, the tactile feedback being correlated with a length of the conduit moving into or out of the cannula.

Some embodiments of the method also include the step of advancing an ocular implant into Schlemm's canal prior to the viscoelastic material being administered into Schlemm's canal. Some embodiments may also include the step of advancing an ocular implant into Schlemm's canal after the viscoelastic material is administered into Schlemm's canal.

Another aspect of the invention provides an ocular viscoelastic delivery system having a handle; a cannula defining a passageway extending from the handle to a distal cannula opening, the cannula being sized and configured to be advanced through an anterior chamber of a patient's eye to place the distal cannula opening in fluid communication with Schlemm's canal of the eye; a conduit slidably disposed within the cannula passageway, the conduit including a viscoelastic delivery port, at least a distal portion of the conduit being sized and configured to be advanced from the cannula into Schlemm's canal; a viscoelastic module in fluid communication with the conduit and the viscoelastic delivery port, the viscoelastic module being configured to contain a pressurized volume of viscoelastic material outside of the handle; a first control configured to adjust a position of the conduit and the viscoelastic delivery port relative to the cannula; and a second control configured to release pressurized viscoelastic material from the viscoelastic module through the conduit and viscoelastic delivery port into Schlemm's canal.

In some embodiments of the delivery system, the viscoelastic module also includes a cradle configured to receive a viscoelastic syringe and a force assembly configured to contact a plunger of the viscoelastic syringe, the force assembly being further configured to apply a constant force against the plunger. In some such embodiments, the force assembly also has an adjustment mechanism configured to adjust a position of the force assembly with respect to the plunger.

In some embodiments, the viscoelastic module force assembly has a reservoir and a spring configured to pressurize viscoelastic material in the reservoir. Some such embodiments also have an actuator extending from the viscoelastic module and configured to compress the spring to pressurize the reservoir.

In some embodiments, the viscoelastic module further has an inlet port adapted to engage with a viscoelastic syringe, the inlet port being fluid being fluidly communicable with the reservoir. In some such embodiments, the viscoelastic module also has a check valve disposed between the inlet port and the reservoir, the check valve being configured to open to permit pressurized viscoelastic material to flow from the viscoelastic syringe through the inlet port to the reservoir and to close to prevent viscoelastic material from the reservoir out of the inlet port.

In some embodiments, the first control and the second control are disposed on the handle. In some embodiments, a single actuation of the first control moves the conduit by a known distance, and in some embodiments a single actuation of the second control administers a known volume of viscoelastic material from the conduit and viscoelastic delivery port into Schlemm's canal. Some embodiments provide a cantilever spring engaged with the first control and adapted to provide tactile feedback of movement of the first control.

In some embodiments, the second control includes a toggle lever operable to be moved to a first position to open a valve to deliver viscoelastic material from the viscoelastic module into the conduit, the second control further comprising a spring operable to move the toggle to a second position to close the valve. Some such embodiments also have a toggle lock configured to hold the toggle lever in the first position. The toggle lock may be removably disposed on an exterior surface of the handle and engaged with the toggle lever.

In some embodiments, the delivery system also has tubing extending from the viscoelastic module to the handle, the tubing having a fluid lumen extending from an outlet of the viscoelastic module to an inlet control in the handle. The tubing may have a length of 3-4 inches.

Yet another aspect of the invention provides an ocular delivery system including a handle; a hub disposed at a distal end of the handle and being configured to be rotatable with respect to the handle; a cannula coupled to the hub and configured to be rotated with the hub, the cannula defining a passageway extending from the handle to a distal cannula opening, the cannula being sized and configured to be advanced through an anterior chamber of a patient's eye to place the distal cannula opening in fluid communication with Schlemm's canal of the eye, the cannula having a curved distal end; a cannula orientation marking rotatable with the hub and visible from outside of the delivery system, the marking being aligned with a radial direction in which the cannula curved distal end extends; and a stationary marking supported by the handle, the cannula orientation marking and the stationary marking together indicating an orientation of the cannula curved distal end with respect to an orientation of the handle.

In some embodiments, the system also has a conduit slidably disposed within the cannula passageway, the conduit including a viscoelastic delivery port, at least a distal portion of the conduit being sized and configured to be advanced from the cannula into Schlemm's canal, and a reservoir adapted to deliver viscoelastic material into the conduit. In some such embodiments, the system has a control configured to adjust a position of the conduit and the viscoelastic delivery port relative to the cannula. In some embodiments, the system has a control configured to release pressurized viscoelastic material from the reservoir through the conduit and viscoelastic delivery port into Schlemm's canal.

The above summary of some examples and embodiments is not intended to describe each disclosed embodiment or every implementation of the present disclosure. The Brief Description of the Drawings, and Detailed Description, which follow, more particularly exemplify these embodiments, but are also intended as exemplary and not limiting.

BRIEF DESCRIPTION OF THE DRAWINGS

The disclosure may be more completely understood in consideration of the following detailed description of various embodiments in connection with the accompanying drawings, in which:

FIG. 3 is an enlarged perspective view further illustrating a delivery system and the eye of a patient.

FIG. 4 illustrates one example of a cannula of the delivery system including a conduit and a viscoelastic delivery port.

FIG. 5 is a perspective view illustrating one embodiment of a viscoelastic delivery system.

FIG. 6 is a partial cross-section and partial side elevational view illustrating a viscoelastic module of the viscoelastic delivery system in an open, unpressurized configuration.

FIG. 15 is a side elevational view of yet another embodiment of a viscoelastic module of the viscoelastic delivery system.

FIG. 16 is a cross-sectional view of the viscoelastic module of FIG. 15 in a pre-filling configuration.

FIG. 17 is a cross-sectional view of the viscoelastic module of FIGS. 15-16 in a filled and pressurized configuration.

FIG. 18 is a cross-sectional view of the viscoelastic module of FIGS. 15-17 in an empty configuration.

FIG. 20 is a cross-sectional view showing still another embodiment of a viscoelastic module of the viscoelastic delivery system.

FIG. 21 is a cross-sectional view showing details of the viscoelastic module of FIG. 20.

Figure 1:
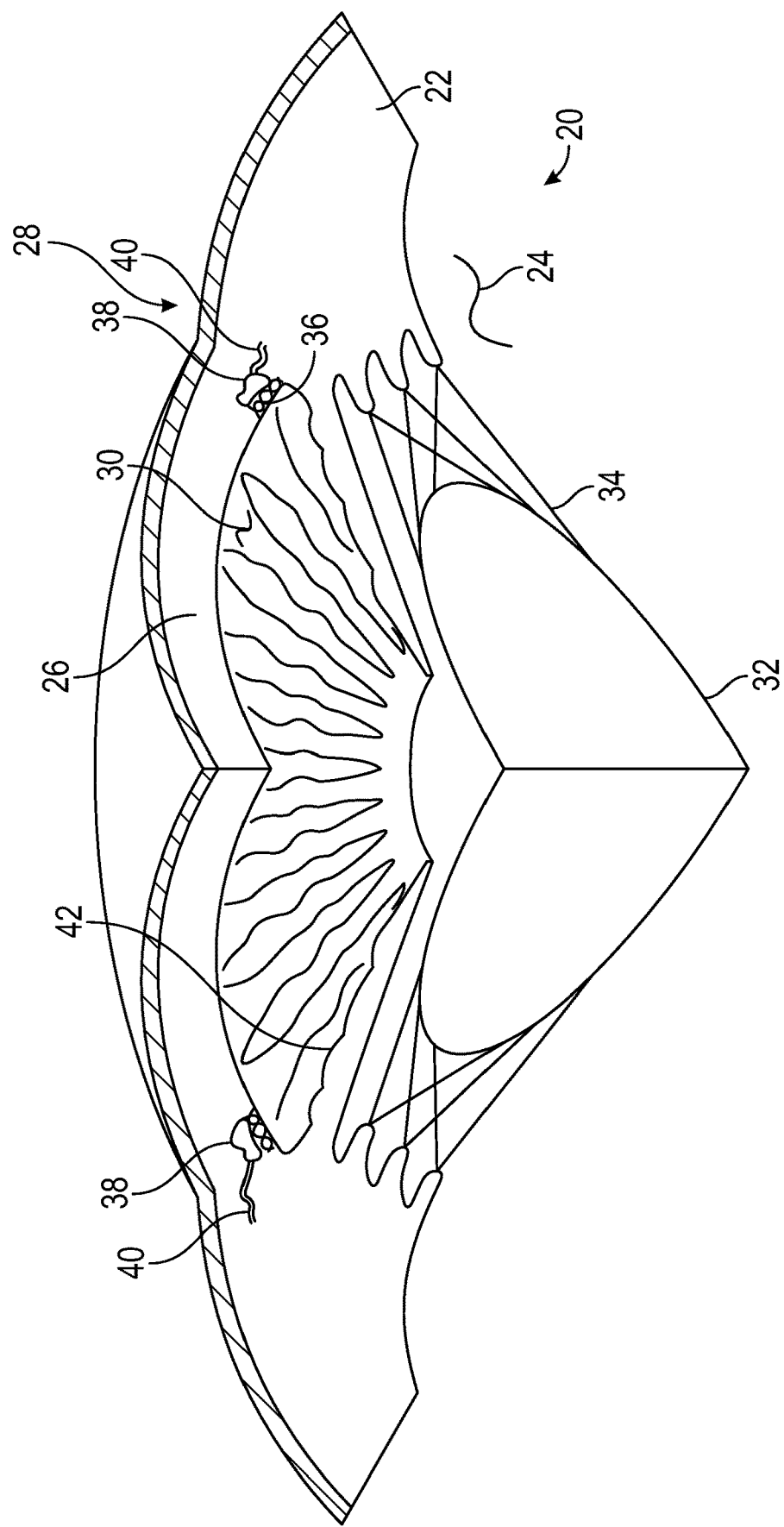
FIG. 1 is a stylized perspective view depicting a portion of a human eye and a portion of an ocular implant disposed in Schlemm's canal.

While the disclosure is amenable to various modifications and alternative forms, specifics thereof have been shown by way of example in the drawings and will be described in detail. It should be understood, however, that the intention is not to limit the invention to the particular embodiments described. On the contrary, the intention is to cover all modifications, equivalents, and alternatives falling within the spirit and scope of the disclosure.

DETAILED DESCRIPTION

The following description should be read with reference to the drawings, which are not necessarily to scale, wherein like reference numerals indicate like elements throughout the several views. The detailed description and drawings are intended to illustrate but not limit the claimed invention. Those skilled in the art will recognize that the various elements described and/or shown may be arranged in various combinations and configurations without departing from the scope of the disclosure. The detailed description and drawings illustrate example embodiments of the claimed invention.

Definitions of certain terms are provided below and shall be applied, unless a different definition is given in the claims or elsewhere in this specification.

All numeric values are herein assumed to be modified by the term "about," whether or not explicitly indicated. The term "about" generally refers to a range of numbers that one of skill in the art would consider equivalent to the recited value (i.e., having the same or substantially the same function or result). In many instances, the terms "about" may include numbers that are rounded to the nearest significant figure. Other uses of the term "about" (i.e., in a context other than numeric values) may be assumed to have their ordinary and customary definition(s), as understood from and consistent with the context of the specification, unless otherwise specified.

The recitation of numerical ranges by endpoints includes all numbers within that range (e.g., 1 to 5 includes 1, 1.5, 2, 2.75, 3, 3.80, 4, and 5).

As used in this specification and the appended claims, the singular forms "a," "an," and "the" include or otherwise refer to singular as well as plural referents, unless the content clearly dictates otherwise. As used in this specification and the appended claims, the term "or" is generally employed to include "and/or," unless the content clearly dictates otherwise.

It is noted that references in the specification to "an embodiment", "some embodiments", "other embodiments", etc., indicate that the embodiment(s) described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it would be within the knowledge of one skilled in the art to affect such feature, structure, or characteristic in connection with other embodiments, whether or not explicitly described, unless clearly stated to the contrary. That is, the various individual elements described below, even if not explicitly shown in a particular combination, are nevertheless contemplated as being combinable or able to be arranged with each other to form other additional embodiments or to complement and/or enrich the described embodiment(s), as would be understood by one of ordinary skill in the art.

The following detailed description should be read with reference to the drawings, in which similar elements in different drawings are identified with the same reference numbers. The drawings, which are not necessarily to scale, depict illustrative embodiments and are not intended to limit the scope of the disclosure.

FIG. 1 is a stylized perspective view depicting a portion of a human eye 20. Eye 20 can be conceptualized as a fluid filled ball having two chambers. Sclera 22 of eye 20 surrounds a posterior chamber 24 filled with a viscous fluid known as vitreous humor. Cornea 26 of eye 20 encloses an anterior chamber 30 that is filled with a fluid know as aqueous humor. The cornea 26 meets the sclera 22 at a limbus 28 of eye 20. A lens 32 of eye 20 is located between anterior chamber 30 and posterior chamber 24. Lens 32 is held in place by a number of ciliary zonules 34. Whenever a person views an object, he or she is viewing that object through the cornea, the aqueous humor, and the lens of the eye. In order to be transparent, the cornea and the lens can include no blood vessels. Accordingly, no blood flows through the cornea and the lens to provide nutrition to these tissues and to remove wastes from these tissues. Instead, these functions are performed by the aqueous humor. A continuous flow of aqueous humor through the eye provides nutrition to portions of the eye (e.g., the cornea and the lens) that have no blood vessels. This flow of aqueous humor also removes waste from these tissues.

Aqueous humor is produced by an organ known as the ciliary body. The ciliary body includes epithelial cells that continuously secrete aqueous humor. In a healthy eye, a stream of aqueous humor flows out of the eye as new aqueous humor is secreted by the epithelial cells of the ciliary body. This excess aqueous humor enters the blood stream and is carried away by venous blood leaving the eye.

In a healthy eye, aqueous humor flows out of the anterior chamber 30 through the trabecular meshwork 36 and into Schlemm's canal 38, located at the outer edge of the iris 42. Aqueous humor exits Schlemm's canal 38 by flowing through a number of outlets 40. After leaving Schlemm's canal 38, aqueous humor is absorbed into the venous blood stream.

Figure 2:
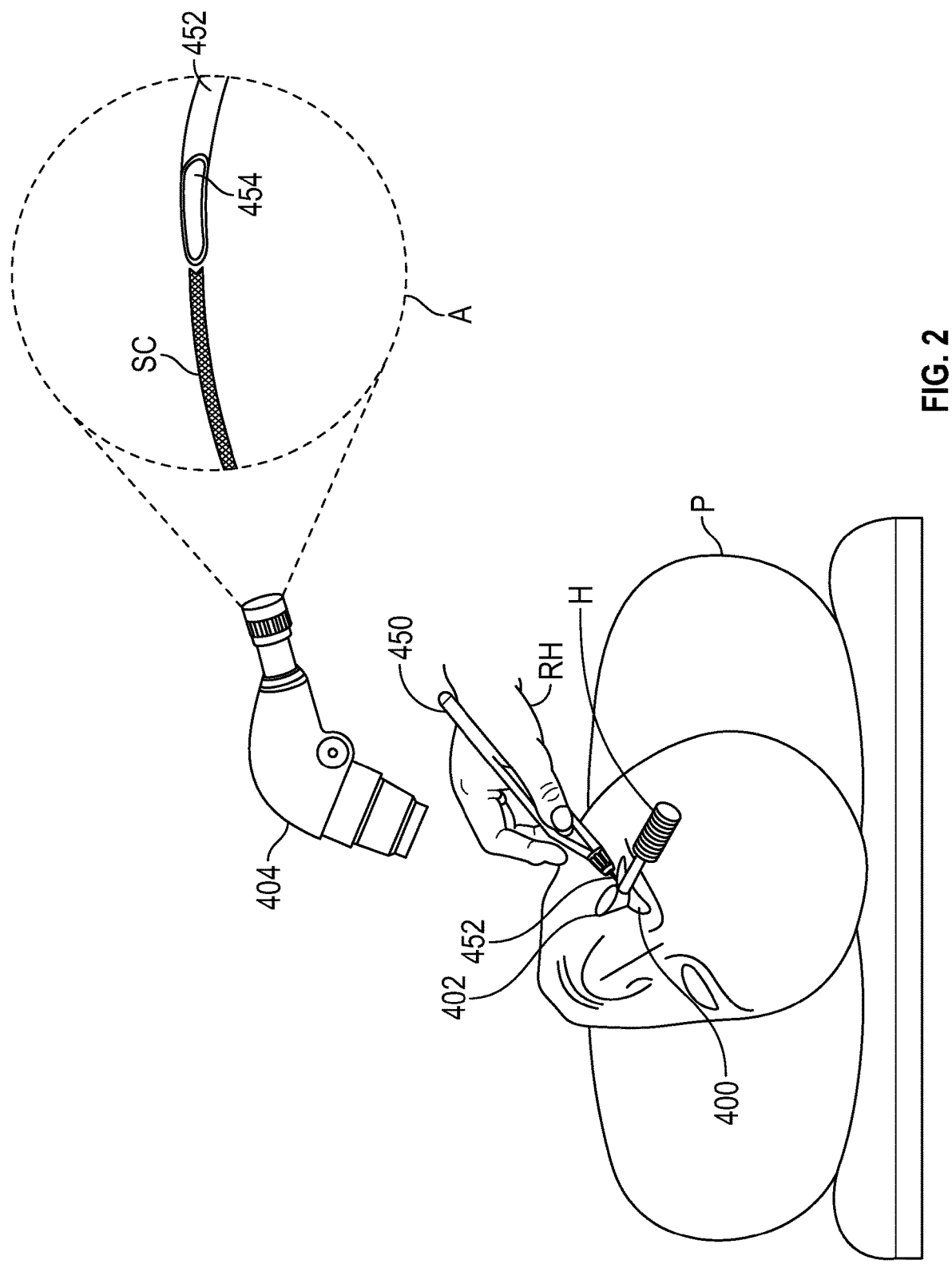
FIG. 2 is a stylized representation of a medical procedure in accordance with this disclosure.

FIG. 2 is a stylized representation of a medical procedure in accordance with this detailed description. In the procedure of FIG. 2, a physician is treating an eye 400 of a patient P. In the procedure of FIG. 2, the physician is holding a hand piece of a viscoelastic delivery system 450 in his or her right hand RH. The physician's left hand (not shown) may be used to hold the handle H of a gonio lens 402. Alternatively, some physicians may prefer holding the delivery system hand piece in the left hand and the gonio lens handle H in the right hand RH.

During the procedure illustrated in FIG. 2, the physician may view the interior of the anterior chamber using gonio lens 402 and a microscope 404. Detail A of FIG. 2 is a stylized simulation of the image viewed by the physician. A distal portion of a cannula 452 is visible in Detail A. A shadow-like line indicates the location of Schlemm's canal SC which is lying under various tissues (e.g., the trabecular meshwork) that surround the anterior chamber. A distal opening 454 of cannula 452 is positioned near Schlemm's canal SC of eye 400.

Methods in accordance with this detailed description may include the step of advancing the distal end of cannula 452 through the cornea of eye 400 so that a distal portion of cannula 452 is disposed in the anterior chamber of the eye. Cannula 452 may then be used to access Schlemm's canal of the eye, for example, by piercing the wall of Schlemm's canal with the distal end of cannula 452. Distal opening 454 of cannula 452 may be placed in fluid communication with a lumen defined by Schlemm's canal. A viscoelastic material may be administered from the cannula into Schlemm's canal to open aqueous humor outflow pathways. Delivery of a viscoelastic material into Schlemm's canal may facilitate the flow of aqueous humor out of the anterior chamber of the eye.

FIG. 3 is an enlarged perspective view further illustrating viscoelastic delivery system 450 and eye 400 shown in the previous figure. In FIG. 3, cannula 452 extending from a handle 453 of viscoelastic delivery system 450 is shown extending through a cornea 426 of eye 400. A distal portion of cannula 452 is disposed inside the anterior chamber defined by cornea 426 of eye 400. In the embodiment of FIG. 3, cannula 452 is configured so that a distal opening 454 of cannula 452 can be placed in fluid communication with Schlemm's canal.

In the embodiment of FIG. 3, a viscoelastic material can be administered by the cannula into Schlemm's canal. In some embodiments, a conduit or microcatheter can be disposed within the cannula of the viscoelastic delivery system. The conduit can be configured to be advanced out of the cannula into Schlemm's canal. In this embodiment, the viscoelastic material can be delivered into Schlemm's canal from the conduit. Delivery system 450 includes a mechanism that is capable of advancing and retracting the conduit along a length of cannula 452. The viscoelastic material may be delivered into Schlemm's canal of eye 400 by advancing the conduit through the distal opening of cannula 452 while the distal opening is in fluid communication with Schlemm's canal. Viscoelastic material can then be administered from the conduit into Schlemm's canal.

The viscoelastic material can be delivered into Schlemm's canal of the eye before or after delivering an ocular implant into the eye of the patient. In one embodiment, the delivery system can be connected to a visco module 460 that is remote from the main body or handle 453 of the delivery system 450. The visco module 460 can be configured to deliver the viscoelastic material through lumens or tubing into the conduit within the cannula of the delivery system. In one implementation, the delivery system can include a visco trigger 462 on handle 453 configured to release the viscoelastic material from the visco module 460 into the conduit of the delivery system.

The delivery system 450 can further include a conduit advancement wheel 464 configured to advance or retract the conduit within the cannula and within Schlemm's canal. For example, advancing the conduit advancement wheel 464 in the distal direction (e.g., towards the cannula) can advance the conduit towards a distal tip of the cannula and partially out of the cannula into Schlemm's canal of the patient's eye when the distal end of the cannula is in fluid communication with Schlemm's canal. Furthermore, moving the conduit advancement delivery wheel the in the proximal direction (e.g., towards the visco trigger 462) can move the conduit proximally within the cannula and to withdraw it within and from Schlemm's canal. The separate conduit advancement wheel 464 enables the conduit to be moved within Schlemm's canal without administering any viscoelastic material from the conduit. Likewise, the visco trigger 462 on the handle enables viscoelastic material to be administered from the conduit into Schlemm's canal without moving the conduit.

FIG. 4 is an illustration of a distal end of cannula 452 of the viscoelastic delivery system of FIG. 3. In FIG. 4, conduit 453 is shown partially extending from the distal opening 454 of the cannula 452. As described above, the conduit 453 can be slidably disposed within the cannula and can be advanced partially beyond the distal opening of the cannula (such as with conduit advancement wheel 464). Conduit 453 may be made, e.g., of Grilamid® polyamide, Pebax® elastomer, nylon, or any other suitable material. In one embodiment, the conduit can have a size (e.g., 0.008 inch OD by 0.006 inch ID) and a cross-sectional shape (e.g., circular cross-section, oval cross section, etc.) that matches the size and cross-sectional shape of the interior of the cannula. It should be understood that conduit 453 can be any shape so long as it is able to be slidably disposed within the cannula. Conduit 453 can have a length of 16-18 mm, enabling it to extend beyond the distal tip of the cannula half-way around Schlemm's canal. The conduit 453 can include a distal opening 455, which can be configured to deliver a viscoelastic material into a body structure such as Schlemm's canal. It should be understood that conduit 453 includes a lumen that fluidly communicates with a source of viscoelastic material (such as visco module 460) to facilitate administration of viscoelastic material. While the illustrative embodiment includes only a distal opening 455, in other embodiments the conduit can include additional openings, such as openings along a side of the conduit.

FIG. 5 is an illustration of a viscoelastic delivery system 500 that includes a delivery system 550 and a visco module 560 external to the delivery system 500. Delivery system 550 has a handle 552 and a cannula 554 extending from a distal end of handle 552. Cannula 554 has an internal passageway and a distal opening configured to be placed in fluid communication with Schlemm's canal. A conduit (not shown) is movably disposed within cannula 554 so that it can be advanced out of the cannula into Schlemm's canal and retracted back into the cannula.

The visco module 560 can be adapted to receive or accommodate a variety of visco syringes 566. The visco syringe 566 can be connected to tubing 568 (via, e.g., a female luer connector) using a sterile technique to fluidly couple the viscoelastic material in the interior chamber of the visco syringe to the conduit within delivery system 550. In one embodiment, the visco module 560 can be configured to automatically pressurize the interior chamber of visco syringe 566 when the syringe is inserted into the module. Toggling the visco trigger 562 on the handle 552 delivery system 550 can allow a pressurized flow of viscoelastic material to flow from the visco syringe and visco module into the delivery system 550 and out of one or more ports of the conduit of the delivery system and into Schlemm's canal. As described above, the delivery system can also include a conduit advancement wheel 564 configured to advance and retract a conduit within the cannula of the delivery system, thereby advancing and retracting the conduit within Schlemm's canal. The separate conduit advancement wheel 564 enables the conduit to be moved within Schlemm's canal without administering any viscoelastic material from the conduit. Likewise, the visco trigger 562 on the handle enables viscoelastic material to be administered from the conduit into Schlemm's canal without moving the conduit.

Figure 7:
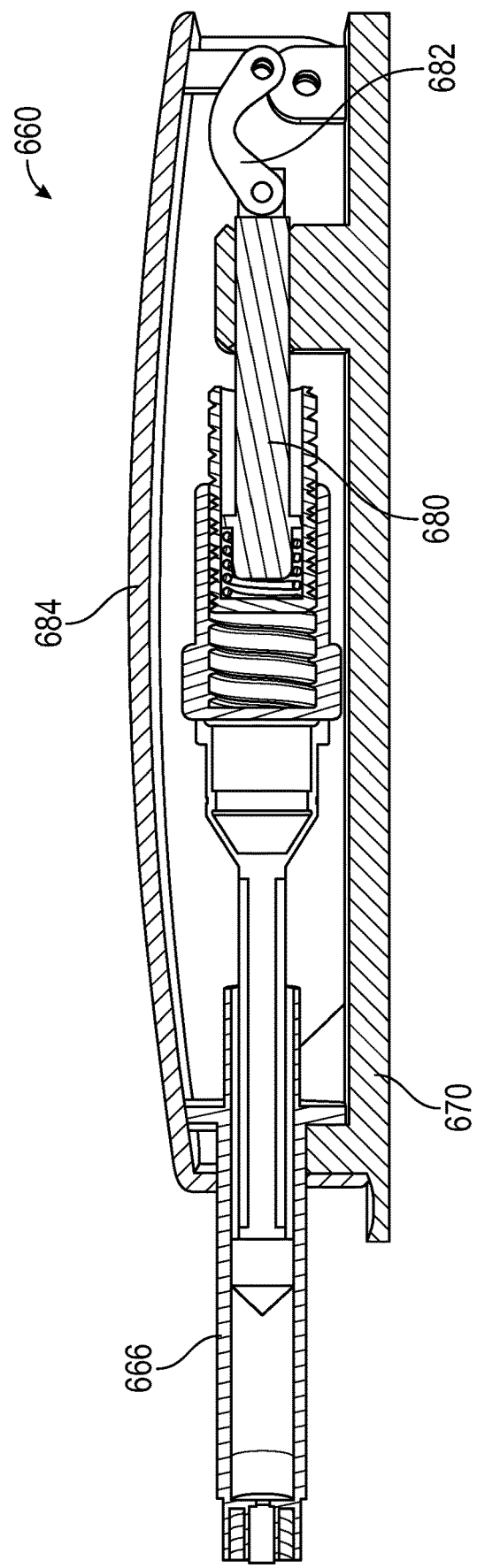
FIG. 7 is a partial cross-section and partial side elevational view illustrating the viscoelastic module of FIG. 6 in a closed, pressurized configuration.

FIGS. 6-7 illustrate cross-sectional views, respectively, of a visco module 660 in an open, unpressurized configuration and in a closed, pressurized configuration. In this embodiment, the visco syringe 666 can rest within cradle 670 which can be configured to accommodate a wide variety of visco syringe sizes and shapes. A spring assembly 674 (e.g., a compression spring or a constant force spring) can be placed into contact with plunger 672 of the syringe 666. In some embodiments, the spring assembly 674 can include an outer adjuster barrel 676 configured to adjust a position of the spring assembly to bring it into contact with the plunger 672. Rotation of the outer adjuster barrel 676 can adjust a relative position the outer adjuster barrel 676 with respect to an inner adjuster barrel 678. For example, the outer adjuster barrel can be threaded complimentarily with the inner adjuster barrel 678 to facilitate relative positioning adjustments of the outer adjuster barrel against the plunger 672.

The visco module 660 of FIGS. 6-7 further includes a piston 680 coupled to one end of an arm 682 and a module cover 684 coupled to another end of the arm. In some embodiments, these components can be rotationally coupled together with a pivot or a hinge. When the visco module is in the open configuration of FIG. 6, the module cover 684 pulls the arm 682 and the piston 680 away from the spring assembly 674. In the closed configuration of FIG. 7, however, closing the module cover 684 moves the arm and piston into the spring assembly to partially compress the spring. The spring assembly can then begin to apply a constant force to the plunger 672 of the syringe 666, effectively pressurizing the syringe. An operator can then control delivery of viscoelastic material from the reservoir of syringe 666 into the delivery system, for example, by deploying a visco trigger (such as visco trigger 562 in FIG. 5) on the delivery system that is connected to the visco module.

Figure 8:
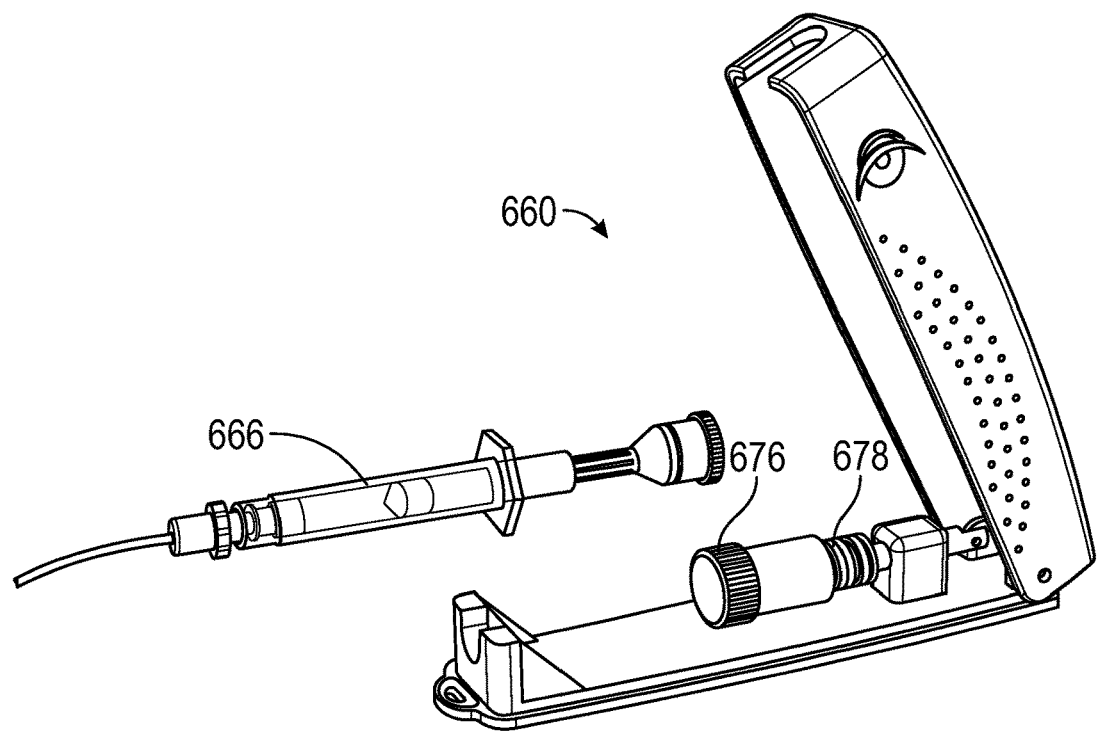
FIG. 8 is a perspective view showing a visco syringe being loaded into the viscoelastic module of FIGS. 6-7.
Figure 9:
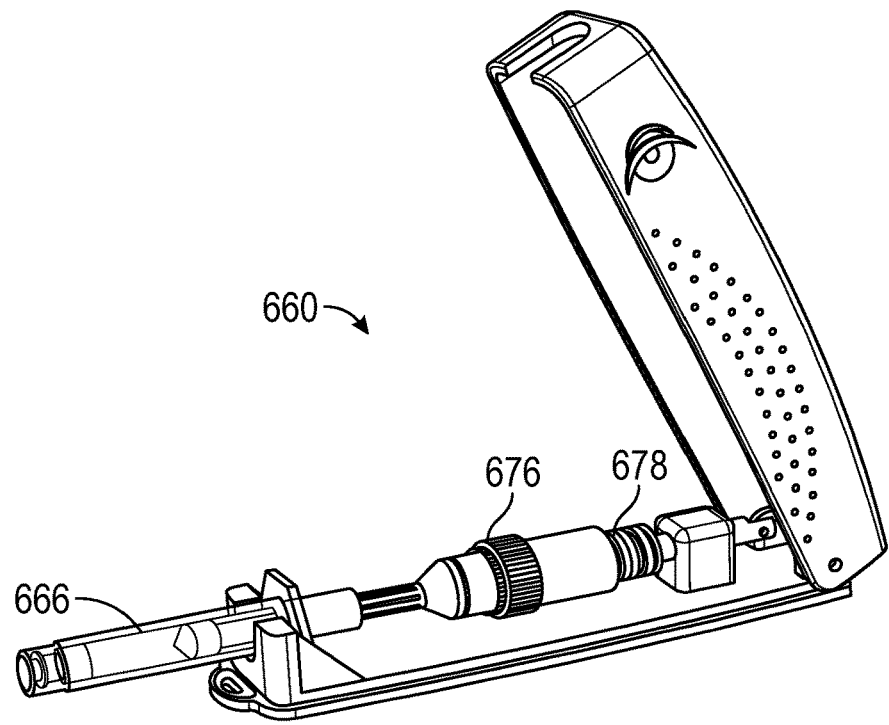
FIG. 9 is a perspective view showing a visco syringe loaded into the viscoelastic module of FIGS. 6-8.

FIGS. 8-9 are additional views of the visco module of FIGS. 6-7 showing the loading of a visco syringe 666 into the visco module 660. Outer adjuster barrel 676 and inner adjuster barrel 678 are also shown in FIGS. 8-9 illustrating how fine-tuning adjustments can be made to position the spring assembly against the plunger of the syringe.

Figure 10:
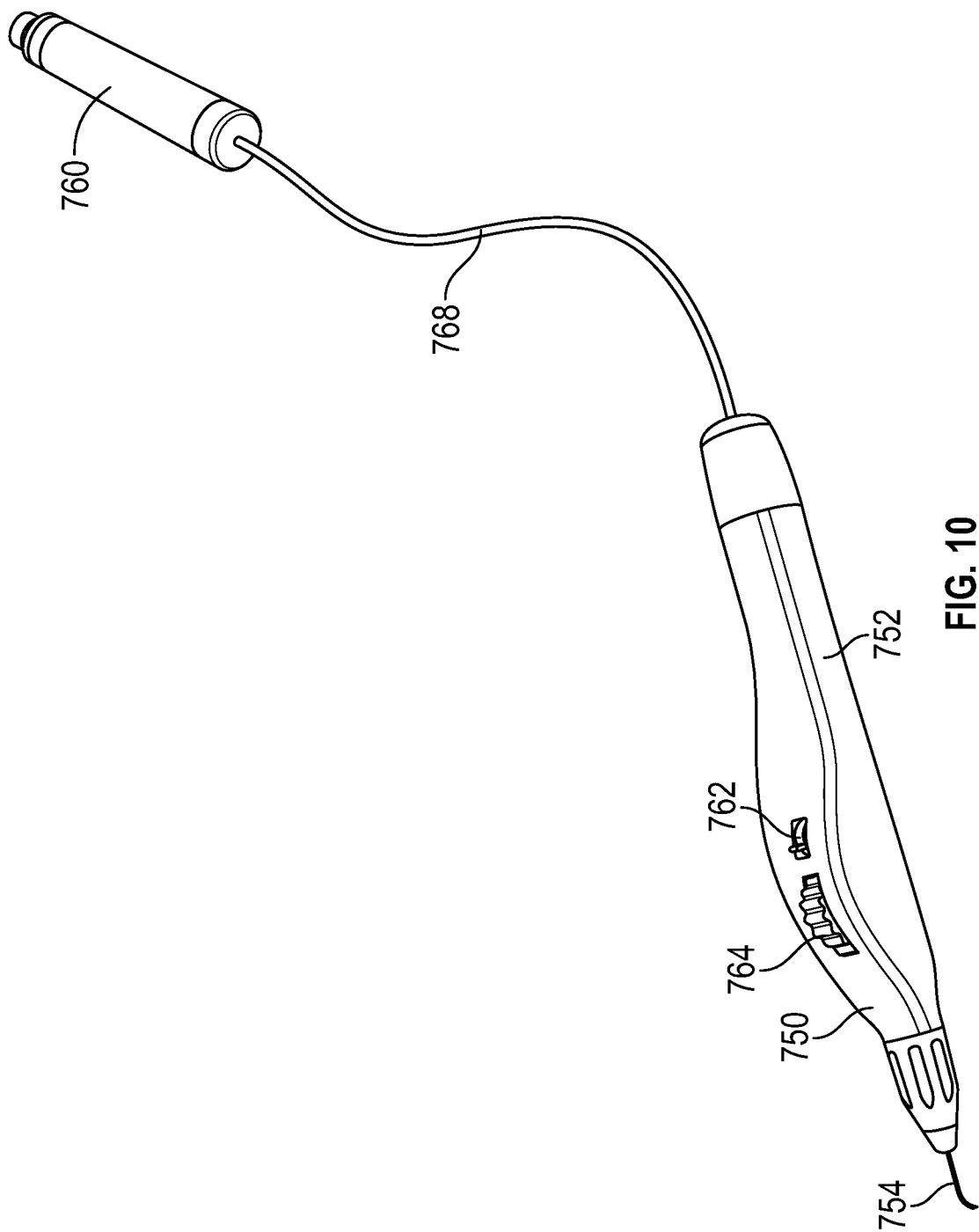
FIG. 10 is a perspective view illustrating another embodiment of a viscoelastic delivery system.
Figure 11:
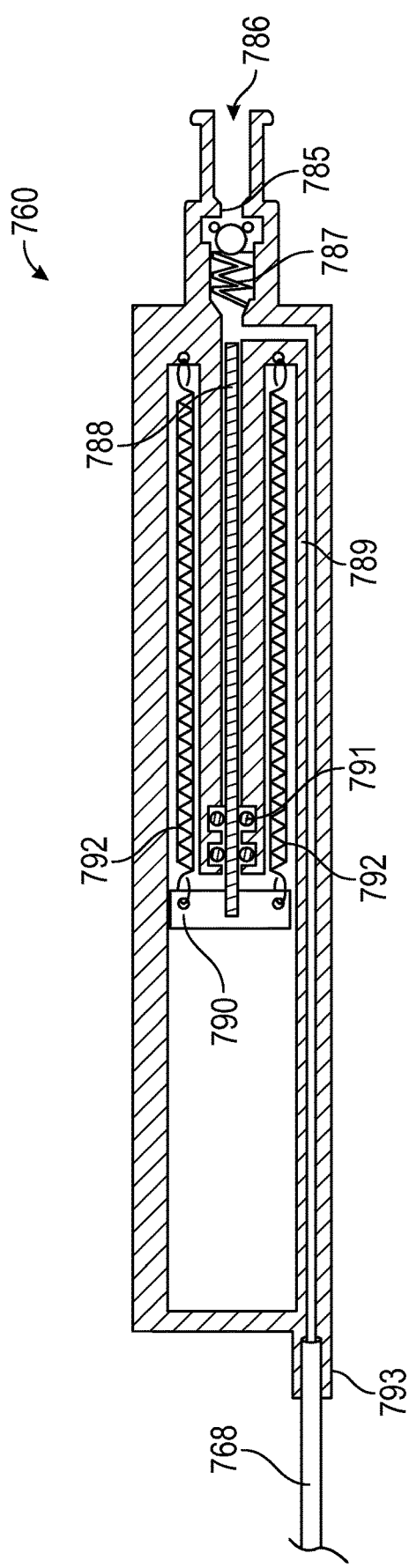
FIG. 11 is a side cross-sectional view showing details of the viscoelastic module of the viscoelastic delivery system of FIG. 10.
Figure 12:
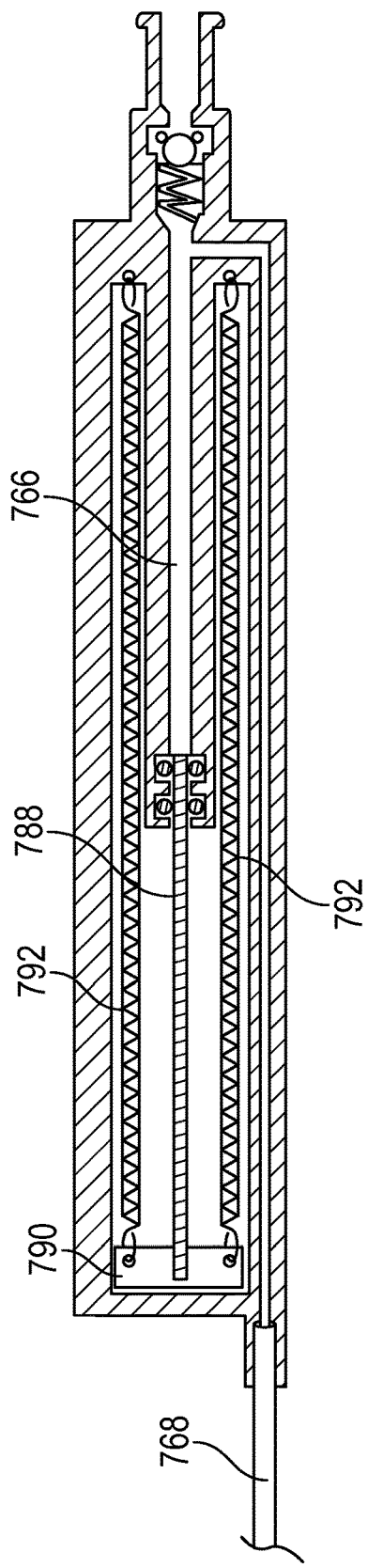
FIG. 12 is a side cross-sectional view of the viscoelastic module of FIG. 11 showing the reservoir fully loaded with viscoelastic material.

FIGS. 10-12 illustrate another embodiment of a viscoelastic delivery system 700 that includes a delivery system 750 and a visco module 760. Delivery system 750 has a handle 752 and a cannula 754 extending from a distal end of handle 752. Cannula 754 has an internal passageway and a distal opening configured to be placed in fluid communication with Schlemm's canal. A conduit (not shown) is movably disposed within cannula 754 so that it can be advanced out of the cannula into Schlemm's canal and retracted back into the cannula. The conduit has one or more exit ports. A toggling visco trigger 762 on the delivery system 750 can allow a pressurized flow of viscoelastic material to flow from the visco module 760 through tubing 768, into the conduit within cannula 754 and out of the conduit exit port(s).

The visco module 760 is adapted to receive viscoelastic material from a visco syringe prior to use of the system to treat a patient. As shown in FIGS. 11-12, the outlet of a visco syringe can connect with a luer fitting 786 at an inlet 785 of the visco module 760. The visco syringe may inject viscoelastic material through inlet 785 and one-way valve 787 into a passageway 789 that leads to a luer connector. Tubing 768 connected to connector 793 extends to the delivery system. The system may be primed during injection of viscoelastic material from the visco syringe by opening the visco trigger 762 until viscoelastic material passes from inlet 785, passageway 789, tubing 768 and out of the exit port(s) of the conduit, as shown in FIG. 11. Releasing visco trigger stops the flow of viscoelastic material through the conduit. Thereafter, as viscoelastic material is continued to be injected from the visco syringe, the fluid pressure moves piston rod 788 away from inlet 785 against the operation of springs 792 (which are connected to piston rod 788 via plate 790), and pressurized viscoelastic material fills chamber 766, as shown in FIG. 12. When filling is complete, the visco syringe is removed, and one-way valve 787 prevents viscoelastic material from flowing back through inlet 785. O ring seals 791 prevent viscoelastic material from leaking around piston rod 788. When visco trigger 762 of delivery system 750 is toggled open again, springs 792 move piston rod 788 back toward inlet 785. Because one-way valve 787 prevents the viscoelastic material from passing through inlet 785, this movement of piston rod 788 ejects viscoelastic material from chamber 766 into passageway 789, tubing 768, and into the conduit within cannula 754. The visco module returns to the configuration of FIG. 11 after all viscoelastic material has been delivered from chamber 766 through tubing 768.

A conduit advancement wheel 764 is configured to advance and retract the conduit within the cannula 754 of the delivery system. The separate conduit advancement wheel 764 enables the conduit to be moved within Schlemm's canal without administering any viscoelastic material from the conduit. Likewise, the visco trigger 762 on the handle enables viscoelastic material to be administered from the conduit into Schlemm's canal without moving the conduit.

Figure 13:
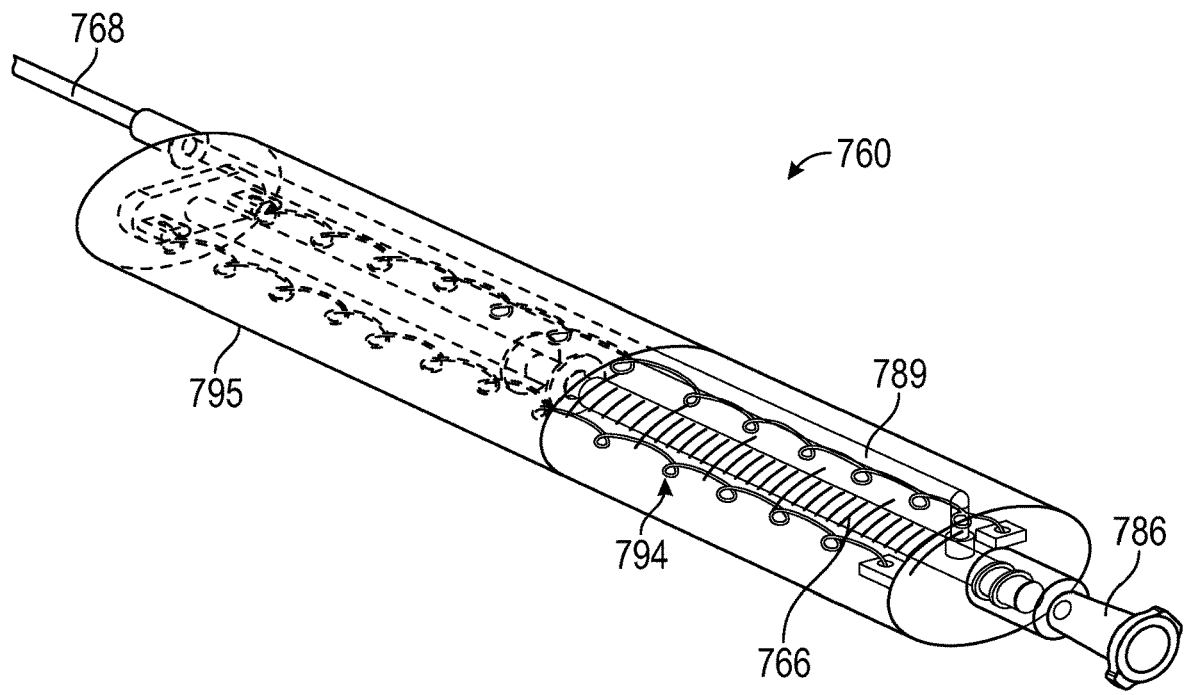
FIG. 13 is a perspective view showing an embodiment of a viscoelastic module with a partially see-through housing and graduated markings.
Figure 14:
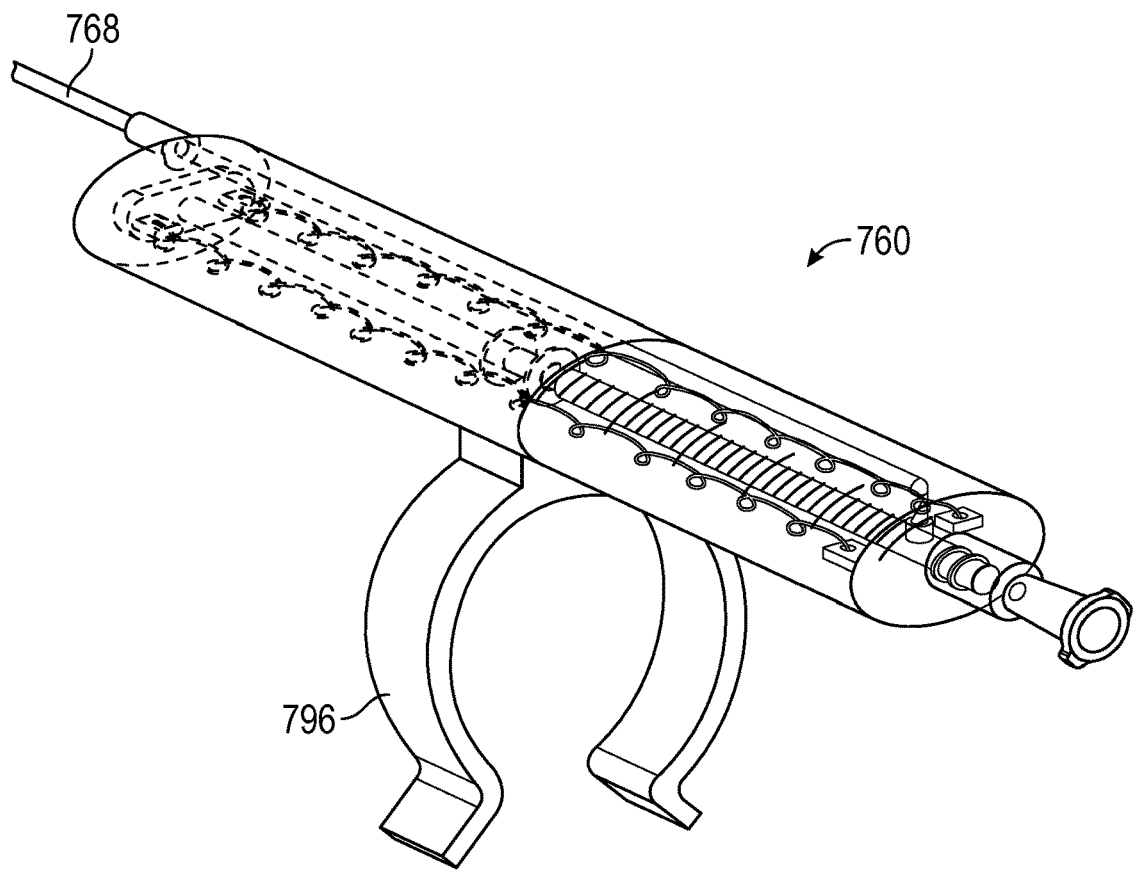
FIG. 14 is a perspective view showing the viscoelastic module of FIG. 13 with a clip for attaching the module to, e.g., a user's wrist or arm or to a pole.
Figure 22:
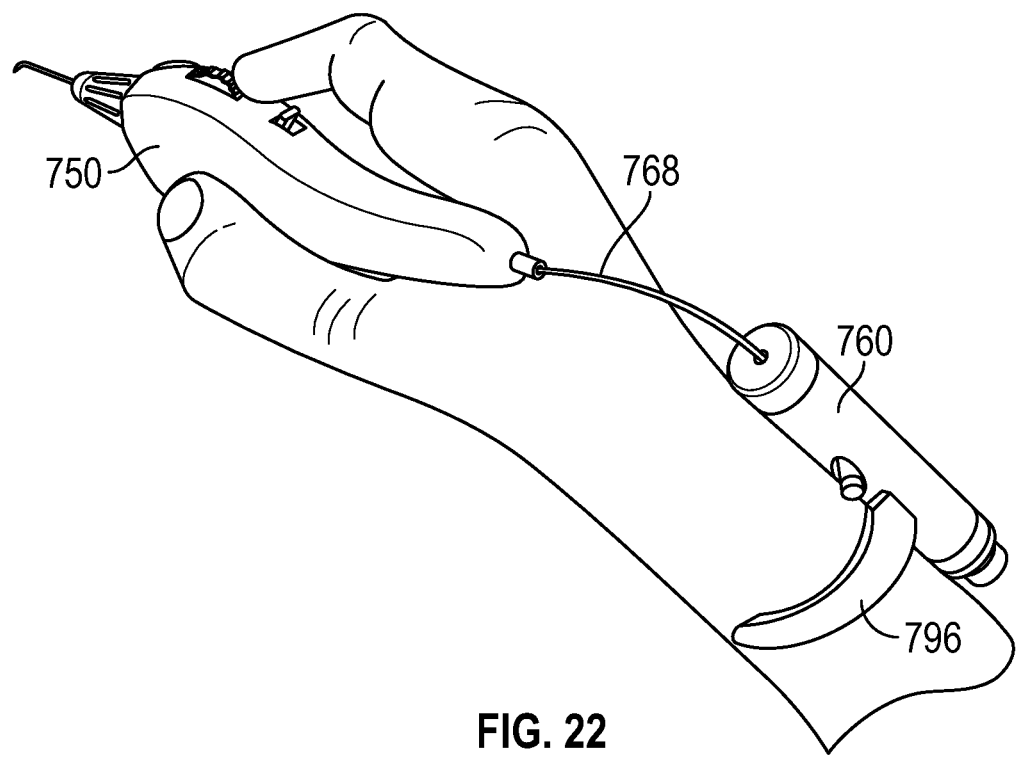
FIG. 22 is a perspective view of a viscoelastic delivery system showing a viscoelastic module (such as the viscoelastic module shown in FIG. 14) attached to a user's arm.
Figure 23:
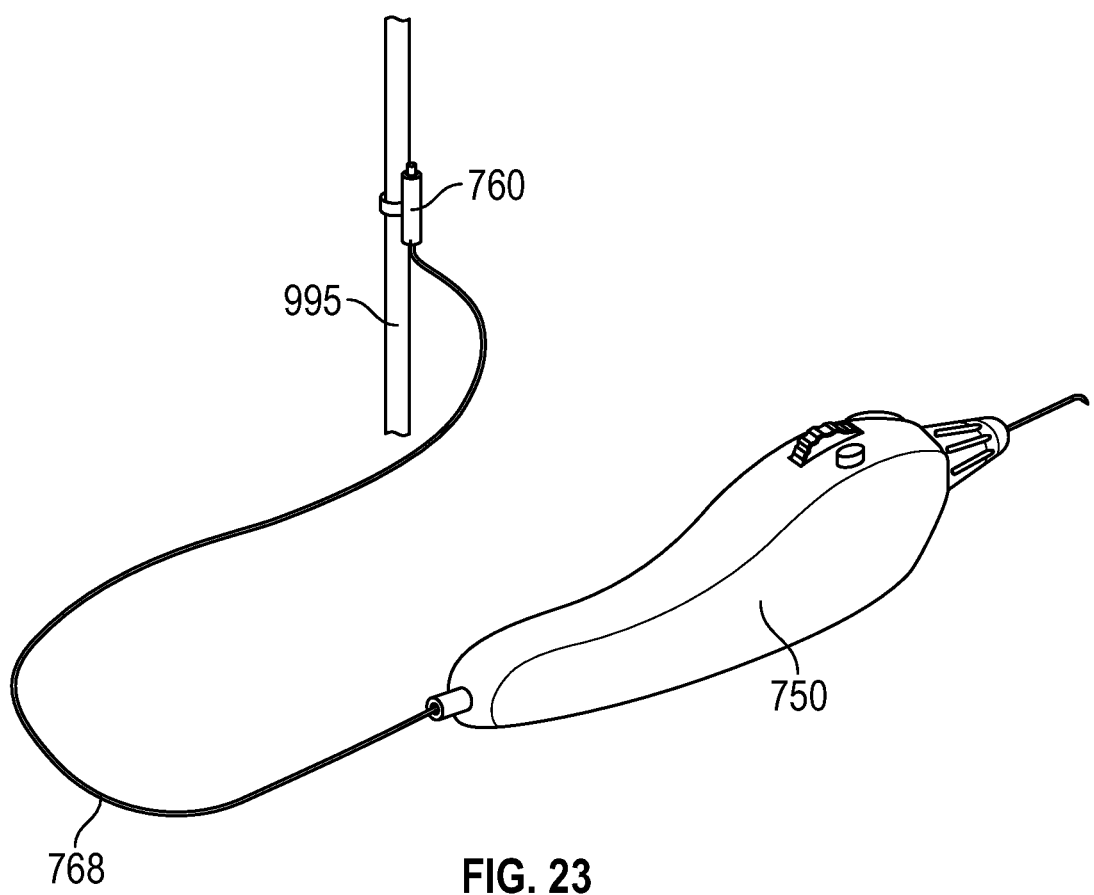
FIG. 23 is a perspective view of a viscoelastic delivery system showing a viscoelastic module (such as the viscoelastic module shown in FIG. 14) attached to an IV stand.
Figure 24:
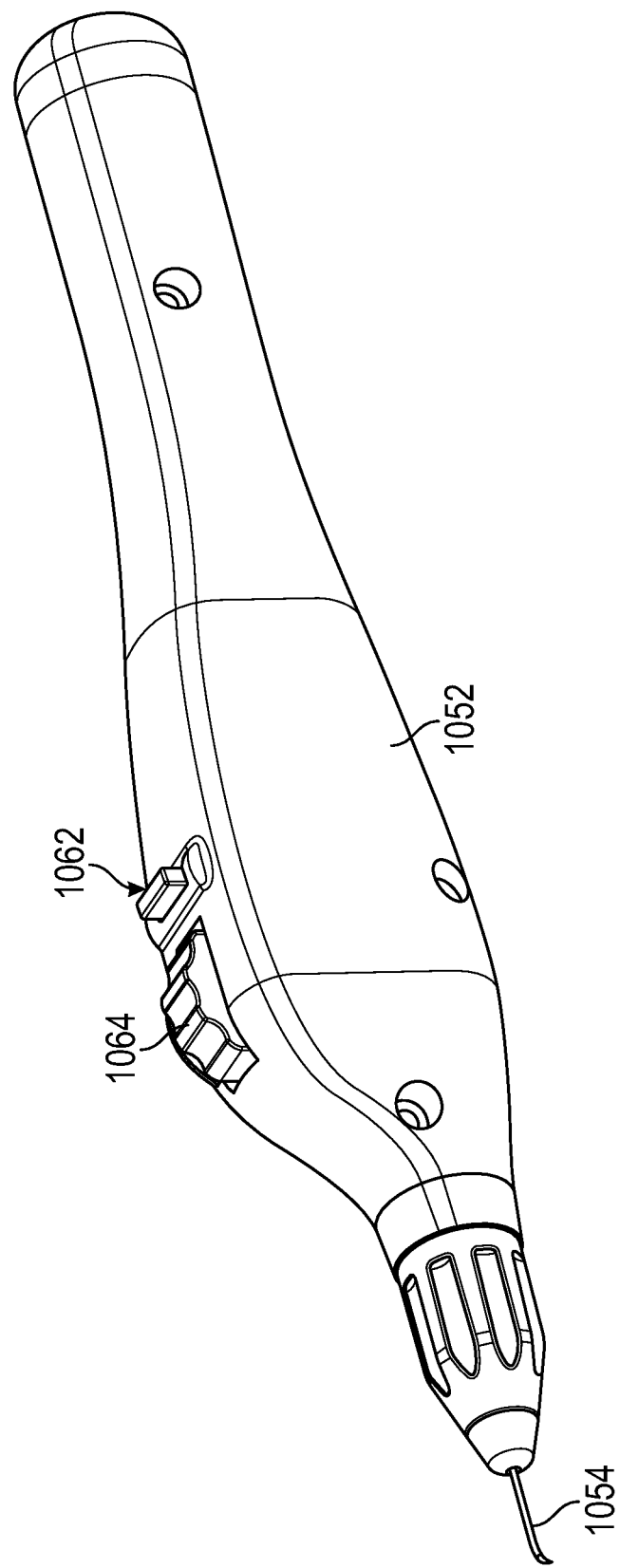
FIG. 24 is a perspective view of a viscoelastic delivery system according to an embodiment of the invention including first and second controls configured to control delivery of the viscoelastic material and adjustment of the position of the conduit relative to the cannula.

FIG. 13 shows an embodiment of visco module 760 that adds graduated markings 794 to a partially transparent or translucent visco module body to form a viscoelastic chamber gauge. A portion 795 of the body may be opaque to hide the springs 792. FIG. 14 shows an embodiment of the visco module 760 that adds an integral clip 796 to attach the visco module to an IV pole 995 (as shown in FIG. 23), to the user's wrist (as shown in FIG. 22), or to the user's clothing. In other embodiments, the clip 796 can be omitted, and the tubing 768 tethers module 760 to the handle of the delivery system 750 as the module 760 and tubing drape over the user's wrist. In embodiments, tubing 768 can be 3-4 inches long to enable this draping feature. In various embodiments, tubing 768 can be formed from a high pressure braided reinforced tube.

FIGS. 15-18 illustrate an alternative embodiment of a visco module 860. Similar to the embodiments described above, the visco module can implement a spring (e.g., a compression spring) to provide compression against a plunger to pressurize a flow of viscoelastic material within the visco module. In this embodiment, the visco module can include a luer fitting 886 and a one-way check valve 887, as in the embodiment of FIGS. 10-12. A passageway 889 extends through a rod 802 to a visco reservoir 894. Rod 802 extends from a compression knob 896, a threaded member 804 connected to the compression knob 896, a compression spring 892, and a piston 889. An outlet 895 from visco reservoir 894 is adapted to connect via a connector 893 to a tubing (not shown) leading to a delivery system (not shown), such as the delivery system 750 described above. The reservoir 894 can be filled with a viscoelastic material, such as by connecting a visco syringe to the luer fitting 886, with the visco module in the configuration shown in FIG. 16. If a visco delivery system is connected to the outlet of reservoir 894 via tubing, and if the visco delivery system's visco delivery trigger is pushed to the open position, viscoelastic material will first fill reservoir 894 and will then flow into the tubing and through the delivery system to the delivery system's conduit exit ports to prime the system. After toggling the delivery system's visco delivery trigger to the closed position, the viscoelastic material in the visco reservoir 894 of visco module 860 can be pressurized by turning compression knob 896 so that threaded member 804 advances into the housing 806 (which has corresponding threads). With the visco delivery trigger in the closed position, viscoelastic material cannot flow out of reservoir 894, and the piston 889 stays in its withdrawn position as the threaded member 804 advances. A flange 808 on the end of threaded member 804 compresses spring 892 against piston 889 during advancement of the threaded member to pressurize reservoir 894, as shown in FIG. 17. An operator can then control delivery of viscoelastic material from the visco module 860 into the delivery system, for example, by deploying a visco trigger (such as visco trigger 762 in FIG. 10) on the delivery system that is connected to the visco module. As viscoelastic material is delivered from reservoir 894, spring 892 moves piston 889 toward outlet 895 until the reservoir is depleted, as shown in FIG. 18. In some embodiments, the reservoir portion of housing 806, or all of housing 806, may be clear or translucent so that the quantity of viscoelastic material it contains can be seen. Markings may be added to the housing to help quantify the amount of viscoelastic material delivered and/or the amount remaining in the housing.

Figure 19:
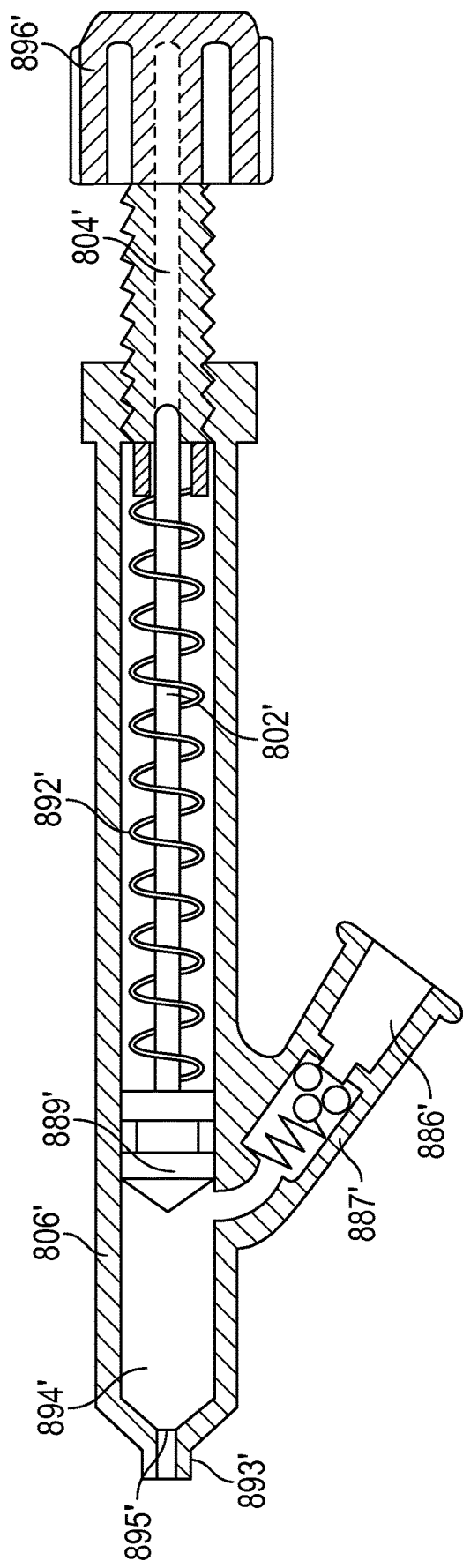
FIG. 19 is a partial cross-sectional view illustrating a modification of the embodiment of FIGS. 15-18.

FIG. 19 illustrates a modification to the embodiment of FIGS. 15-18. In this embodiment, the visco inlet luer fitting 886' and a one-way check valve 887' are on the side of the housing 806' of the visco module 860'. Rod 802' extends between a threaded member 804' connected to a compression knob 896' and a piston 889'. A compression spring 892' also extends between threaded member 804' and piston 889'. An outlet 895' from visco reservoir 894' is adapted to connect via a connector 893' to a tubing (not shown) leading to a delivery system (not shown), such as the delivery system 750 described above. The reservoir 894' can be filled with a viscoelastic material, such as by connecting a visco syringe to the luer fitting 886', with the visco module in the configuration shown in FIG. 19. If a visco delivery system is connected to the outlet of reservoir 894' via tubing, and if the visco delivery system's visco delivery trigger is pushed to the open position, viscoelastic material will first fill reservoir 894' and will then flow into the tubing and through the delivery system to the delivery system's conduit exit ports to prime the system. After toggling the delivery system's visco delivery trigger to the closed position, the viscoelastic material in the visco reservoir 894' of visco module 860' can be pressurized by turning compression knob 896' so that threaded member 804' advances into the housing 806' (which has corresponding threads). With the visco delivery trigger in the closed position, viscoelastic material cannot flow out of reservoir 894', and the piston 889' stays in its withdrawn position as the threaded member 804' advances. A flange on the end of threaded member 804' compresses spring 892' against piston 889' during advancement of the threaded member to pressurize reservoir 894'. An operator can then control delivery of viscoelastic material from the visco module 860' into the delivery system, for example, by deploying a visco trigger (such as visco trigger 762 in FIG. 10) on the delivery system that is connected to the visco module. As viscoelastic material is delivered from reservoir 894', spring 892' moves piston 889' toward outlet 895' until the reservoir is depleted. In some embodiments, the reservoir portion of housing 806', or all of housing 806', may be clear or translucent so that the quantity of viscoelastic material it contains can be seen. Markings may be added to the housing to help quantify the amount of viscoelastic material delivered and/or the amount remaining in the housing.

FIGS. 20-21 illustrate still another embodiment of a visco module 1200 for use with, e.g., the viscoelastic delivery systems described herein. In this embodiment, the visco inlet luer fitting 1202 and a one-way check valve 1204 lead to an inlet 1206 on the top front side of the housing 1208 of the visco module 1200. Inlet 1206 extends from check valve 1204 to a top end of a tapered reservoir portion 1212 disposed at the end of a cylindrical reservoir portion 1214 of a reservoir 1210. Rod 1216 extends from a piston 1222 to an interior channel 1218 of a hollow rod 1219 extending from a compression knob 1220. A compression spring 1224 extends between one end of rod 1219 and piston 1222. An outlet 1225 at the tapered portion 1212 of visco reservoir 1210 is adapted to connect via a connector 1226 to a tubing (not shown) leading to a delivery system (not shown), such as the delivery system 750 described above. O-rings 1228 seal piston against the inner wall of reservoir 1210 to prevent viscoelastic material from leaking around the piston.

The reservoir 1210 can be filled with a viscoelastic material (such as by connecting a visco syringe to the luer fitting 1202) to move piston 1222 within reservoir 1210 away from inlet 1204 to the position shown in FIG. 20 in which piston 1222 engages the forward edge of a stop tube 1221, but with the spring 1224 of the visco module in an uncompressed configuration (not shown) and with the compression knob 1220 rotated away from housing 1208 (also not shown) to permit piston movement away from inlet 1204 during injection of viscoelastic material from the syringe. If a visco delivery system is connected via tubing to the outlet of reservoir 1210, and if the visco delivery system's visco delivery trigger is pushed to the open position, viscoelastic material will first flow into the reservoir tapered portion 1212, then into tubing connected to connector 1226 and through the delivery system to the delivery system's conduit exit ports to prime the system. Additional viscoelastic material will then fill the remaining reservoir as the piston is pushed back. The position of inlet 1206 just below the reservoir's cylindrical portion 1214 will cause viscoelastic material to flow across the bottom face 1223 of piston 1222 at the beginning of the priming process, when the piston is at the end of cylindrical portion 1214 (as shown in FIG. 21), thereby purging any air bubbles that may form and deposit on piston face 1223 or in reservoir tapered portion 1212.

After toggling the delivery system's visco delivery trigger to the closed position, the viscoelastic material in the visco reservoir 1210 of visco module 1200 can be pressurized by turning compression knob 1220 so that hollow rod 1219 advances over rod 1216 into the housing 1208 (which has corresponding threads). With the visco delivery trigger in the closed position, viscoelastic material cannot flow out of reservoir 1210, and the piston 1222 stays in its withdrawn position as the rod 1219 advances, thereby compressing spring 1224 and pressurizing reservoir 1210, as shown in FIG. 20. An operator can then control delivery of viscoelastic material from the visco module 1200 into the delivery system, for example, by deploying a visco trigger (such as visco trigger 762 in FIG. 10) on the delivery system that is connected to the visco module. As viscoelastic material is delivered from reservoir 1200, spring 1224 moves piston 1222 toward outlet 1225 until the piston reaches the end of its range of motion, as shown in FIG. 21. In some embodiments, the reservoir portion of housing 1208, or all of housing 1208, may be clear or translucent so that the quantity of viscoelastic material it contains can be seen. Markings may be added to the housing to help quantify the amount of viscoelastic material delivered and/or the amount remaining in the housing.

Figure 25:
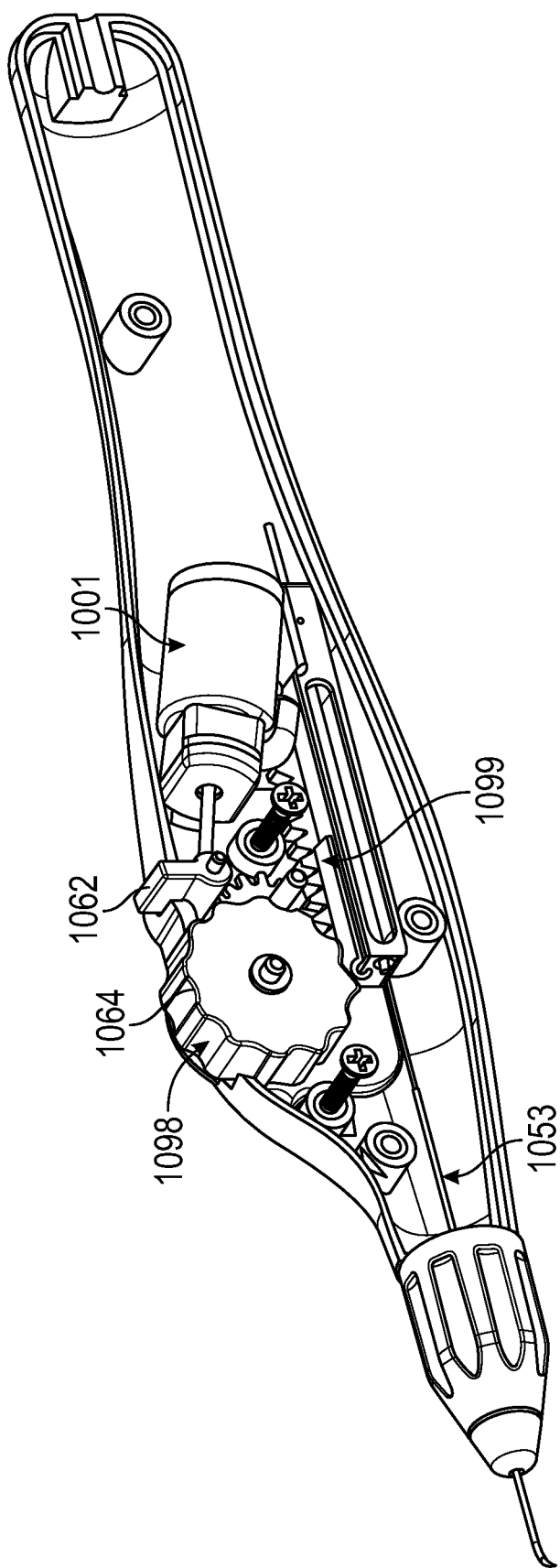
FIG. 25 is a cross-sectional view of the delivery system of FIG. 24.

FIGS. 24-28 illustrate various views of a viscoelastic delivery system 1050 as discussed herein. As described above, the delivery system can include a visco trigger 1062 and a conduit advancement wheel 1064 supported by a handle 1052. A cannula 1054 extends from the distal end of handle 1052. Cannula 1054 has an internal passageway and a distal opening configured to be placed in fluid communication with Schlemm's canal. Referring to FIG. 25, the conduit advancement wheel 1064 can include a number of notches 1098. The wheel can be coupled to a rack and pinion mechanism 1099 which is coupled to a conduit 1053 (formed, e.g., from a Vestamid® ML21 nylon extrusion) to control advancement of the conduit 1053 within the cannula 1054.

In some embodiments, the gearing of the rack and pinion system can be optimized to advance the conduit by a set distance for every notch 1098 of the conduit advancement wheel 1064. For example, in one embodiment, the notches can be spaced apart by 3 mm, and 1:1 gearing can be used in the rack and pinion system such that advancement of the conduit advancement wheel by one notch will advance the conduit by 3 mm. In alternative embodiments, other gearing ratios can be used. For example, a 2:1 gearing ratio can be used to advance the conduit by 6 mm when there is a 3 mm spacing between notches.

Figure 26:
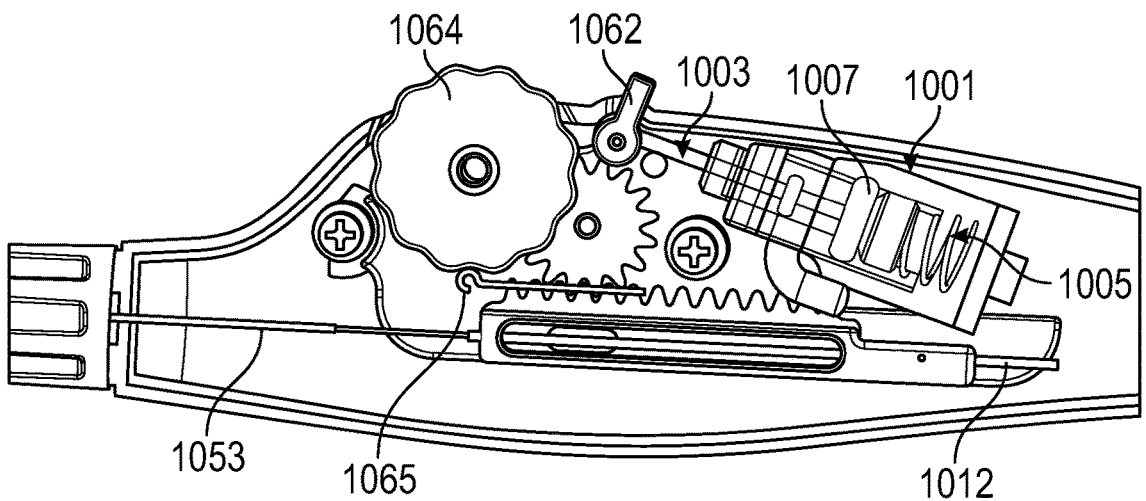
FIG. 26 is a cross-sectional view showing aspects of the delivery system of FIGS. 24-25.
Figure 27:
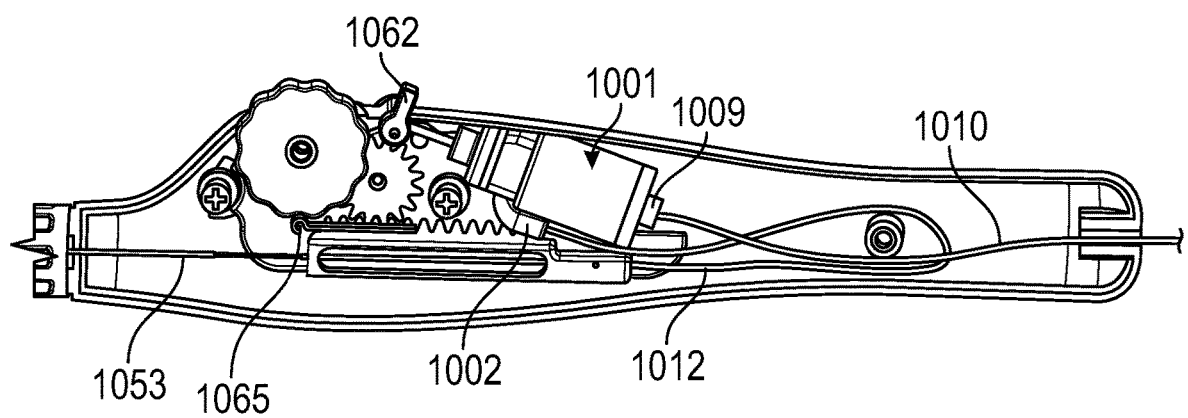
FIG. 27 is a cross-sectional view showing aspects of the delivery system of FIGS. 24-26.
Figure 30:
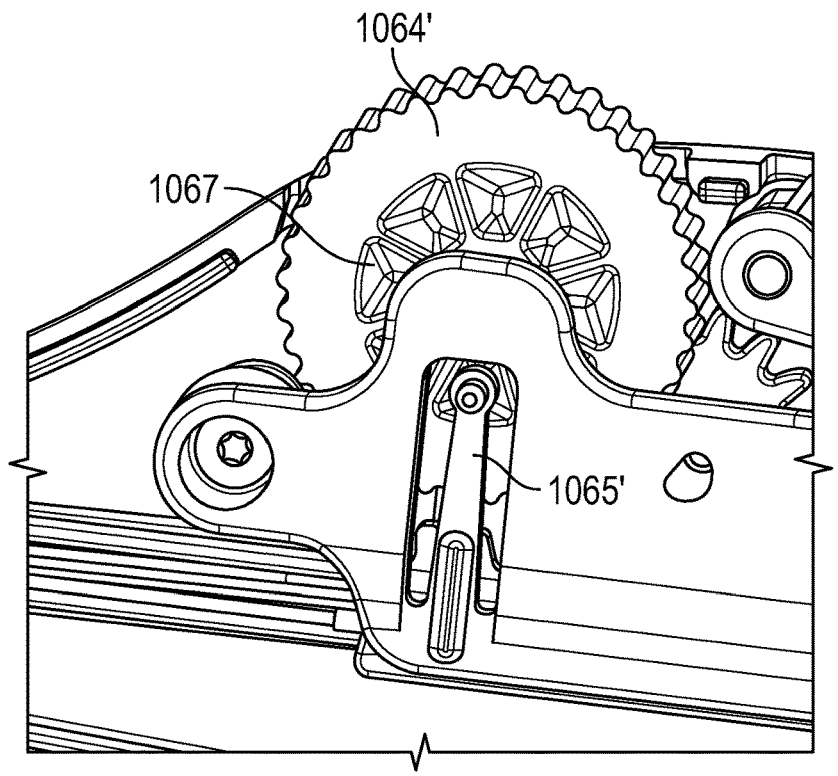
FIG. 30 is a cross-sectional view of part of the viscoelastic delivery system of FIGS. 24-28 but with an alternative design for an advancement wheel according to an embodiment of the invention.
Figure 31:
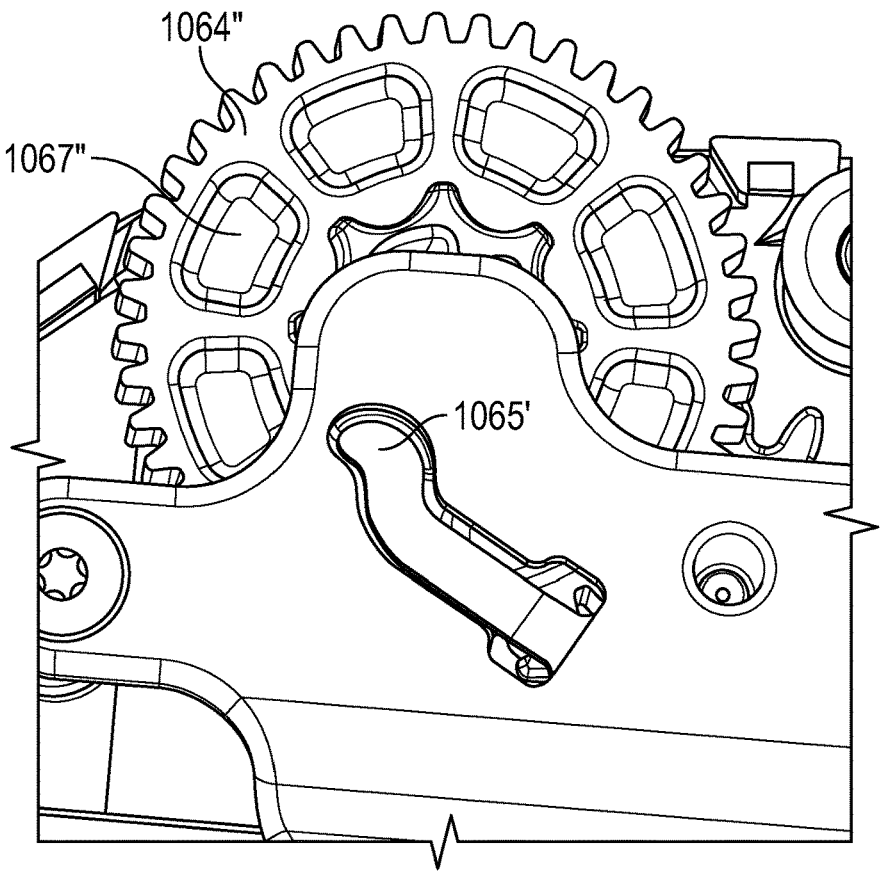
FIG. 31 is a cross-sectional view of part of the viscoelastic delivery system of FIGS. 24-28 but with yet another alternative design for an advancement wheel.

As shown in FIGS. 26-27, a cantilever spring 1065 formed from wire or as a molded plastic bar can slide along the ridges of the notched conduit advancement wheel 1064 to give the user tactile feedback to know exactly how far the conduit is advanced into Schlemm's canal when the wheel is rotated, giving the user knowledge of where viscoelastic material is injected relative to the cannula tip. FIG. 30 shows an alternative conduit advancement wheel 1064' and an alternative cantilever spring 1065' that slides into and out of depressions 1067 in the side of wheel 1064' to provide tactile feedback. FIG. 31 shows yet another alternative advancement wheel 1064" with depressions 1067" and a cantilever spring 1065" for tactile feedback of conduit advancement.

In some embodiments, the rack and pinion mechanism 1099 is configured to travel 24 mm. In the completely retracted configuration, 24 mm of the conduit 1053 resides within handle 1052, and the conduit resides within the straight portion of cannula 1054 proximal to the distal curved portion of the cannula. The conduit can be kept in this configuration during shipping and/or storage so that the conduit does not take on a curved set from the curved portion of the cannula. The 24 mm of rack movement to the most extended configuration will result in 20 mm of conduit being extended from the cannula.

Referring to FIGS. 25-28, operation of the visco trigger 1062 will now be discussed. As described above, the visco trigger 1062 can comprise a simple toggle lever, which can be alternated between and off state and an on state. When the visco trigger is in the off state, the delivery system 1050 does not deliver a flow a viscoelastic material through the conduit within the cannula. In contrast, when the visco trigger is moved to the on state, a flow of viscoelastic material is allowed to flow from the visco module (described above) through the toggle valve 1001, and into the conduit/cannula of the delivery system. Thus, the amount of viscoelastic material delivered from the delivery system is correlated with the length of time the visco trigger is in the on state.

Figure 28:
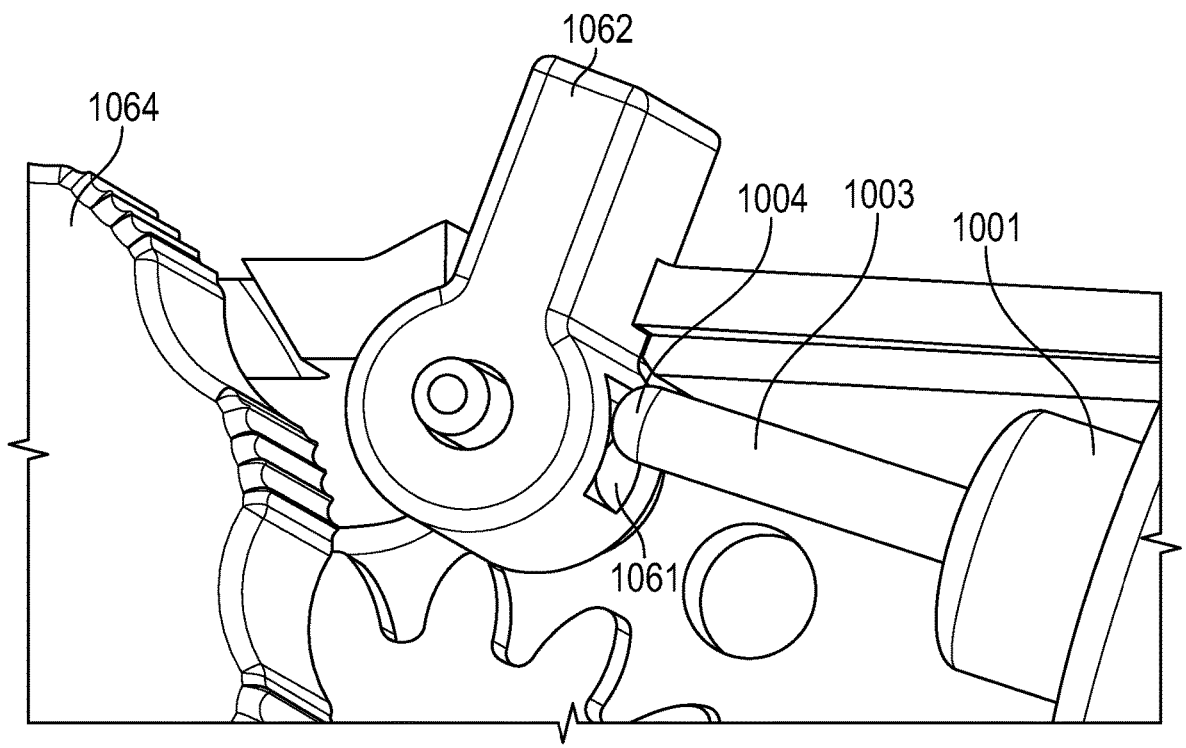
FIG. 28 is a cross-sectional view showing aspects of the delivery system of FIGS. 24-27.

Referring to FIGS. 26-28, a shaft 1003 is disposed at a position offset from the rotational axis 1063 of visco trigger 1062, and the distal end of shaft 1003 is disposed within a groove 1061 in visco trigger 1062. The distal end 1004 of shaft 1003 slides within groove 1061 as trigger 1062 moves. The distal end 1004 of shaft 1003 may be convex, as shown in FIG. 28, or flat. The offset position of shaft 1003 with respect to the rotational axis of trigger 1062 causes shaft 1003 to move forward and back along its longitudinal axis, which compresses spring 1005 and moves the position of one or more o-rings 1007 within the toggle valve 1001. The movement of o-ring(s) 1007 opens the valve to allow a pressurized flow of viscoelastic material to flow from the visco module (described above) through tubing 1010 into valve inlet 1009 and out of a valve outlet (not shown) into tubing 1012 leading to the conduit 1053. (FIG. 26 omits tubing 1010 and most of tubing 1012 for clarity. Likewise, FIG. 28 shows valve outlet 1011 with tubing 1012 omitted for clarity.) When the user's actuation force is released from the visco trigger, the spring 1005 decompresses to move shaft 1003 and the o-rings 1007 back into place, returning visco trigger 1062 to its off state, closing the valve, and effectively stopping the flow of pressurized viscoelastic material.

Figure 29:
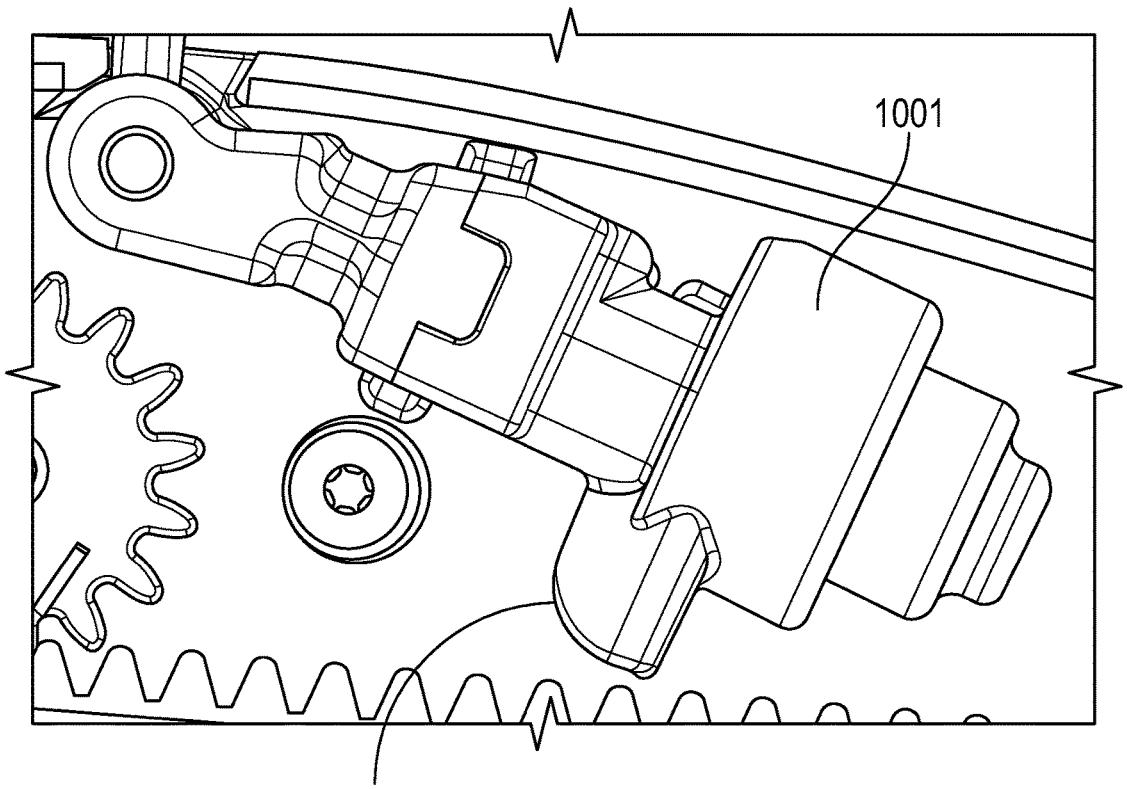
FIG. 29 is a cross-sectional view of part of the viscoelastic delivery system of FIGS. 24-28 but with an alternative design for a strain relief element according to an embodiment of the invention.

Tubing 1012 extends from the valve outlet over a strain relief element 1002 on the side of toggle valve 1001. Tubing 1012 forms a loop within handle 1052 when the rack and pinion is in its most retracted position, as shown in FIG. 27, and straightens out during advancement of the conduit. FIG. 29 shows a strain relief element 1002' with an alternative shape.

Figure 32:
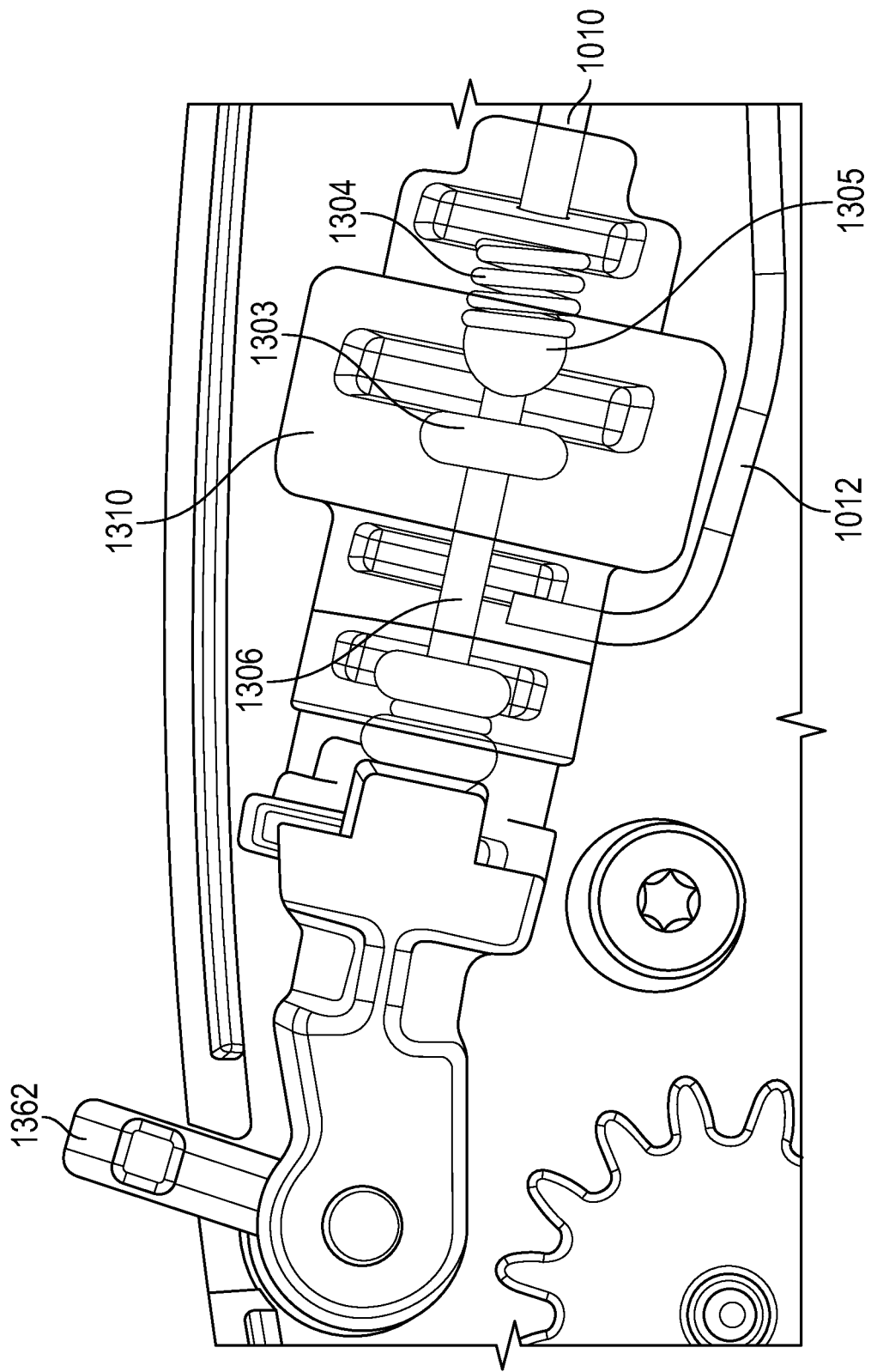
FIG. 32 is a partial cross-sectional view illustrating aspects of a viscoelastic delivery system according to alternative embodiments of the invention.
Figure 33:
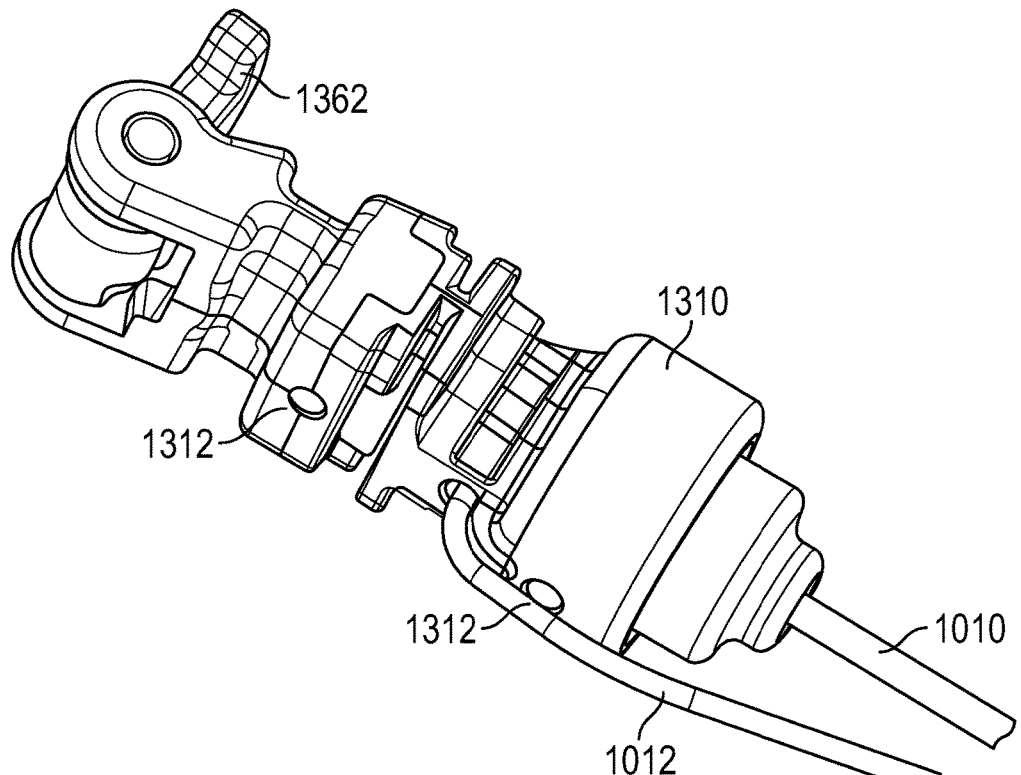
FIG. 33 is a perspective view of some components of the viscoelastic delivery system of FIG. 32.
Figure 34:
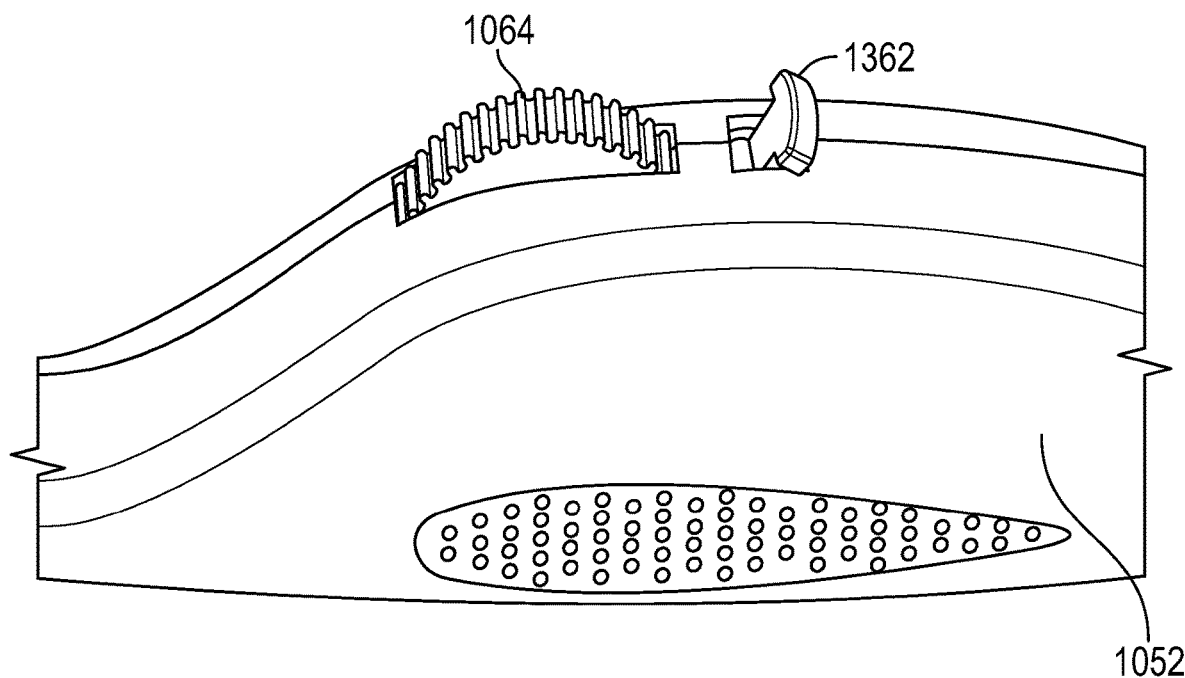
FIG. 34 is a perspective view of the exterior of the viscoelastic delivery system of FIGS. 32-33.

FIGS. 32-34 illustrate other alternative embodiments of some components of viscoelastic delivery system of FIGS. 24-28. In one embodiment, the visco trigger 1362 of the delivery system has a modified shape. As described above, the visco trigger 1362 can be a simple toggle lever, which can be alternated between and off state and an on state. When the visco trigger is in the off state, the delivery system 1050 does not deliver a flow a viscoelastic material through the conduit within the cannula. In contrast, when an actuation force is applied to the visco trigger, the visco trigger is moved rearward to the on state (as shown in FIGS. 32-34), and a flow of viscoelastic material is allowed to flow from the visco module (described above) through the toggle valve 1301 and into the conduit/cannula of the delivery system. Specifically, rearward movement of visco trigger 1362 moves shaft 1306 against the action of spring 1304 to move ball valve 1305 away from its seat on O-ring 1303 (as shown in FIG. 32 with valve housing 1310 shown in phantom), thereby allowing pressurized viscoelastic material to flow into valve housing 1310 and out into tubing 1012 leading to the delivery system's conduit (not shown). When the actuation force is removed, visco trigger 1362 returns to the off state, the spring 1304 decompresses to move ball valve 1305 back into place against its seat on O-ring 1303, closing the valve and effectively stopping the flow of pressurized viscoelastic material. The components of valve housing 1310 may be glued together. Openings 1312 may be formed in valve housing 1310 to facilitate glue injection.

Figure 35:
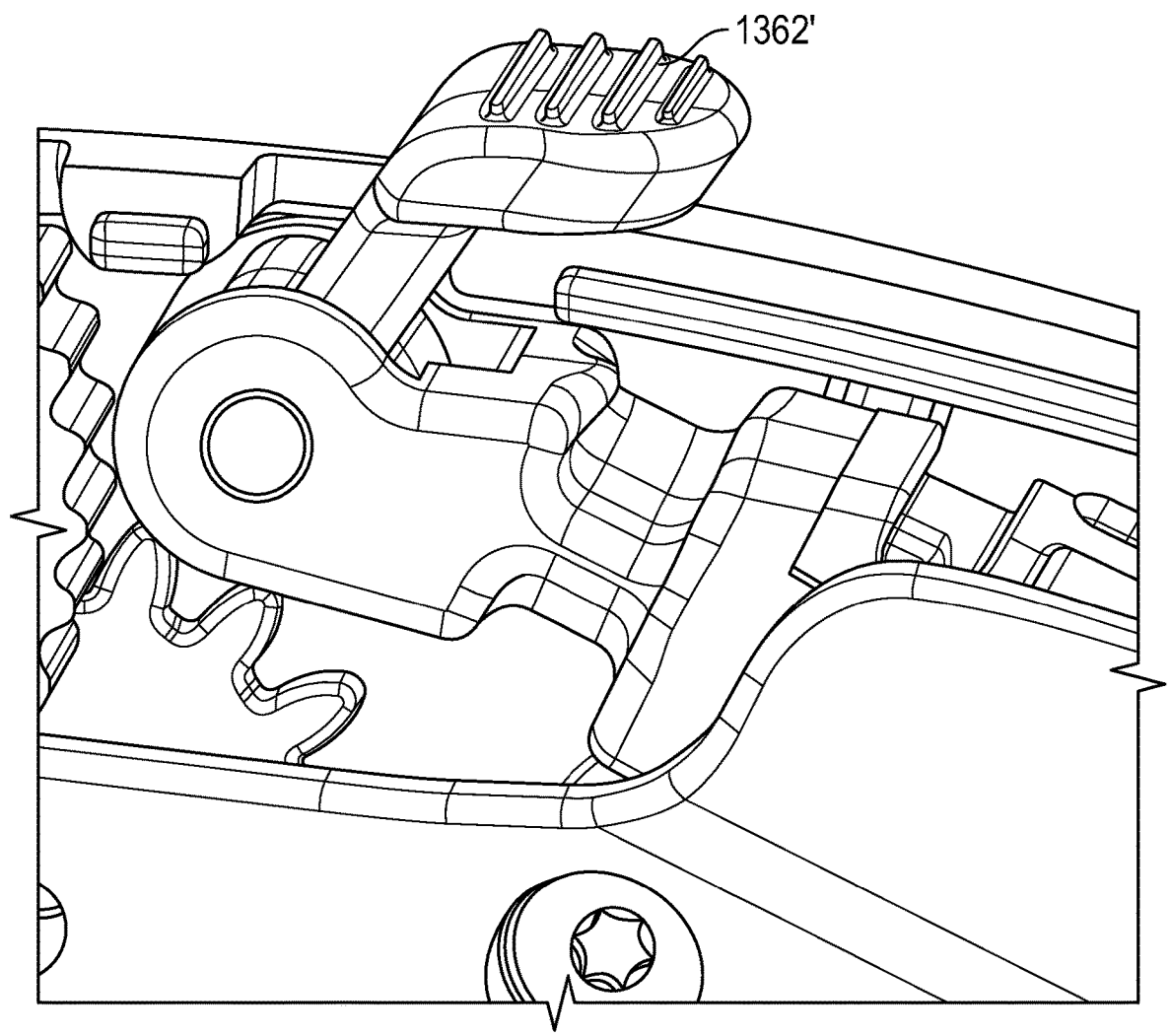
FIG. 35 is a partial cross-sectional view of an alternative visco control element shape for use with the viscoelastic delivery system of FIGS. 32-34.

The visco trigger may be a simple lever, such as toggle lever 1062 in FIG. 28 or toggle lever 1362 in FIGS. 32-34, or it may alternatively have an angled shape, such as toggle lever 1362' shown in FIG. 35. Visco trigger 1062, visco trigger 1362, and visco trigger 1362' may be formed from plastic (e.g., PEEK), stainless steel, or any other suitable material.

Figure 36:
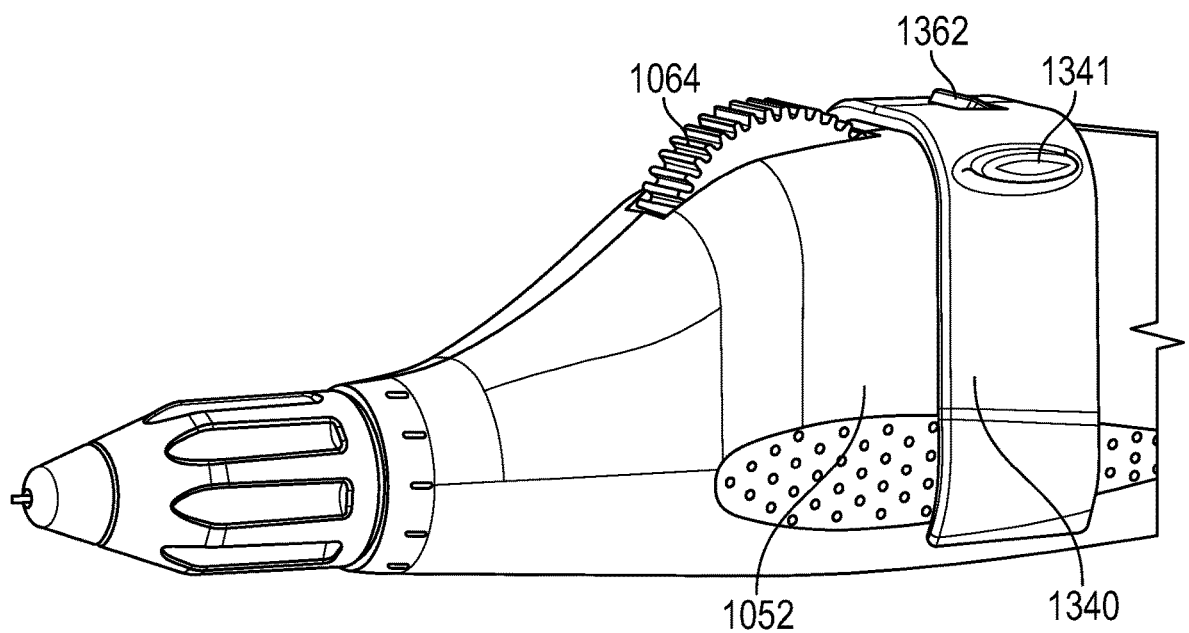
FIG. 36 is a perspective view illustrating a toggle lock for use with the viscoelastic delivery system of this invention.
Figure 37:
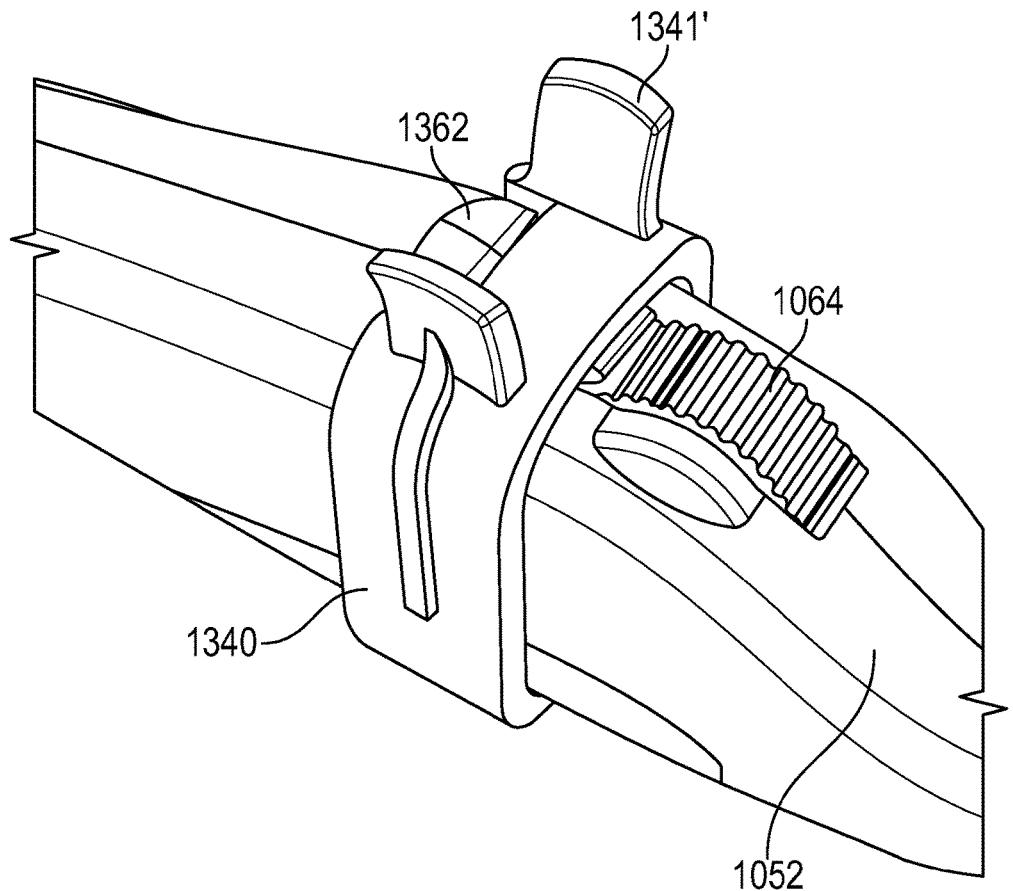
FIG. 37 is a perspective view illustrating an alternative toggle lock for use with the viscoelastic delivery system of this invention.

FIG. 36 shows a toggle lock 1340 that keeps visco trigger 1362 in its rearward (open) position during priming. Toggle lock 1340 may be removed from handle 1052 by pulling upward on tabs 1341 after priming and before pressurizing the visco cartridge (e.g., by turning compression knob 1220 of the embodiment of FIG. 20) and using the viscoelastic delivery system to treat a patient. FIG. 37 shows an alternative toggle lock 1340' with larger tabs 1341' to facilitate its removal from handle 1052.

Figure 38:
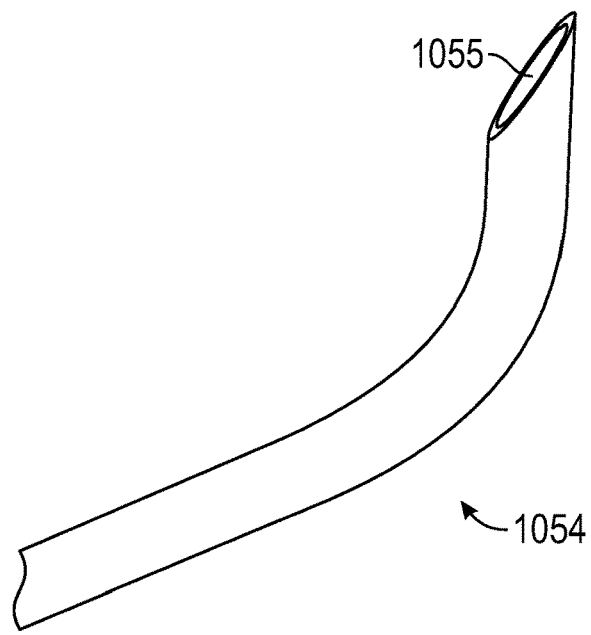
FIG. 38 is a perspective view illustrating a beveled distal tip of a cannula extending from a viscoelastic delivery system according to embodiments of the invention.
Figure 39:
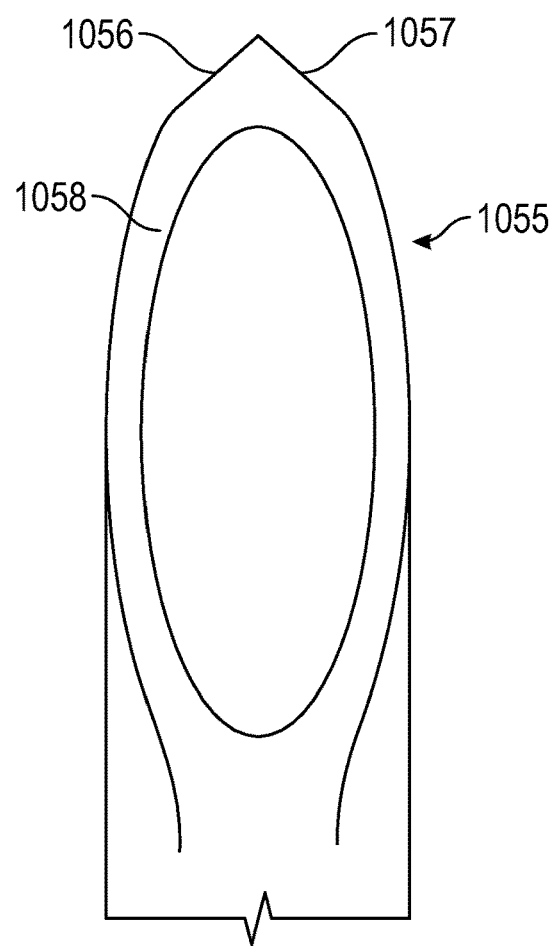
FIG. 39 is an elevational view of the beveled distal tip of the cannula of FIG. 38
Figure 40:
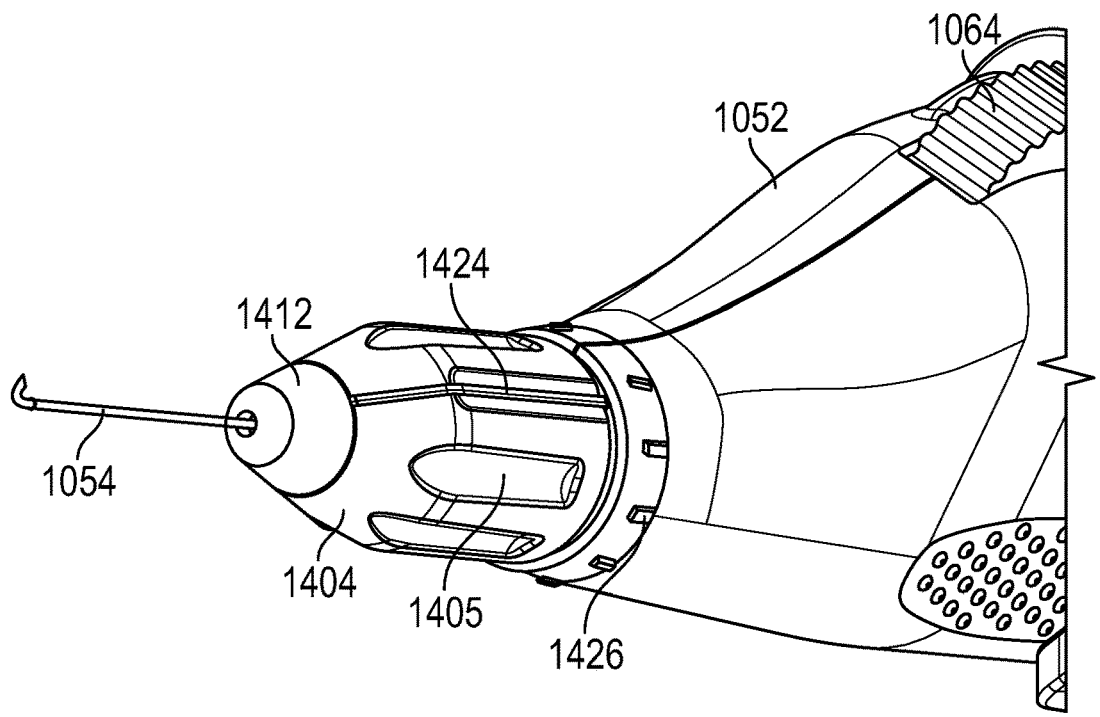
FIG. 40 is a perspective view showing a cannula rotation feature of the viscoelastic delivery system.
Figure 41:
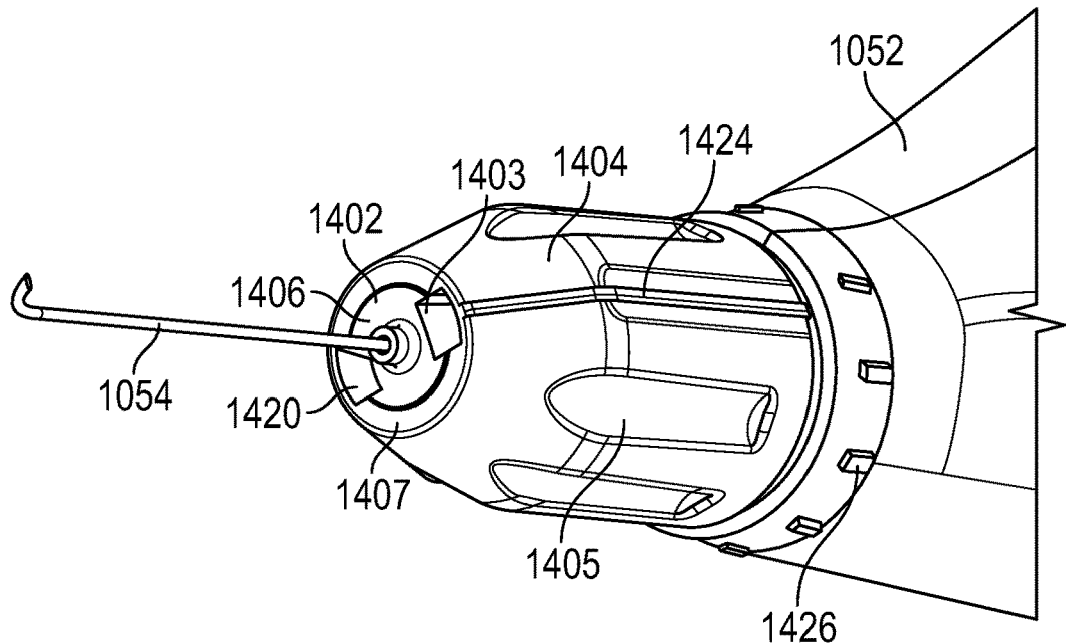
FIG. 41 is a perspective view of aspects of the cannula rotation feature of FIG. 40.
Figure 42:
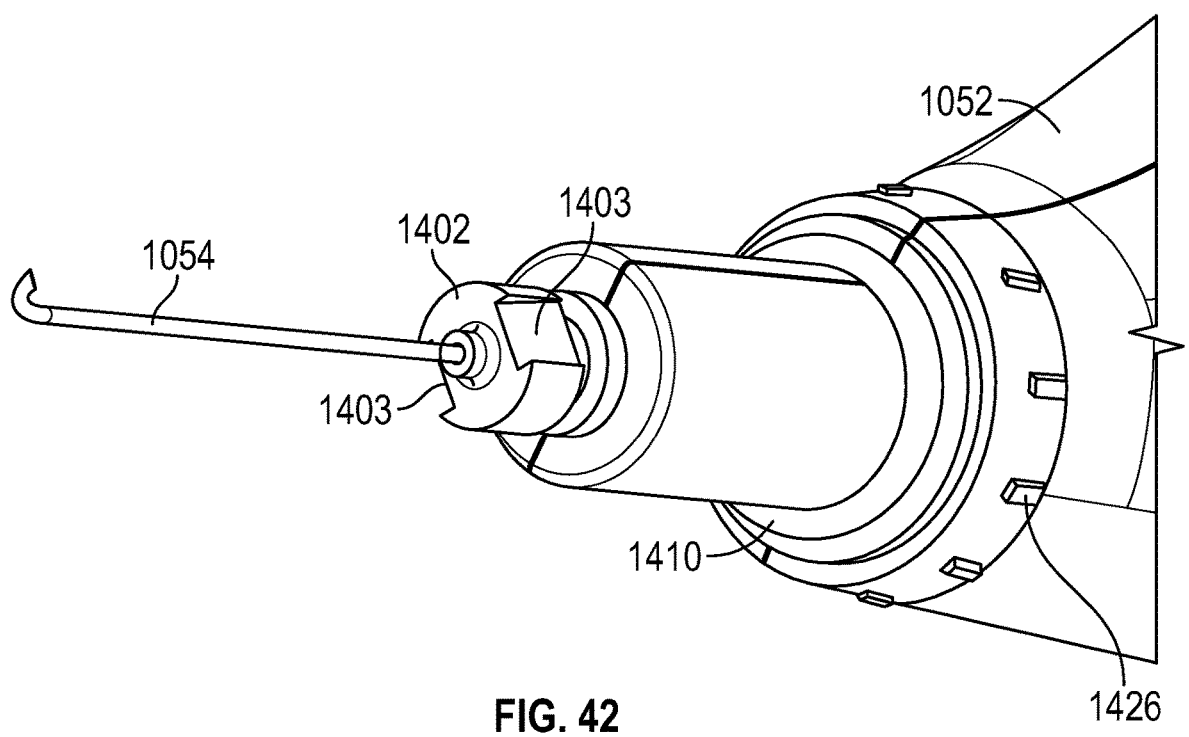
FIG. 42 is a perspective view of aspects of the cannula rotation feature of FIG. 40.
Figure 43:
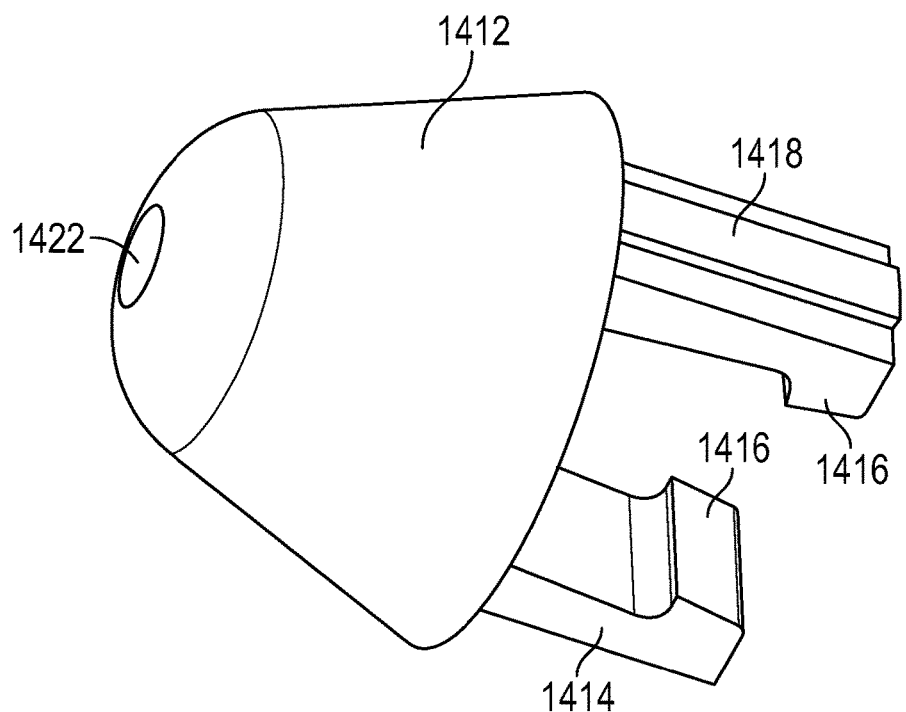
FIG. 43 is a perspective view of a component of the cannula rotation feature of FIG. 40.
Figure 44:
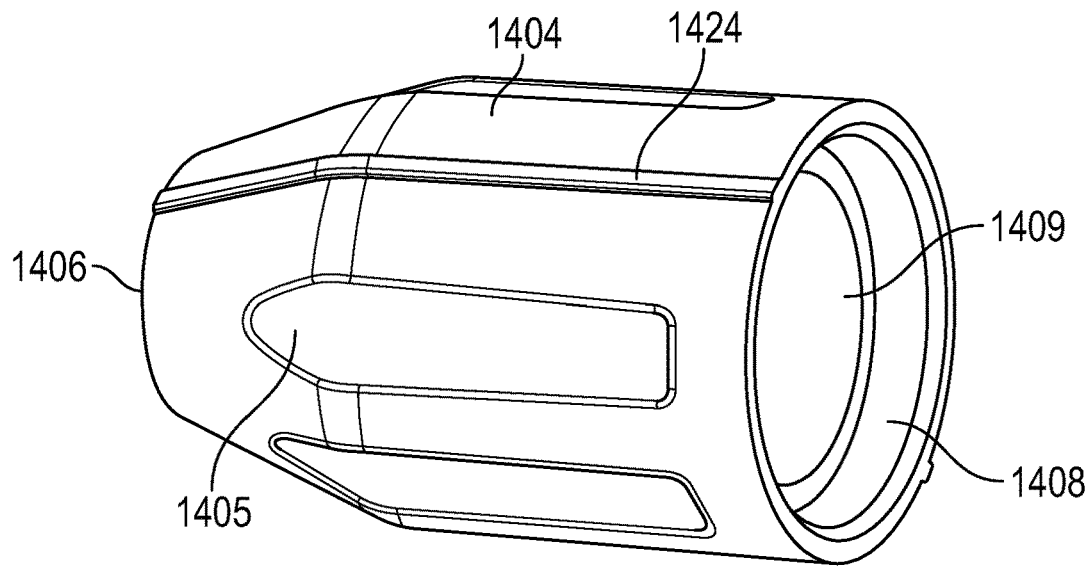
FIG. 44 is a perspective view of another component of the cannula rotation feature of FIG. 40.

FIGS. 38 and 39 show details of the distal end of cannula 1054 of the viscoelastic delivery system, which has a beveled tip 1055. Tip 1055 may be electropolished so that it is not so sharp as to puncture or shear the conduit 1053 (not shown in FIG. 38) as it moves into and out of cannula 1054, but sharp enough to puncture trabecular meshwork tissue during the therapy. As shown in FIG. 39, tip 1055 has two flat surfaces 1056 and 1057 at the distal end formed, e.g., by grinding the angled surface 1058.

FIGS. 40-44 show how the curved cannula 1054 extending from handle 1052 may be rotated a known amount with respect to the handle. Cannula 1054 is welded to a rotatable hub 1402 extending from the distal end of the handle 1052 with the angled tip of the cannula pointing to one of two notches 1403 in hub 1402. A barrel 1404 extends around hub 1402. Barrel 1404 has a groove 1408 at a proximal open end 1409 that rests against an O-ring 1410 on the handle. A locking plug 1412 is disposed with its proximally facing surface against a distally facing surface 1407 surrounding a distal opening 1406 of barrel 1404 to connect barrel 1404 to hub 1402 so that barrel 1404, hub 1402 and cannula 1054 rotate together. Two legs 1414 extend proximally from locking plug 1412 through notches 1403. Tabs 1416 on legs 1414 engage proximally facing surfaces of hub 1402 to press barrel proximally against O-ring 1410, and ridges 1418 on legs 1414 engage corresponding grooves 1420 on the inside of barrel 1404. Cannula 1054 extends through distal opening 1406 of barrel 1404 and through an opening 1422 in locking plug 1412. When assembled, a line 1424 on the exterior of barrel 1404 lines up with the radial direction in which the angled tip of 1054 extends. By orienting line 1424 with graduated "clock hour" markings and/or numbers 1426 on handle 1052, a user will know the orientation of the curved tip of cannula 1054 even when the cannula itself cannot be easily seen, e.g., when the cannula has been inserted into a patient's eye. O-ring 1410 provides friction resisting free movement of barrel 1404 to hold the barrel/hub/cannula assembly in its rotational position. Barrel 1404 may have grooves, ridges or knurls 1405 for easy gripping.

The systems described herein provide a novel and unique viscoelastic delivery system. The delivery system itself includes separate triggers or mechanisms for deploying or administering viscoelastic material from the delivery system into the eye and for controlling the position from which the viscoelastic material is deployed (via the conduit). Methods of use can also be provided herein.

Figure 45:
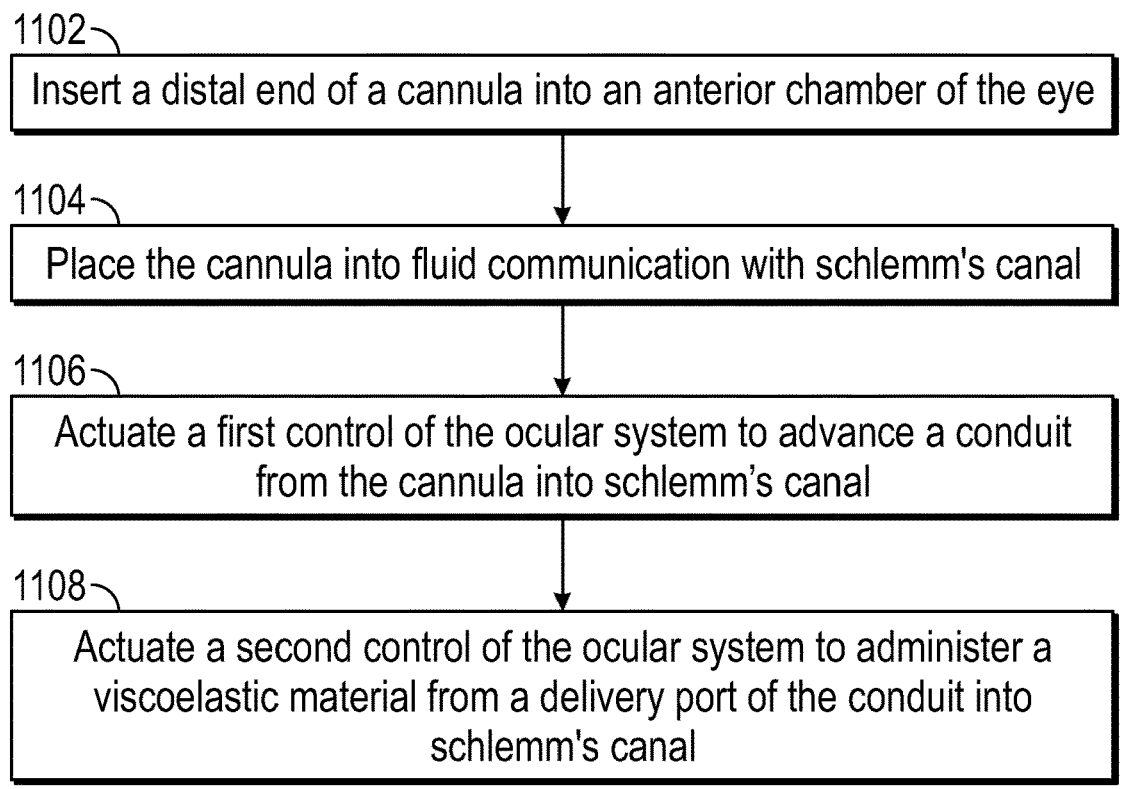
FIG. 45 is a flowchart describing a method of treating an eye of a patient.

Referring to FIG. 45, a flowchart is provided describing a method of treating an eye of a patient with an ocular system. The method can include the following steps:

At an operation 1102 of FIG. 45, the method can include inserting a distal end of a cannula of the ocular system into an anterior chamber of the eye. In some embodiments, the cannula can be inserted through an incision of the eye into the anterior chamber. In other embodiments, the cannula can pierce the eye with its distal tip to enter the anterior chamber.

At an operation 1104, the method can further include placing the distal end of the cannula into fluid communication with Schlemm's canal such that the cannula enters Schlemm's canal in a substantially tangential orientation.

At an operation 1106, the method can further include actuating a first control of the ocular system to advance a conduit out of the cannula and into Schlemm's canal. The first control can also further advance and retract the conduit within Schlemm's canal, and it can retract the conduit fully into the cannula. As described above, the delivery system can include a viscoelastic advancement wheel configured to move the conduit of the delivery system within the cannula. The conduit can be moved, for example, distally from the cannula to cause the conduit to partially extend beyond the distal opening of the cannula. Alternatively, the conduit can be moved proximally relative to the distal end of the cannula. Adjusting the position of the conduit relative to the cannula can be used to adjust the position of the viscoelastic delivery port of the conduit. In one example, the viscoelastic delivery port comprises an opening at a distal end of the conduit. The viscoelastic delivery port can be configured to administer a flow of viscoelastic material into tissue or a body structure. In some implementations, the first control can be a control wheel, lever, switch, button, or the like disposed on a handle of the ocular system. In other embodiments, the first control can be remote from a handle of the system (e.g., a foot switch). The first control can include physical features such as detents, notches, etc. to give a user tactile feedback on how far the conduit has been advanced or retracted.

At an operation 1108, the method can further include actuating a second control of the ocular system to administer a viscoelastic material into the conduit and into Schlemm's canal. In some implementations, the second control can be a control wheel, lever, switch, button, or the like disposed on the handle of the ocular system. The first control and the second control can be adjacent to another, or can be positioned on the handle to allow the user to manipulate both the first control and the second control. In some embodiments, the second control is remote from the handle (e.g., positioned on the viscoelastic module).

The second control can comprise an on/off switch, in which viscoelastic material flows out of the conduit in the on position and does not flow out of the conduit in the off position. In other embodiments, the second control can deposit a known volume of viscoelastic material into Schlemm's canal. The second control gives the user control over how much viscoelastic material is delivered into Schlemm's canal. In some examples, a consistent bolus or volume of viscoelastic material can be injected into Schlemm's canal each time the position of the viscoelastic delivery port is adjusted. In some embodiments, a larger volume of viscoelastic material can be administered when desired. The position of the conduit, and thus the viscoelastic delivery port, can be controlled separately by the user from the administration of viscoelastic material (e.g., via the first and second controls, respectively).

In some embodiments, the viscoelastic material can be administered prior to delivery of an ocular implant to open aqueous humor outflow pathways. In other embodiments, the viscoelastic material can be administered after an ocular implant is placed within Schlemm's canal.

It is to be understood that even though numerous characteristics of various embodiments have been set forth in the foregoing description, together with details of the structure and function of various embodiments, this detailed description is illustrative only, and changes may be made in detail, especially in matters of structure and arrangements of parts illustrated by the various embodiments to the full extent indicated by the broad general meaning of the terms in which the appended claims are expressed.

What is claimed is:

1. An ocular viscoelastic delivery system, comprising:
   a handle;
   a cannula defining a passageway extending from the handle to a distal cannula opening, the cannula being sized and configured to be advanced through an anterior chamber of a patient's eye to place the distal cannula opening in fluid communication with Schlemm's canal of the eye;
   a conduit slidably disposed within the cannula passageway, the conduit including a viscoelastic delivery port, at least a distal portion of the conduit being sized and configured to be advanced from the cannula into Schlemm's canal;
   a viscoelastic module in fluid communication with the conduit and the viscoelastic delivery port, the viscoelastic module being configured to contain a pressurized volume of viscoelastic material outside of the handle, wherein the viscoelastic module comprises a reservoir and a spring configured to pressurize viscoelastic material in the reservoir, wherein the viscoelastic module further comprises an inlet port adapted to engage with a viscoelastic syringe, the inlet port being fluid being fluidly communicable with the reservoir;
   a first control configured to adjust a position of the conduit and the viscoelastic delivery port relative to the cannula; and a second control configured to release pressurized viscoelastic material from the viscoelastic module through the conduit and viscoelastic delivery port into Schlemm's canal.

2. The delivery system of claim 1, wherein the viscoelastic module further comprises:
a cradle configured to receive a viscoelastic syringe; and
a force assembly configured to contact a plunger of the viscoelastic syringe, the force assembly further being configured to apply a constant force against the plunger.

3. The delivery system of claim 2, wherein the force assembly further comprises an adjustment mechanism configured to adjust a position of the force assembly with respect to the plunger.

4. The delivery system of claim 1, further comprising an actuator extending from the viscoelastic module and configured to compress the spring to pressurize the reservoir.

5. The delivery system of claim 1, further comprising a check valve disposed between the inlet port and the reservoir, the check valve being configured to open to permit pressurized viscoelastic material to flow from the viscoelastic syringe through the inlet port to the reservoir and to close to prevent viscoelastic material from the reservoir out of the inlet port.

6. The delivery system of claim 1, wherein the first control and the second control are disposed on the handle.

7. The delivery system of claim 1, wherein a single actuation of the first control moves the conduit by a known distance.

8. The delivery system of claim 1, further comprising a cantilever spring engaged with the first control and adapted to provide tactile feedback of movement of the first control.

9. The delivery system of claim 1, wherein a single actuation of the second control administers a known volume of viscoelastic material from the conduit and viscoelastic delivery port into Schlemm's canal.

10. The delivery system of claim 1, wherein the second control comprises a toggle lever operable to be moved to a first position to open a valve to deliver viscoelastic material from the viscoelastic module into the conduit, the second control further comprising a spring operable to move the toggle to a second position to close the valve.

11. The delivery system of claim 10, further comprising a toggle lock configured to hold the toggle lever in the first position.

12. The delivery system of claim 11, wherein the toggle lock is removably disposed on an exterior surface of the handle and engaged with the toggle lever.

13. The delivery system of claim 1, further comprising tubing extending from the viscoelastic module to the handle, the tubing comprising a fluid lumen extending from an outlet of the viscoelastic module to an inlet control in the handle.

14. The delivery system of claim 13, wherein the tubing has a length of 3-4 inches.

15. An ocular viscoelastic delivery system, comprising:
a handle;
a cannula defining a passageway extending from the handle to a distal cannula opening, the cannula being sized and configured to be advanced through an anterior chamber of a patient's eye to place the distal cannula opening in fluid communication with Schlemm's canal of the eye;
a conduit slidably disposed within the cannula passageway, the conduit including a viscoelastic delivery port, at least a distal portion of the conduit being sized and configured to be advanced from the cannula into Schlemm's canal;
a viscoelastic module in fluid communication with the conduit and the viscoelastic delivery port, the viscoelastic module being configured to contain a pressurized volume of viscoelastic material outside of the handle;
a first control configured to adjust a position of the conduit and the viscoelastic delivery port relative to the cannula; and
a second control configured to release pressurized viscoelastic material from the viscoelastic module through the conduit and viscoelastic delivery port into Schlemm's canal, wherein the second control comprises a toggle lever operable to be moved to a first position to open a valve to deliver viscoelastic material from the viscoelastic module into the conduit, the second control further comprising a spring operable to move the toggle to a second position to close the valve.

16. The delivery system of claim 15, wherein the viscoelastic module further comprises:
a cradle configured to receive a viscoelastic syringe; and
a force assembly configured to contact a plunger of the viscoelastic syringe, the force assembly further being configured to apply a constant force against the plunger.

17. The delivery system of claim 16, wherein the force assembly further comprises an adjustment mechanism configured to adjust a position of the force assembly with respect to the plunger.

18. The delivery system of claim 15, wherein the viscoelastic module comprises a reservoir and a spring configured to pressurize viscoelastic material in the reservoir.

19. The delivery system of claim 15, further comprising a toggle lock configured to hold the toggle lever in the first position.

20. The delivery system of claim 19, wherein the toggle lock is removably disposed on an exterior surface of the handle and engaged with the toggle lever.

* * * * *